(12) United States Patent
Bleich et al.

(10) Patent No.: US 7,740,631 B2
(45) Date of Patent: Jun. 22, 2010

(54) DEVICES AND METHODS FOR TISSUE MODIFICATION

(75) Inventors: Jeffery L. Bleich, Palo Alto, CA (US); Edwin J. Hlavka, Palo Alto, CA (US)

(73) Assignee: Baxano, Inc., San Jose, CA (US)

( * ) Notice: Subject to any disclaimer, the term of this patent is extended or adjusted under 35 U.S.C. 154(b) by 1227 days.

(21) Appl. No.: 11/251,204

(22) Filed: Oct. 15, 2005

(65) Prior Publication Data

US 2006/0089640 A1    Apr. 27, 2006

Related U.S. Application Data

(60) Provisional application No. 60/619,306, filed on Oct. 15, 2004, provisional application No. 60/622,865, filed on Oct. 28, 2004.

(51) Int. Cl.
*A61B 17/00* (2006.01)
(52) U.S. Cl. .................. 606/79; 606/41; 606/170; 607/116; 607/117
(58) Field of Classification Search .............. 606/92, 606/45–49, 82–85, 167, 170, 175, 176, 177, 606/79; 600/546, 544
See application file for complete search history.

(56) References Cited

U.S. PATENT DOCUMENTS

| 184,804 | A | 1/1876 | Stohlmann |
|---|---|---|---|
| 289,104 | A | 11/1883 | How |
| 863,389 | A | 8/1907 | Harkin |
| 1,039,487 | A | 9/1912 | Casebolt |
| 1,201,467 | A | 10/1916 | Hoglund |
| 1,374,638 | A | 4/1921 | De Cew et al. |
| 1,543,195 | A | 6/1925 | Thygesen |
| 1,690,812 | A | 11/1928 | Bertels |
| 1,938,200 | A | 12/1933 | Wells |
| 2,243,757 | A | 5/1941 | Kohls et al. |
| 2,269,749 | A | 1/1942 | Wilkie |

(Continued)

FOREIGN PATENT DOCUMENTS

DE    3209403 A1    9/1983

(Continued)

OTHER PUBLICATIONS

K. Tomita and N. Kawahara, The Threadwire saw: a New Device for cutting bone. A brief Note, Dec. 1996, The journal of Bone and Joint Surgery, vol. 78-a, No. 12. 1915-1917.*

(Continued)

*Primary Examiner*—Linda C Dvorak
*Assistant Examiner*—Amanda Scott
(74) *Attorney, Agent, or Firm*—Shay Glenn LLP

(57) ABSTRACT

Methods and apparatus are provided for selective surgical removal of tissue. In one variation, tissue may be ablated, resected, removed, or otherwise remodeled by standard small endoscopic tools delivered into the epidural space through an epidural needle. The sharp tip of the needle in the epidural space, can be converted to a blunt tipped instrument for further safe advancement. The current invention includes specific tools that enable safe tissue modification in the epidural space, including a barrier that separates the area where tissue modification will take place from adjacent vulnerable neural and vascular structures. A nerve stimulator may be provided to reduce a risk of inadvertent neural abrasion.

19 Claims, 55 Drawing Sheets

U.S. PATENT DOCUMENTS

| | | | |
|---|---|---|---|
| 2,372,553 A | 3/1945 | Coddington | |
| 2,437,697 A | 3/1948 | Kalom | |
| 2,516,882 A | 8/1950 | Kalom | |
| 2,704,064 A | 5/1955 | Fizzell | |
| 2,820,281 A | 1/1958 | Amsen | |
| 2,843,128 A | 7/1958 | Storz | |
| 2,982,005 A | 5/1961 | Booth | |
| RE25,582 E | 5/1964 | Davies | |
| 3,150,470 A | 9/1964 | Barron | |
| 3,389,447 A | 6/1968 | Theobald et al. | |
| 3,491,776 A | 1/1970 | Fleming | |
| 3,495,590 A | 2/1970 | Zeiller | |
| 3,528,152 A | 9/1970 | Funakubo et al. | |
| 3,624,484 A | 11/1971 | Colyer | |
| 3,640,280 A | 2/1972 | Slanker et al. | |
| 3,651,844 A | 3/1972 | Barnes | |
| 3,664,329 A | 5/1972 | Naylor | |
| 3,682,162 A | 8/1972 | Colyer | |
| 3,699,729 A | 10/1972 | Garvey et al. | |
| 3,752,166 A | 8/1973 | Lyon et al. | |
| 3,774,355 A | 11/1973 | Dawson et al. | |
| 3,830,226 A | 8/1974 | Staub et al. | |
| 3,835,859 A | 9/1974 | Roberts et al. | |
| 3,956,858 A | 5/1976 | Catlin et al. | |
| 3,957,036 A | 5/1976 | Normann | |
| 3,978,862 A | 9/1976 | Morrison | |
| 4,015,931 A | 4/1977 | Thakur | |
| 4,099,519 A | 7/1978 | Warren | |
| 4,108,182 A | 8/1978 | Hartman et al. | |
| 4,160,320 A | 7/1979 | Wikoff | |
| 4,172,440 A | 10/1979 | Schneider et al. | |
| 4,203,444 A | 5/1980 | Bonnell et al. | |
| 4,207,897 A | 6/1980 | Lloyd et al. | |
| 4,259,276 A | 3/1981 | Rawlings | |
| 4,405,061 A | 9/1983 | Bergandy | |
| D273,806 S | 5/1984 | Bolesky et al. | |
| 4,464,836 A | 8/1984 | Hissa | |
| 4,502,184 A | 3/1985 | Karubian | |
| 4,515,168 A | 5/1985 | Chester et al. | |
| 4,545,374 A | 10/1985 | Jacobson | |
| 4,573,448 A | 3/1986 | Kambin | |
| 4,580,545 A | 4/1986 | Dorsten | |
| 4,590,949 A * | 5/1986 | Pohndorf | 607/117 |
| 4,616,660 A | 10/1986 | Johns | |
| 4,621,636 A | 11/1986 | Fogarty | |
| 4,625,725 A | 12/1986 | Davison et al. | |
| 4,660,571 A | 4/1987 | Hess et al. | |
| 4,678,459 A | 7/1987 | Onik et al. | |
| 4,690,642 A | 9/1987 | Kyotani | |
| 4,700,702 A | 10/1987 | Nilsson | |
| 4,709,699 A | 12/1987 | Michael et al. | |
| 4,794,931 A | 1/1989 | Yock | |
| 4,808,157 A | 2/1989 | Coombs | |
| 4,856,193 A | 8/1989 | Grachan | |
| 4,867,155 A | 9/1989 | Isaacson | |
| 4,872,452 A | 10/1989 | Alexson | |
| 4,873,978 A | 10/1989 | Ginsburg | |
| 4,883,460 A | 11/1989 | Zanetti | |
| 4,894,063 A | 1/1990 | Nashe | |
| RE33,258 E | 7/1990 | Onik et al. | |
| 4,943,295 A | 7/1990 | Hartlaub et al. | |
| 4,957,117 A | 9/1990 | Wysham | |
| 4,962,766 A | 10/1990 | Herzon | |
| 4,973,329 A | 11/1990 | Park et al. | |
| 4,990,148 A | 2/1991 | Worrick, III et al. | |
| 4,994,036 A | 2/1991 | Biscoping et al. | |
| 4,994,072 A | 2/1991 | Bhate et al. | |
| 4,995,200 A | 2/1991 | Eberhart | |
| 5,019,082 A | 5/1991 | Frey et al. | |
| 5,026,379 A | 6/1991 | Yoon | |
| 5,026,386 A | 6/1991 | Michelson | |
| 5,089,003 A | 2/1992 | Fallin et al. | |
| 5,100,424 A | 3/1992 | Jang et al. | |
| 5,125,928 A | 6/1992 | Parins et al. | |
| 5,147,364 A | 9/1992 | Comparetto | |
| 5,161,534 A | 11/1992 | Berthiaume | |
| 5,163,939 A | 11/1992 | Winston | |
| 5,176,649 A | 1/1993 | Wakabayashi | |
| 5,178,145 A | 1/1993 | Rea | |
| 5,195,507 A | 3/1993 | Bilweis | |
| 5,201,704 A | 4/1993 | Ray | |
| 5,215,105 A | 6/1993 | Kizelshteyn et al. | |
| 5,219,358 A | 6/1993 | Bendel et al. | |
| 5,242,418 A | 9/1993 | Weinstein | |
| 5,250,035 A | 10/1993 | Smith et al. | |
| 5,255,691 A | 10/1993 | Otten | |
| 5,281,218 A | 1/1994 | Imran | |
| 5,284,153 A | 2/1994 | Raymond et al. | |
| 5,284,154 A | 2/1994 | Raymond et al. | |
| 5,300,077 A | 4/1994 | Howell | |
| 5,325,868 A | 7/1994 | Kimmelstiel | |
| 5,341,807 A | 8/1994 | Nardella | |
| 5,351,679 A | 10/1994 | Mayzels et al. | |
| 5,353,784 A | 10/1994 | Nady-Mohamed | |
| 5,353,789 A | 10/1994 | Schlobohm | |
| 5,353,802 A | 10/1994 | Ollmar | |
| 5,374,261 A | 12/1994 | Yoon | |
| 5,383,879 A * | 1/1995 | Phillips | 606/86 R |
| 5,385,146 A | 1/1995 | Goldreyer | |
| 5,387,218 A | 2/1995 | Meswania | |
| 5,396,880 A | 3/1995 | Kagan et al. | |
| 5,423,331 A | 6/1995 | Wysham | |
| 5,437,661 A | 8/1995 | Rieser | |
| 5,439,464 A | 8/1995 | Shapiro | |
| 5,441,044 A | 8/1995 | Tovey et al. | |
| 5,441,510 A | 8/1995 | Simpson et al. | |
| 5,454,815 A | 10/1995 | Geisser et al. | |
| 5,496,325 A | 3/1996 | McLees | |
| 5,512,037 A | 4/1996 | Russell et al. | |
| 5,531,749 A | 7/1996 | Michelson | |
| 5,554,110 A * | 9/1996 | Edwards et al. | 604/22 |
| 5,555,892 A | 9/1996 | Tipton | |
| 5,560,372 A | 10/1996 | Cory | |
| 5,562,695 A * | 10/1996 | Obenchain | 606/185 |
| 5,571,181 A | 11/1996 | Li | |
| 5,582,618 A | 12/1996 | Chin et al. | |
| 5,598,848 A | 2/1997 | Swanson et al. | |
| 5,620,447 A | 4/1997 | Smith et al. | |
| 5,630,426 A | 5/1997 | Eggers et al. | |
| 5,643,304 A | 7/1997 | Schechter et al. | |
| 5,656,012 A | 8/1997 | Sienkiewicz | |
| 5,680,860 A | 10/1997 | Imran | |
| 5,681,324 A | 10/1997 | Kammerer et al. | |
| 5,697,889 A | 12/1997 | Slotman et al. | |
| 5,709,697 A | 1/1998 | Ratcliff et al. | |
| 5,725,530 A | 3/1998 | Popken | |
| 5,735,792 A | 4/1998 | Vanden Hoek et al. | |
| 5,755,732 A | 5/1998 | Green et al. | |
| 5,759,159 A | 6/1998 | Masreliez | |
| 5,762,629 A | 6/1998 | Kambin | |
| 5,766,168 A | 6/1998 | Mantell | |
| 5,769,865 A | 6/1998 | Kermode et al. | |
| 5,775,331 A | 7/1998 | Raymond et al. | |
| 5,779,642 A | 7/1998 | Nightengale | |
| 5,795,308 A | 8/1998 | Russin | |
| 5,800,350 A | 9/1998 | Coppleson et al. | |
| 5,803,902 A | 9/1998 | Sienkiewicz et al. | |
| 5,803,904 A | 9/1998 | Mehdizadeh | |
| 5,807,263 A | 9/1998 | Chance | |
| 5,810,744 A | 9/1998 | Chu et al. | |
| 5,824,040 A | 10/1998 | Cox et al. | |
| 5,830,151 A | 11/1998 | Hadzic et al. | |
| 5,833,692 A | 11/1998 | Cesarini et al. | |
| 5,843,110 A | 12/1998 | Dross et al. | |

| | | | | | | |
|---|---|---|---|---|---|---|
| 5,846,196 | A | 12/1998 | Siekmeyer et al. | 6,451,335 | B1 * | 9/2002 | Goldenheim et al. ......... 424/426 |
| 5,846,244 | A | 12/1998 | Cripe | 6,454,767 | B2 | 9/2002 | Alleyne |
| 5,851,191 | A | 12/1998 | Gozani | 6,464,682 | B1 | 10/2002 | Snoke |
| 5,851,209 | A | 12/1998 | Kummer et al. | 6,466,817 | B1 | 10/2002 | Kaula et al. |
| 5,851,214 | A | 12/1998 | Larsen et al. | 6,468,289 | B1 | 10/2002 | Bonutti |
| 5,853,373 | A | 12/1998 | Griffith et al. | 6,470,209 | B2 | 10/2002 | Snoke |
| 5,865,844 | A | 2/1999 | Plaia et al. | 6,478,805 | B1 | 11/2002 | Marino et al. |
| 5,868,767 | A | 2/1999 | Farley et al. | 6,487,439 | B1 | 11/2002 | Skladnev et al. |
| 5,879,353 | A * | 3/1999 | Terry ........................ 606/85 | 6,488,636 | B2 | 12/2002 | Bryan et al. |
| 5,885,219 | A | 3/1999 | Nightengale | 6,500,128 | B2 | 12/2002 | Marino |
| 5,895,417 | A | 4/1999 | Pomeranz et al. | 6,500,189 | B1 | 12/2002 | Lang et al. |
| 5,897,583 | A | 4/1999 | Meyer et al. | 6,512,958 | B1 * | 1/2003 | Swoyer et al. ............ 607/117 |
| 5,899,909 | A | 5/1999 | Claren et al. | 6,516,223 | B2 | 2/2003 | Hofmann |
| 5,918,604 | A | 7/1999 | Whelan | 6,520,907 | B1 | 2/2003 | Foley et al. |
| 5,919,190 | A | 7/1999 | VanDusseldorp | 6,527,786 | B1 | 3/2003 | Davis et al. |
| 5,928,158 | A | 7/1999 | Aristides | 6,533,749 | B1 | 3/2003 | Mitusina et al. |
| 5,928,159 | A | 7/1999 | Eggers et al. | 6,535,759 | B1 | 3/2003 | Epstein et al. |
| 5,941,822 | A | 8/1999 | Skladnev et al. | 6,540,761 | B2 | 4/2003 | Houser |
| 5,961,522 | A | 10/1999 | Mehdizadeh | 6,546,270 | B1 | 4/2003 | Goldin et al. |
| 5,976,110 | A | 11/1999 | Greengrass et al. | 6,558,353 | B2 | 5/2003 | Zohmann |
| 5,976,146 | A | 11/1999 | Ogawa et al. | 6,562,033 | B2 | 5/2003 | Shah et al. |
| 6,002,964 | A | 12/1999 | Feler et al. | 6,564,078 | B1 | 5/2003 | Marino et al. |
| 6,004,326 | A | 12/1999 | Castro et al. | 6,564,079 | B1 | 5/2003 | Cory et al. |
| 6,010,493 | A | 1/2000 | Snoke | 6,564,088 | B1 | 5/2003 | Soller et al. |
| 6,015,406 | A | 1/2000 | Goble et al. | 6,569,160 | B1 | 5/2003 | Goldin et al. |
| 6,022,362 | A | 2/2000 | Lee et al. | 6,575,979 | B1 | 6/2003 | Cragg |
| 6,030,383 | A | 2/2000 | Benderev | 6,579,291 | B1 | 6/2003 | Keith et al. |
| 6,030,401 | A | 2/2000 | Marino | 6,584,345 | B2 | 6/2003 | Govari |
| 6,038,480 | A | 3/2000 | Hrdlicka et al. | 6,592,559 | B1 | 7/2003 | Pakter et al. |
| 6,048,345 | A | 4/2000 | Berke et al. | 6,597,955 | B2 | 7/2003 | Panescu et al. |
| 6,068,642 | A | 5/2000 | Johnson et al. | 6,606,523 | B1 | 8/2003 | Jenkins |
| 6,073,051 | A * | 6/2000 | Sharkey et al. ............. 607/99 | 6,609,018 | B2 | 8/2003 | Cory et al. |
| 6,099,514 | A | 8/2000 | Sharkey et al. | 6,610,066 | B2 | 8/2003 | Dinger et al. |
| 6,102,930 | A | 8/2000 | Simmons | 6,620,129 | B2 | 9/2003 | Stecker et al. |
| 6,106,558 | A | 8/2000 | Picha | 6,626,916 | B1 | 9/2003 | Yeung et al. |
| 6,113,534 | A * | 9/2000 | Koros et al. ............. 600/213 | 6,632,184 | B1 | 10/2003 | Truwit |
| D432,384 | S | 10/2000 | Simons | 6,638,233 | B2 | 10/2003 | Corvi et al. |
| 6,136,014 | A | 10/2000 | Sirimanne et al. | RE38,335 | E | 11/2003 | Aust et al. |
| 6,142,993 | A | 11/2000 | Whayne et al. | 6,648,883 | B2 | 11/2003 | Francischelli et al. |
| 6,146,380 | A | 11/2000 | Racz et al. | 6,666,874 | B2 | 12/2003 | Heitzmann et al. |
| 6,152,894 | A | 11/2000 | Kubler | 6,673,063 | B2 | 1/2004 | Brett |
| 6,169,916 | B1 * | 1/2001 | West ........................ 600/373 | 6,673,068 | B1 | 1/2004 | Berube |
| 6,205,360 | B1 | 3/2001 | Carter et al. | 6,678,552 | B2 | 1/2004 | Pearlman |
| 6,214,001 | B1 | 4/2001 | Casscells et al. | 6,682,535 | B2 | 1/2004 | Hoogland |
| 6,236,892 | B1 | 5/2001 | Feler | 6,682,536 | B2 | 1/2004 | Vardi et al. |
| 6,256,540 | B1 | 7/2001 | Panescu et al. | 6,699,246 | B2 | 3/2004 | Zucherman et al. |
| 6,259,945 | B1 | 7/2001 | Epstein et al. | 6,723,049 | B2 | 4/2004 | Skladnev et al. |
| 6,261,582 | B1 | 7/2001 | Needham et al. | 6,726,531 | B1 | 4/2004 | Harrel |
| 6,266,551 | B1 | 7/2001 | Osadchy et al. | 6,726,685 | B2 * | 4/2004 | To et al. ..................... 606/50 |
| 6,272,367 | B1 | 8/2001 | Chance | 6,733,496 | B2 | 5/2004 | Sharkey et al. |
| 6,277,094 | B1 | 8/2001 | Schendel | 6,736,835 | B2 | 5/2004 | Pellegrino et al. |
| 6,280,447 | B1 | 8/2001 | Marino et al. | 6,746,451 | B2 | 6/2004 | Middleton et al. |
| 6,292,702 | B1 | 9/2001 | King et al. | 6,752,814 | B2 | 6/2004 | Gellman et al. |
| 6,298,256 | B1 | 10/2001 | Meyer | 6,760,616 | B2 | 7/2004 | Hoey et al. |
| 6,312,392 | B1 | 11/2001 | Herzon | 6,772,012 | B2 | 8/2004 | Ricart et al. |
| 6,324,418 | B1 | 11/2001 | Crowley et al. | 6,776,765 | B2 * | 8/2004 | Soukup et al. ............ 600/585 |
| 6,343,226 | B1 | 1/2002 | Sunde et al. | 6,788,966 | B2 | 9/2004 | Kenan et al. |
| 6,358,254 | B1 | 3/2002 | Anderson | 6,790,210 | B1 | 9/2004 | Cragg et al. |
| 6,360,750 | B1 | 3/2002 | Gerber et al. | 6,805,695 | B2 | 10/2004 | Keith et al. |
| 6,364,886 | B1 | 4/2002 | Sklar | 6,805,697 | B1 | 10/2004 | Helm et al. |
| 6,368,324 | B1 | 4/2002 | Dinger et al. | 6,807,444 | B2 | 10/2004 | Tu et al. |
| 6,370,411 | B1 | 4/2002 | Osadchy et al. | 6,830,561 | B2 | 12/2004 | Jansen et al. |
| 6,370,435 | B2 | 4/2002 | Panescu et al. | 6,830,570 | B1 | 12/2004 | Frey et al. |
| 6,383,509 | B1 * | 5/2002 | Donovan et al. ............ 424/423 | 6,832,111 | B2 | 12/2004 | Tu et al. |
| 6,390,906 | B1 | 5/2002 | Subramanian | 6,845,264 | B1 | 1/2005 | Skladnev et al. |
| 6,391,028 | B1 | 5/2002 | Fanton et al. | 6,847,849 | B2 | 1/2005 | Mamo et al. |
| 6,416,505 | B1 | 7/2002 | Fleischman et al. | 6,851,430 | B2 | 2/2005 | Tsou |
| 6,423,071 | B1 | 7/2002 | Lawson | 6,872,204 | B2 | 3/2005 | Houser |
| 6,423,080 | B1 | 7/2002 | Gellman et al. | 6,875,221 | B2 | 4/2005 | Cull |
| 6,425,859 | B1 | 7/2002 | Foley et al. | 6,882,879 | B2 | 4/2005 | Rock |
| 6,425,887 | B1 | 7/2002 | McGuckin et al. | 6,899,716 | B2 | 5/2005 | Cragg |
| 6,436,101 | B1 | 8/2002 | Hamada | 6,907,884 | B2 | 6/2005 | Pellegrino et al. |
| 6,442,848 | B1 | 9/2002 | Dean | 6,911,003 | B2 | 6/2005 | Anderson et al. |

| | | |
|---|---|---|
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,976,986 B2 | 12/2005 | Berube |
| 6,991,643 B2 * | 1/2006 | Saadat .................... 606/221 |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,048,682 B2 | 5/2006 | Neisz et al. |
| 7,050,848 B2 | 5/2006 | Hoey et al. |
| 7,063,682 B1 * | 6/2006 | Whayne et al. .......... 604/95.04 |
| 7,070,556 B2 | 7/2006 | Anderson et al. |
| 7,070,596 B1 * | 7/2006 | Woloszko et al. ............ 606/41 |
| 7,079,883 B2 | 7/2006 | Marino et al. |
| 7,081,122 B1 | 7/2006 | Reiley et al. |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,189,240 B1 * | 3/2007 | Dekel .......................... 606/85 |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 * | 5/2007 | Hall et al. .................... 606/41 |
| 7,214,186 B2 | 5/2007 | Ritland |
| 7,223,278 B2 | 5/2007 | Davison et al. |
| 7,239,911 B2 | 7/2007 | Scholz |
| 7,282,061 B2 | 10/2007 | Sharkey et al. |
| 7,337,005 B2 * | 2/2008 | Kim et al. ................... 607/46 |
| 7,337,006 B2 * | 2/2008 | Kim et al. ................... 607/46 |
| 7,449,019 B2 * | 11/2008 | Uchida et al. ............... 606/27 |
| 7,470,236 B1 | 12/2008 | Kelleher et al. |
| 7,494,473 B2 | 2/2009 | Eggers et al. |
| 2001/0014806 A1 | 8/2001 | Ellman et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 * | 3/2002 | Hogendijk .................. 606/185 |
| 2002/0106681 A1 | 8/2002 | Wexler et al. |
| 2002/0138091 A1 | 9/2002 | Pflueger |
| 2002/0183647 A1 | 12/2002 | Gozani et al. |
| 2003/0023190 A1 | 1/2003 | Cox |
| 2003/0045808 A1 | 3/2003 | Kaula et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 * | 7/2004 | Hovda ......................... 606/15 |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 * | 8/2004 | Hossainy et al. ............ 623/1.42 |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199166 A1 | 10/2004 | Schmieding et al. |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 * | 9/2005 | Carrison et al. ............... 606/79 |
| 2005/0203599 A1 * | 9/2005 | Garabedian et al. ......... 607/116 |
| 2005/0209610 A1 | 9/2005 | Carrison |
| 2005/0209622 A1 * | 9/2005 | Carrison .................... 606/170 |
| 2005/0216023 A1 | 9/2005 | Aram et al. |
| 2005/0234425 A1 | 10/2005 | Miller et al. |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 * | 2/2006 | Solsberg et al. ............. 606/170 |
| 2006/0058732 A1 | 3/2006 | Harp |
| 2006/0064101 A1 | 3/2006 | Arramon |
| 2006/0079919 A1 | 4/2006 | Harp |
| 2006/0089633 A1 | 4/2006 | Bleich et al. |
| 2006/0089640 A1 * | 4/2006 | Bleich et al. ................. 606/45 |
| 2006/0089650 A1 | 4/2006 | Nolde |
| 2006/0094976 A1 | 5/2006 | Bleich |
| 2006/0095026 A1 | 5/2006 | Ricart et al. |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122653 A1 | 6/2006 | Bradley et al. |
| 2006/0122654 A1 | 6/2006 | Bradley et al. |
| 2006/0135882 A1 | 6/2006 | Bleich |
| 2006/0142753 A1 | 6/2006 | Francischelli et al. |
| 2006/0161189 A1 | 7/2006 | Harp |
| 2006/0184175 A1 | 8/2006 | Schomer et al. |

| | | | |
|---|---|---|---|
| 2006/0200153 A1 | 9/2006 | Harp | |
| 2006/0200154 A1 | 9/2006 | Harp | |
| 2006/0200155 A1 | 9/2006 | Harp | |
| 2006/0206115 A1 | 9/2006 | Schomer et al. | |
| 2006/0206117 A1 | 9/2006 | Harp | |
| 2006/0224078 A1 | 10/2006 | Hoey et al. | |
| 2006/0235451 A1 | 10/2006 | Schomer et al. | |
| 2006/0235452 A1 | 10/2006 | Schomer et al. | |
| 2006/0241648 A1 | 10/2006 | Bleich et al. | |
| 2006/0258951 A1 | 11/2006 | Bleich et al. | |
| 2006/0264994 A1 | 11/2006 | Schomer et al. | |
| 2007/0010717 A1 | 1/2007 | Cragg | |
| 2007/0049962 A1 | 3/2007 | Marino et al. | |
| 2007/0123888 A1 | 5/2007 | Bleich et al. | |
| 2007/0166345 A1 | 7/2007 | Pavcnik et al. | |
| 2007/0198019 A1 | 8/2007 | Schomer et al. | |
| 2007/0213733 A1 | 9/2007 | Bleich et al. | |
| 2007/0213734 A1 | 9/2007 | Bleich et al. | |
| 2007/0213735 A1 | 9/2007 | Saadat et al. | |
| 2007/0225703 A1 | 9/2007 | Schmitz et al. | |
| 2007/0260252 A1 | 11/2007 | Schmitz et al. | |
| 2007/0270795 A1 | 11/2007 | Francischelli et al. | |
| 2008/0033465 A1 | 2/2008 | Schmitz et al. | |
| 2008/0051812 A1 | 2/2008 | Schmitz et al. | |
| 2008/0125621 A1 | 5/2008 | Gellman et al. | |
| 2008/0125709 A1* | 5/2008 | Chang et al. | 604/96.01 |
| 2008/0146867 A1* | 6/2008 | Gellman et al. | 600/29 |
| 2008/0197024 A1 | 8/2008 | Simpson et al. | |
| 2008/0288005 A1 | 11/2008 | Jackson | |
| 2009/0018610 A1 | 1/2009 | Gharib et al. | |
| 2009/0125036 A1 | 5/2009 | Bleich | |
| 2009/0138056 A1 | 5/2009 | Anderson et al. | |
| 2009/0143829 A1 | 6/2009 | Shluzas | |
| 2009/0209879 A1 | 8/2009 | Kaula et al. | |

FOREIGN PATENT DOCUMENTS

| | | |
|---|---|---|
| DE | 04 036 804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 24065380 A2 | 3/2004 |
| RU | 2107459 | 3/1998 |
| WO | WO9734536 A2 | 9/1997 |
| WO | WO9918866 A1 | 4/1999 |
| WO | WO99/21500 A1 | 5/1999 |
| WO | WO00/67651 A1 | 11/2000 |
| WO | WO 01/08571 A1 | 2/2001 |
| WO | WO01/62168 A2 | 8/2001 |
| WO | WO0207901 A1 | 1/2002 |
| WO | WO0234120 A2 | 5/2002 |
| WO | WO02076311 A2 | 10/2002 |
| WO | WO03/026482 A2 | 4/2003 |
| WO | WO03/066147 A1 | 8/2003 |
| WO | WO2004002331 A1 | 1/2004 |
| WO | WO 2004/028351 A3 | 4/2004 |
| WO | WO2004/043272 A1 | 5/2004 |
| WO | WO2004056267 A1 | 7/2004 |
| WO | WO2004/078066 A2 | 9/2004 |
| WO | WO2004080316 A1 | 9/2004 |
| WO | WO2004096080 A2 | 11/2004 |
| WO | WO2005/009300 A1 | 2/2005 |
| WO | WO2005057467 A2 | 6/2005 |
| WO | WO 2005/077282 A1 | 8/2005 |
| WO | WO2005089433 A2 | 9/2005 |
| WO | WO2006009705 A2 | 1/2006 |
| WO | WO2006015302 A1 | 2/2006 |
| WO | WO2006017507 A2 | 2/2006 |
| WO | WO2006039279 A2 | 4/2006 |
| WO | WO2006042206 A2 | 4/2006 |
| WO | WO2006044727 A2 | 4/2006 |
| WO | WO2008008898 A2 | 1/2008 |

OTHER PUBLICATIONS

Baumgart et al., "Indikation and Technik der Knochendurchtrennung," Der Chirurg, 1998, vol. 69:1188-1196. (in German with Eng Summary).

Burrows, Harold, "Surgical instruments and appliances used in operations," Faber and Faber, London, 1937, total pp. 4.

Codman Laminectomy Shaver (a Johnson & Johnson company www.codman.com) catalogue, pp. 416-431, [online] Retrieved from the internet: <URL: http:||www.codman.com/PDFs/Catalog_04_R.pdf>.

Dammann, Gordon, Pictorial Encyclopedia of Civil War Medical Instruments and Equipment, Pictorial Histories Publishing Company, Missoula, Montana, 1983, Total pp. 2.

Edwards et al; "T-Saw Laminoplasty for the Management of Cervical Spondylotic Myelopathy," SPINE, Lippincott Williams & Wilkins, Inc., 2000, vol. 25 (14): 1788R1794.

Ellman Int. Disc-FX System Accessories K052241 [online] Retrieved from the Internet: <URL: http://www.ellman.com/ medical/ >.

Eralp et al., "A comparison of two osteotomy techniques for tibial lengthening," Archives of orthopaedic and trauma surgery, 2004, vol. 124:298R300.

Goel, Atul, "Neurosurgical forum, Supraorbital Craniotomy," Journal of Neurosurgery, 1994, vol. 81, 642-643.

Gore Smoother User Manual, W. L. Gore & Associates, Inc. Flagstaff, AZ, Dec. 1999,Total pp. 3.

Hata et al; "A less invasive surgery for rotator cuff tear: Mini-open repair," Journal of Shoulder and Elbow Surgery, 2001, vol. 10 No. 1, 11-16.

Integra Ruggles TM Kerrison Rongeurs [online] Retrieved from the internet: <URL: http://www.integra-ls.com/products!? product=22>.

Jun, Byung-Yoon, "Posterior Lumbar Interbody Fusion With Restoration of Lamina and Facet Fusion," SPINE, Lippincott Williams & Wilkins, Inc., 2000, vol. 25 No. 8, 917R922.

Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.

Miyamoto et al., "Kyphectomy Using a Surgical Threadwire (T-saw) for Kyphotic Deformity in a Child With Myelomeningocele," SPINE, Lippincott Williams & Wilkins, Inc., 2003, vol. 28 No. 10, E187RE190.

Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.

Mopec Bone-Cutting tool, Product brochure, Total pp. 4.

Paley et al., "Percutaneous Osteotomies," Orthopedic Clinics of North America, 1991, vol. 22 No. 4, 613-624.

Pancoast, Joseph, "A Treatise on Operative Surgery," Carey and Hart, Philadelphia,1844, Total pp. 11.

Park et al; "Cases of the Excision of Carious Joints," John Scrymgeour, Glasgow, 1806, Total pp. 6.

Peavy et al., "Comparison of Cortical Bone Ablations by Using Infrared Laser Wavelengths 2.9 to 9.2 μm, Lasers in Surgery and Medicine," 1999, vol. 26, 421R434.

Peltier, Leonard Orthopedics: A History and Iconography, Norman Publishing, San Francisco, 1993, Total pp. 3.

Rutkow, Ira, "Surgery An Illustrated History," Mosby'Year Book, Inc., St. Louis, 1993, Total pp. 4.

Schwieger et al., "Abrasive Water Jet Cutting as a New Procedure for Cutting Cancellous Bone'In Vitro Testing in Comparison with the Oscillating Saw," Wiley Interscience, www.interscience,wiley.com, Sep. 20, 2004, 223-228.

Sen, Cengiz, Tibia proksimalinde Gigli testeresi ile yapılanperkütan osteotominin güvenilirliği: Kadavra calismasi, Acta orthopaedica et traumatologica turcica, 2002, vol. 36, 136-140; (In Russian w/ Eng Summary).

Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672.

Shiraishi T., "A new technique for exposure of the cervical spine laminae," Journal of neurosurgery. Spine, 2002, vol. 96(1), 122-126.

Shiraishi T., Skip laminectomy—a new treatment for cervical spondylotic myelopathy, preserving bilateral muscular attachments to the spinous processes: a preliminary report, Spine, 2002, vol. 2(2), 108-115.

Skippen et al., "The Chain Saw R A Scottish Invention," Scottish Medical Journal, 2004, vol. 49(2), 72-75.

Stevens et al., "Calvarial Bone Graft Harvest Using the Gigli Saw," Journal of Oral and Maxillofacial Surgery, 1998, vol. 56, 798-799.

Takada et al., "Unusual Metastasis to the Cauda Equina From Renal Cell Carcinoma," SPINE, Lippincott Williams & Wilkins, Inc., 2003, vol. 28 No. 6, E114RE117.

Paktiss et al., "Afghan Percutaneous Osteotomy," Journal of Pediatric Orthopaedics, Raven Press Ltd, New York, 1993, vol. 13 No. 4, 531-533.

Tomita et al., "The Threadwire Saw: a New Device for Cutting Bone," The Journal of Bone and Joint Surgery, 1996, vol. 78, 1915-1917.

Truax, Charles, "The Mechanics of Surgery," Chicago, IL; 1899, Total pp. 3.

US Surgical Kerrison Spinal Rongeur K943116 [online] Retrieved from the internet: <URL: http://www.ussurg.com/uss/index.html>.

Wilkins, Robert H, "Neurosurgical Classics," Johnson Reprint Corporation, New York, 1965, 377-382.

Zeppelin Laminectomy Rongeur K901372, [online] Retrieved from the internet: <URL: http://www.zeppelin-medical.com/download/instruments.pdf>.

Bleich et al; U.S. Appl. No. 11/952,934 entitled "Tissue Removal Devices and Methods," filed Dec. 7, 2007.

Schmitz et al; U.S. Appl. No. 11/468,247 entitled "Tissue access guidewire system and method," filed Aug. 29, 2006.

Schmitz et al; U.S. Appl. No. 11/468,252 entitled "Tissue access guidewire system and method," filed Aug. 29, 2006.

Schmitz et al; U.S. Appl. No. 11/538,345 entitled "Articulating Tissue Cutting Device," filed Oct. 3, 2006.

Schmitz et al; U.S. Appl. No. 11/843,561 entitled "Surgical Probe and Method of Making," filed Aug. 22, 2007.

Schmitz et al; U.S. Appl. No. 11/870,370 entitled "Percutaneous Spinal Stenosis Treatment," filed Oct. 10, 2007.

Schmitz et al; U.S. Appl. No. 12/060,229 entitled "Method, system, and apparatus for neural localization," filed Mar. 31, 2008.

Barer, M. "Instrument to Enhance Passage of the Gigli Saw," Journal of Pediatric Orthopedics, 4:762-763, 1984 Raven Press, New York.

Brunori, A. et al., "Celebrating the centennial (1894-1994): Leonardo Gigli and his wire saw," J. Neurosurg., 82:1086-1090, 1995.

Fujita, T. et al., "Chordoma in the Cervical Spine Managed with En Bloc Excision," Spine, 24(17):1848-1851, 1999 Lippincott Williams & Wilkins, Inc.

Hara, M., et al., "En Bloc Laminoplasty Performed with Threadwire Saw: Technical Note," Neurosurgery, Jan. 2001, pp. 235-239, vol. 48, No. 1.

Honl, M., et al. "The Use of Water-Jetting Technology in Prostheses Revision Surgery—First Results of Parameter Studies on Bone and Bone Cement," J. Biomed Mater Res (Appl Biomater), 53:781-790, 2000 John Wiley & Sons, Inc.

Kawahara, N. et al., "Recapping T-Saw Laminoplasty for Spinal Cord Tumors," Spine, 24(13):1363-1370, 1999 Lippincott Williams & Wilkins, Inc.

Reckling, F., "Modified Stethoscope Earpiece Makes Excellent Gigli Saw Guide," Journal of Bone and Joint Surgery, 54-A(8):1787-1788, 1972.

Tomita, K. et al., "Expansive Midline T-Saw Laminoplasty (Modified Spinour Process-Splitting) for the Management of Cervical Myelopathy," Spine, 23(1):32-37, 1998 Lippincott Williams & Wilkins, Inc.

Tomita, K. et al., "Total en bloc spondylectomy and circumspinal decompression for solitary spinal metastasis," Paraplegia, 32:36-46, 1994.

Tomita, K. et al., "Total en bloc spondylectomy for solitary spinal metastases," International Orthopaedics (SICOT), 18:291-298, 1994.

Tomita et al., "The Use of the T-Saw for Expansive Midline laminoplasty in the Treatment of Cervical Myelopathy," Orthopedics and Traumatology, No. 3, pp. 169-178, 2002.

Bleich, et al.; U.S. Appl. No. 12/127,535 entitled "Guidewire exchange systems to treat spinal stenosis," filed May 27, 2008.

Bleich, et al.; U.S. Appl. No. 12/140,201 entitled "Devices and methods for measuring the space around a nerve root," filed Jun. 16, 2008.

Schmitz et al.; U.S. Appl. No. 12/170,392 entitled "Spinal access system and method," filed Jul. 9, 2008.

Fessler, Richard G., "Minimally Invasive Microendoscopic Decompressive Laminotomy for Lumbar Stenosis" [online], Copyright © 2006 American Association of Neurological Surgeons, Online CME Course, [Retrieved on Jun. 29, 2006], Retrieved from the Internet: <URL: http://www.aans.emedtrain.com/lumbar_stenosis/lumbarStenosis.swf>.

Schmitz et al.; U.S. Appl. No. 12/324,147 entitled "Tissue modification devices," filed Nov. 26, 2008.

Schmitz et al.; U.S. Appl. No. 12/352,385 entitled "Devices, methods and systems for neural localization," filed Jan. 12, 2009.

Bleich et al.; U.S. Appl. No. 12/352,978 entitled "Multiple pathways for spinal nerve rood decompression from a single access point," filed Jan. 13, 2009.

Bleich et al.; U.S. Appl. No. 12/504,545 entitled "Spinal access and neural localization," filed Jul. 16, 2009.

Schmitz et al.; U.S. Appl. No. 12/496,094 entitled "Access and tissue modification systems and methods," filed Jul. 1, 2009.

Bleich et al.; U.S. Appl. No. 12/428,369 entitled "Devices and methods for tissue modification," filed Apr. 22, 2009.

* cited by examiner

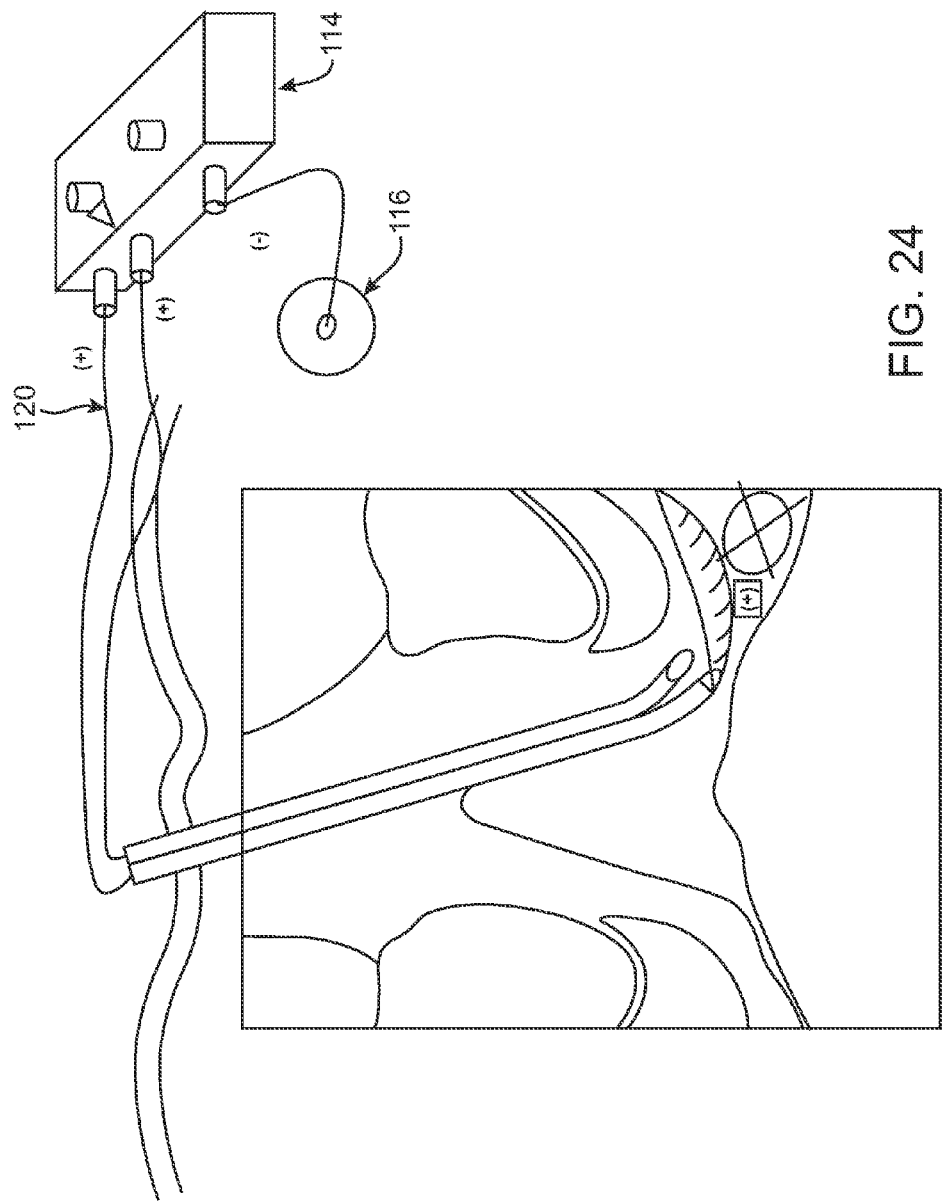

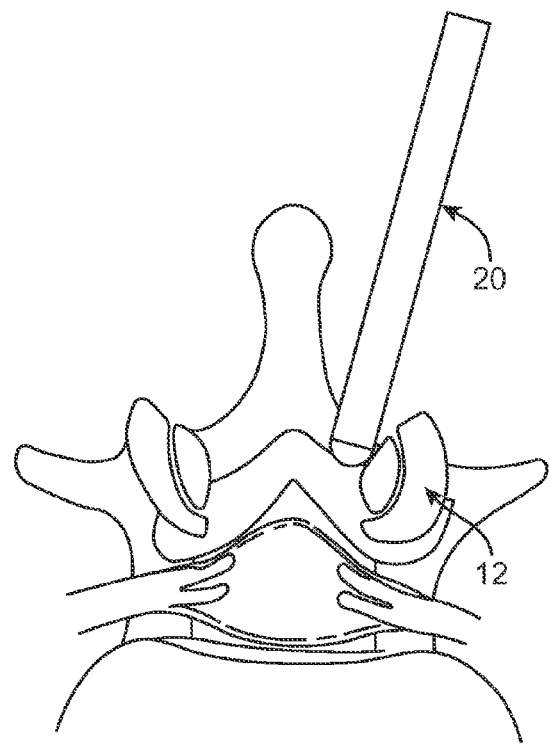
FIG. 37a
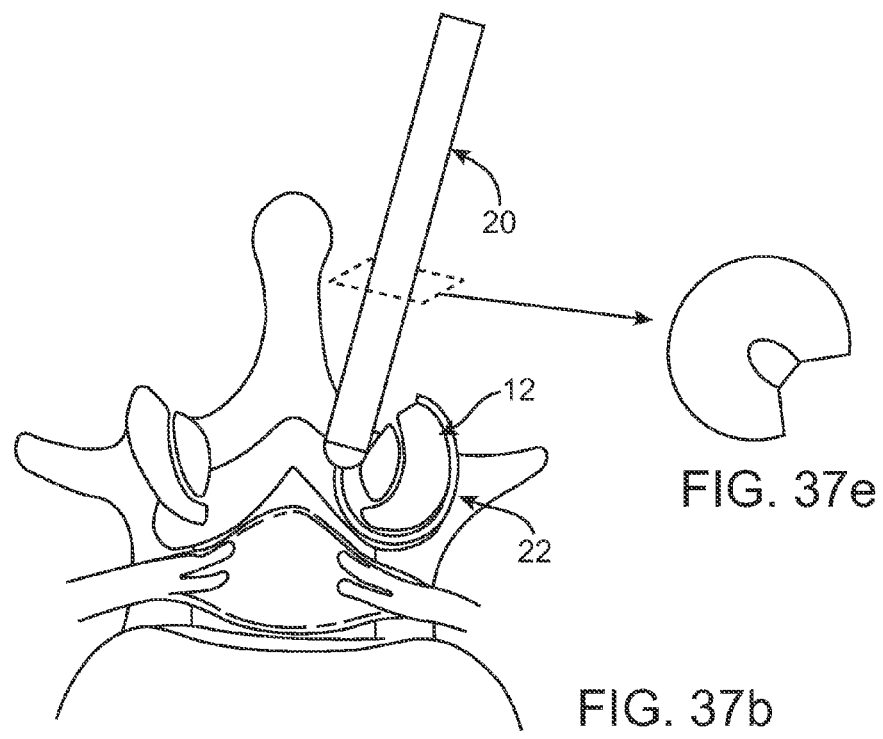
FIG. 37e
FIG. 37b

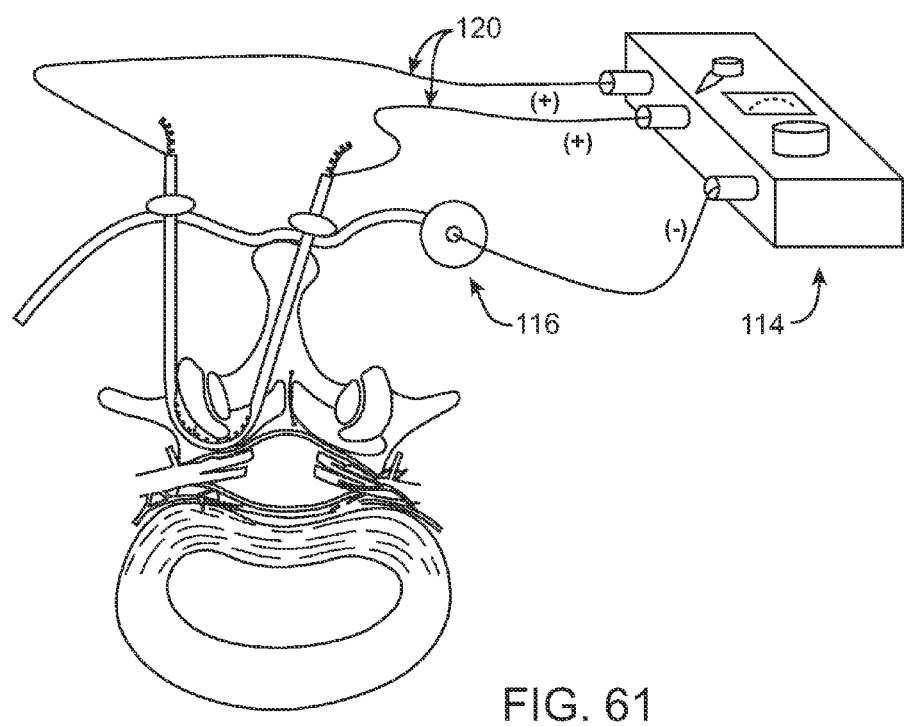
FIG. 61
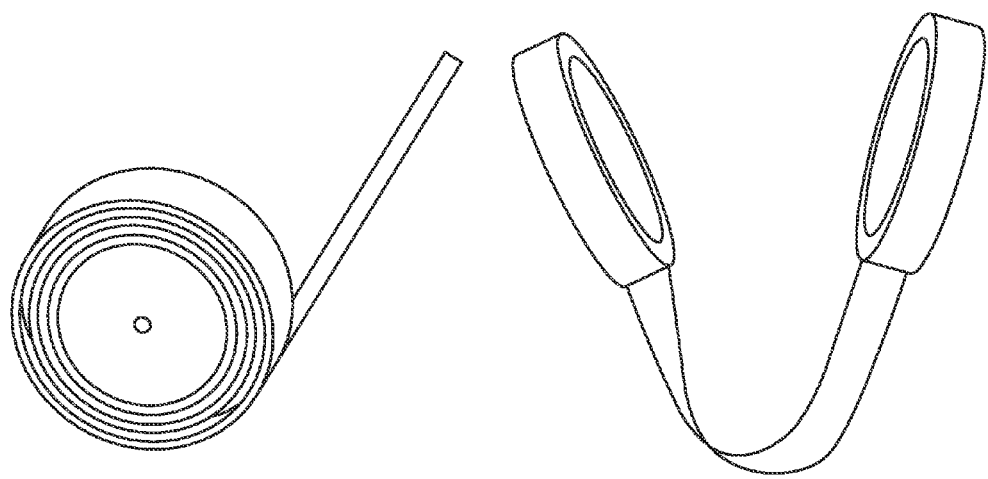
FIG. 62a
FIG. 62b

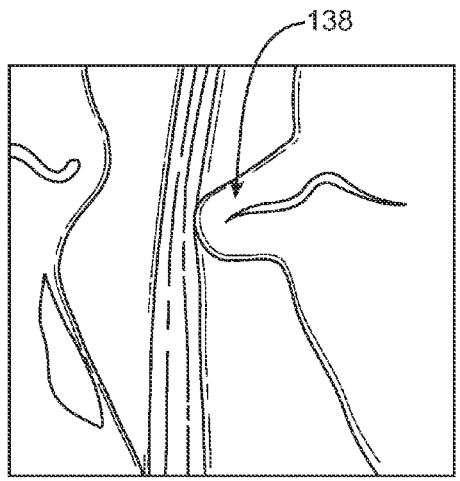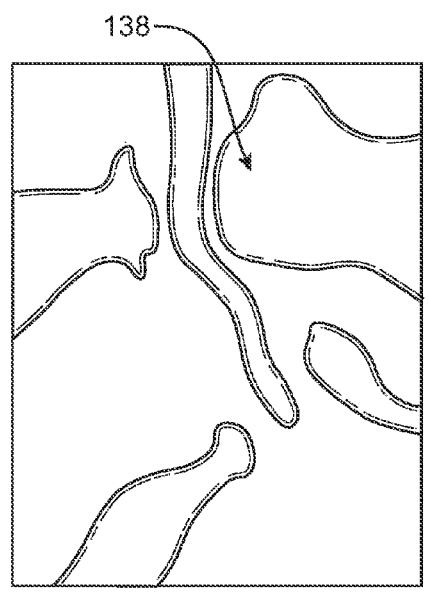
FIG. 81a  FIG. 81b
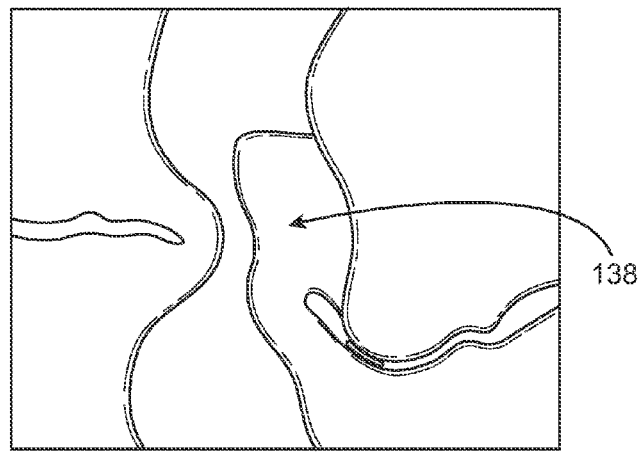
FIG. 81c

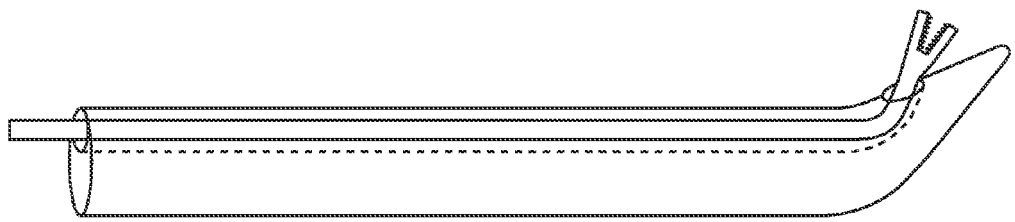
FIG. 96a
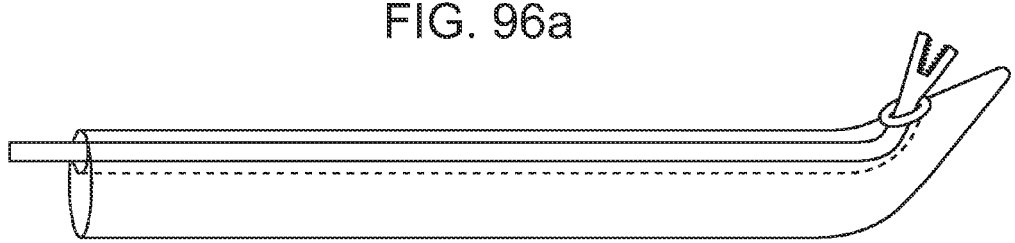
FIG. 96b
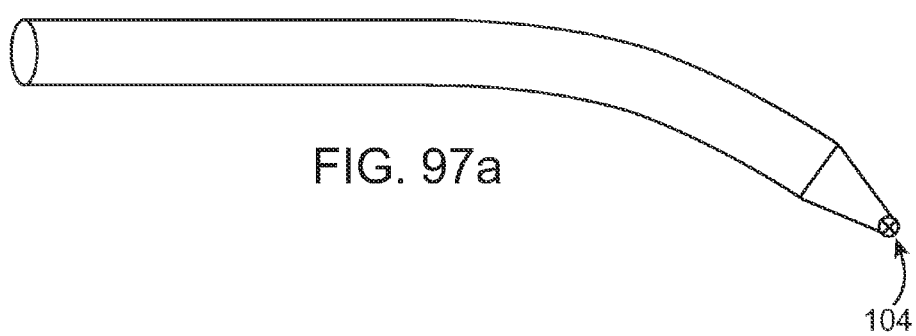
FIG. 97a
FIG. 97b
FIG. 97c

DEVICES AND METHODS FOR TISSUE MODIFICATION

CROSS-REFERENCE TO RELATED APPLICATIONS

This application claims the benefit of U.S. Provisional Application No. 60/619,306, filed 15 Oct. 2004 and U.S. Application No. 60/622,865, filed 28 Oct. 2004, each of which is incorporated by reference herein in its entirety.

FIELD OF THE INVENTION

The present invention relates to methods and apparatus for selective surgical removal of tissue, such as for the treatment of spinal neural and neurovascular impingement, through selective resection, ablation, and remodeling of tissue in the lateral recess, neural foramina and central spinal canal, more particularly, for safely performing lateral recess and neuroforaminal enlargement of the spine.

BACKGROUND OF THE INVENTION

Pathological compression of spinal neural and neurovascular structures is an age-related process, increased in prevalence and severity in elderly populations, with potential congenital anatomic components, that result in back, radicular extremity pain and both neurological (e.g., sensory) and mechanical (e.g., motor) dysfunction. Prevalence is also influenced by congenital spinal anatomy. Disease progression leads to increased neural irritation, impingement, and ischemia, and is frequently accompanied by progressively increased pain, often in conjunction with reflex, sensory and motor neurological deficits.

In the United States, Spinal Stenosis occurs with an incidence of between 4 percent and 6 percent of adults 50 years of age or older, and is the most frequent reason cited for back surgery in patients 60 years of age and older.

Spinal Stenosis often includes neural or neurovascular impingement, which may occur in the central spinal canal, the lateral recesses of the spinal canal, or in the spinal neural foramina. The most common causes of neural compression within the spine are spinal disc disease (collapse, bulging, herniation); ligamentum flavum buckling, thickening and/or hypertrophy; zygapophysial (facet) joint hypertrophy; osteophyte formation; and spondylolisthesis.

Disease progression increases neural irritation, impingement, and ischemia, and is frequently accompanied by progressively increased pain, often in conjunction with reflex, sensory and motor neurological deficits.

Current surgical treatments for Spinal Stenosis include laminectomy (usually partial, but sometimes complete) and/or facetectomy (usually partial, but sometimes complete), with or without fusion. While standard surgical procedures lead to improvements in symptoms for 6 months or more in approximately 60% of cases, there is an unacceptable incidence of long-term complications and morbidity.

Several companies offer tools that facilitate surgical access to the areas of the spine where neural impingement is likely to occur, in order to allow the surgeon to decompress the impinged neural structures through the removal of vertebral lamina, ligamentum flavum, facet complex, bone spurs, and/or intervertebral disc material. These surgical resections are frequently (i.e., occurs in 15% to 20% of cases) accompanied by fusion (arthrodesis). Spinal arthrodesis is performed to fuse adjacent vertebrae and prevent movement of these structures in relation to each other. The fusion is commonly a treatment for pain of presumed disc or facet joint origin, for "unstable spines", and for spines that have been rendered "unstable" by the surgical decompression procedures, as described above. The definition of "spinal instability" remains controversial in current literature.

Spinal arthrodesis may be achieved through various surgical techniques. Biocompatible metallic hardware and/or autograft or allograft bone is commonly secured anteriorly and/or posteriorly in the vertebral column in order to achieve surgical fusion. These materials are secured along and between the vertebral bodies (to restore vertebral height and replace disk material) and/or within the posterior elements, typically with pedicle screw fixation. Autograft bone is often harvested from the patient's iliac crest. Cadaveric allograft is frequently cut in disc shaped sections of long bones for replacement of the intervertebral discs in the fusion procedure.

Critics have frequently stated that, while discectomy and fusion procedures frequently improve symptoms of neural impingement in the short term, both are highly destructive procedures that diminish spinal function, drastically disrupt normal anatomy, and increase long-term morbidity above levels seen in untreated patients.

The high morbidity associated with discectomy may be due to several factors. First, discectomy reduces disc height, causing increased pressure on facet joints. This stress leads to facet arthritis and facet joint hypertrophy, which then causes further neural compression. The surgically-imposed reduction in disc height also may led to neuroforaminal stenosis, as the vertebral pedicles, which form the superior and inferior borders of the neural foramina, become closer to one another. The loss of disc height also creates ligament laxity, which may lead to spondylolisthesis, spinal instability or osteophyte or "bone spur" formation, as it has been hypothesized that ligaments may calcify in their attempt to become more "bone-like". In addition, discectomy frequently leads to an incised and further compromised disc annulus. This frequently leads to recurrent herniation of nuclear material through the expanded annular opening. It may also cause further buckling of the ligamentum flavum. The high morbidity associated with fusion is related to several factors. First, extensive hardware implantation may lead to complications due to breakage, loosening, nerve injury, infection, rejection, or scar tissue formation. In addition, autograft bone donor sites (typically the patient's iliac crest) are a frequent source of complaints, such as infection, deformity, and protracted pain. Perhaps the most important reason for the long-term morbidity caused by spinal fusion is the loss of mobility in the fused segment of the spine. Not only do immobile vertebral segments lead to functional limitations, but they also cause increased stress on adjacent vertebral structures, thereby frequently accelerating the degeneration of other discs, joints, bone and other soft tissue structures within the spine.

Recently, less invasive, percutaneous approaches to spinal discectomy and fusion have been tried with some success. While these less invasive techniques offer advantages, such as a quicker recovery and less tissue destruction during the procedure, the new procedures do not diminish the fact that even less invasive spinal discectomy or fusion techniques are inherently destructive procedures that accelerate the onset of acquired spinal stenosis and result in severe long-term consequences.

Additional less invasive treatments of neural impingement within the spine include percutaneous removal of nuclear disc material and procedures that decrease the size and volume of the disc through the creation of thermal disc injury. While these percutaneous procedures may produce less tissue injury, their efficacy remains unproven.

Even more recently, attempts have been made to replace pathological discs with prosthetic materials. While prosthetic disc replacement is a restorative procedure, it is a highly invasive and complex surgery. Any synthetic lumbar disc will be required to withstand tremendous mechanical stresses and will require several years of development before it will achieve the longevity desired. Further, synthetic discs may not be an appropriate therapeutic approach to a severely degenerative spine, where profound facet arthropathy and other changes are likely to increase the complexity of disc replacement. Like most prosthetic joints, it is likely that synthetic discs will have a limited lifespan and that there will be continued need for minimally invasive techniques that delay the need for disc replacement. Even if prosthetic discs become a viable solution, a simpler, less invasive approach to restoration of functional spinal anatomy would play an important role in the treatment of neural impingent in the spine. The artificial discs in U.S. clinical trials, as with any first generation prosthesis, are bound to fail in many cases, and will be very difficult to revise for patients. The prostheses will, therefore, be best avoided, in many cases. Lumbar prosthetic discs are available in several countries worldwide.

In view of the aforementioned limitations of prior art techniques for treating neural and neurovascular impingement in the spine, it would be desirable to provide methods and apparatus for selective surgical removal of tissue that reduce or overcome these limitations.

SUMMARY OF THE INVENTION

In view of the foregoing, the present invention provides apparatus and methods for selective removal of tissue, e.g., soft tissue and bone, preferably in a minimally invasive fashion. An embodiment of the present invention provides apparatus and methods for safe and selective delivery of surgical tools into to the epidural space; and for apparatus methods that enable safe and selective surgical removal, ablation, and remodeling of soft tissue and bone, preferably in a minimally invasive fashion, with the apparatus delivered into the epidural space. In an important preferred variation of the methods and apparatus are used to treat neural and neurovascular impingement in the spine, through a novel approach to safe and selective enlargement of the pathologically narrow spinal neural foramen, the impinged lateral recess, and central canal.

In a preferred embodiment, the methods and apparatus include the placement of a working backstop or barrier into the epidural space or neural foramina, to a location between the tool positioned for tissue alteration, and adjacent vulnerable neural or vascular structures, to help prevent neural or vascular injury during surgery. In a further preferred embodiment, the methods and apparatus utilize neural stimulation techniques, to enable neural localization, as a means of improving the safety of the procedure.

In one variation of the present invention, an epidural needle may be converted to a working tool in order to resect or remodel spinal tissue, which is enabled by the use of herein described methods and apparatus:

After placement of an epidural needle into the epidural space, a special epidural catheter is threaded through the needle into the epidural space. This catheter apparatus contains a needle tip cover in its distal end, which, after it is converted to an open position in the epidural space, is pulled back over the needle tip, by pulling on the proximal portion of the catheter. The catheter based cover blunts and thereby protects the vulnerable structures of the spine, such as the dura, from the sharp epidural needle tip. With the epidural needle tip covered, the needle may be more safely advanced into the epidural space, in a direction somewhat parallel to the dura, towards the contralateral or ipsilateral lateral recess and neural foramen. The needle may be advanced blindly; with image guidance; or with endoscopic guidance.

The epidural catheter, with the cap or cover for the epidural needle, may or may not contain a rigid or flexible fiberoptic cable. With a fiberoptic element and a clear tip to the catheter, the epidural needle may be converted to an epidural endoscope or "needlescope".

One preferred embodiment of the epidural needle apparatus contains two adjacent lumens ("double barreled"), with a working channel adjacent to the epidural needle. The working channel may be fixed and permanent, or removable, as in with a rail and track connection. A removable working channel, in one embodiment, may be inserted or removed while the tip of the epidural needle remains in the epidural space. The distal beveled opening of the working channel, in a preferred variation, is located proximal to and on the same side of the needle as the epidural needle tip beveled opening faces, facilitating visualization of the working channel tools when a fiberoptic element has been placed in through the epidural needle lumen.

The epidural needle or the working channel of the epidural needle may be a vehicle for insertion of a working backstop or barrier, another apparatus that facilitates safe tissue resection and remodeling in the epidural space. The barrier is a thin flat device that may be delivered into or adjacent to the epidural space or neural foramina, through the needle or working channel, or through an endoscope or open incision. Such a backstop may consist of a flexible, curved, thin and flat piece of material. This barrier will serve to protect neural and neurovascular structures from being damaged during tissue manipulation and resection, because it will be placed between the tissue to be ablated, resected, irritated, manipulated or remodeled, and the vulnerable neural and vascular structures or dura. The tools for tissue resection and ablation will be used on the side of the barrier opposite from the vulnerable neural and vascular structures, which will be safely protected from inadvertent injury.

In one variation of the present invention, a tissue abrasion device is placed, either percutaneously or through an open surgical approach, through the neural foramina of the spine, around the anterior border of the facet joint, and anterior to the ligamentum flavum. The abrasion device alternatively or additionally may be placed through the neural foramen anterior to the facet joint, but through or posterior to the ligamentum flavum. After spinal neuroforaminal placement, the device is used to remove tissues that impinge on the neurovascular structures within the lateral recess and neural foramen, anterior to the facet joint.

The abrasion device may, for example, include a thin belt or ribbon, with an abrasive, shaving, and/or cutting surface, which is placed through the neural foramina and is held firmly against the tissue to be removed. The belt optionally may be placed, at least partially, within a protective sheath or covering, with the treatment area exposed to the abrasive surface of the device somewhat limited to the area where tissue abrasion and removal is desired. The abrasive element may be provided in one or more of a variety of potentially interchangeable shapes, ranging from flat to curved; narrow to wide; or solid to perforated. The abrasive surface may also have various enabling designs, or surface patterns, or coarseness of abrasive material. The apparatus is placed with both free ends of the abrasive element, as well as the ends of the optional protective sleeve or covering, external to the patient for manipulation by a medical practitioner.

When the optional protective sleeve or sheath is provided, both ends of the sleeve may be held under tension, external to the patient, such that the abrasive belt or ribbon may be pulled back and forth through the sleeve without causing significant friction against and/or trauma to adjacent tissues. Initially, both ends of the abrasive ribbon are pulled simultaneously, pulling the device in a posterior and/or lateral direction, thereby bringing impinging spinal tissue in contact with the abrasive and/or cutting surface of the ribbon. When one end of the ribbon is pulled with more force than the other, the ribbon moves in the direction of the stronger pull, while the lesser pull on the opposite end maintains force and creates friction with movement between the abrasive surface and the tissue to be resected.

In an open surgical variation, the ribbon or belt and/or the protective covering or sleeve may be placed through the surgical incision. In a percutaneous variation, the device may be inserted through a needle or over a wire. As with the percutaneous approaches, placement may be aided by the use of image guidance and/or the use of an epidural endoscope.

Once the surgical apparatus has been placed, the medical practitioner may enlarge the lateral recess and neural foramina via cutting, shaving, filing, rasping, sanding, ablating or frictional abrasion, i.e., by sliding the abrasive or cutting surface across the tissue to be resected. Impinging tissue to be targeted for abrasion may include, but is not limited to, lateral ligamentum flavum, anterior and medial facet, and osteophytes. The medical practitioner controls the force and speed of the abrasive surface against the tissue to be removed, while optional covers define the tissue exposed to the abrasive element.

One variation of the abrasive element cover envelopes the abrasive surface and the backside of the belt or ribbon in areas where tissue removal is not intended. A nerve stimulator may be incorporated into the tissue removal surface and/or the protective cover or sleeve in order to verify correct placement and enhance safety by allowing the medical practitioner to ensure that neural tissue is not subject to inadvertent trauma or abrasion during the procedure.

The present invention also describes methods and apparatus that may be used as a compression dressing, after tissue resection or ablation. Following neuroforaminal and lateral recess enlargement, one variation of the compression dressing is placed in a position where it is firmly wrapped against the abraded tissue surface around the facet and ligamentum flavum through the neural foramina. By tightly pressing against treated tissue surfaces, such a device serves to promote desired tissue remodeling; to prevent edema that may lead to impingement on neural or vascular tissue during early healing; to contain debris; to promote postoperative hemostasis; to block scar formation between the raw tissue surfaces and the adjacent neural and vascular structures; to avoid inflammation or irritation to neural and vascular structures from contact with adjacent resected tissue surfaces; and as a mechanism for sustained drug delivery, possibly as a depot, to the operative site post-operatively (e.g. steroids, procoagulants, adhesion barriers). Finally, the dressing would also present a smooth surface towards the nerve root during the immediate post-operative period.

This neuroforaminal compression dressing may, for example, comprise the optional protective sheath, percutaneously held tightly in place against the abraded surface. Alternatively or additionally, a separate percutaneously removable compression dressing may be placed following tissue abrasion, with or without a biodegradable component. In a further alternative embodiment, an entirely biodegradable compression dressing may be placed tightly against the abraded surface, with the compression dressing remaining completely implanted following the procedure.

Safe tissue removal, ablation and remodeling with these methods and devices are further enabled by complementary methods and apparatuses that assist with accurate neural localization. Neural localization will be performed by neural stimulation through electrically conductive materials located within the capped epidural needle tip; within the epidural tools that will be in contact with tissue to be modified; or one or both sides of the working barrier. Neural stimulation will be performed in conjunction with monitoring of the patient for sensory and/or motor response to the electrical impulses.

Said backstop may also contain neural localization capabilities, including a conductive element on the working side and/or the non-working side. The conductive element may be used to ensure that the neural and their adjacent vascular structures are on the non-working side of the barrier. In the instance that the barrier is placed through the lateral recess or neural foramina, appropriate low intensity electrical stimulation on the non-working surface should result in the stimulation of sensory or motor nerves in the patient's extremity, while appropriate electrical conduction on the working surface should result in no neural stimulation. Neural stimulation may be monitored by monitoring somatosensory-evoked potentials (SSEPs), motor-evoked potentials (MEPs), and/or by looking for visual signs of muscular contraction within the extremities. (Somatosensory evoked potentials (SSEPs) are non-invasive studies performed by repetitive, sub-maximal, electrical stimulation of a sensory or mixed sensory and motor nerve. In response to the nerve stimulation the brain generates cerebral action potentials (electrical waves), that can be measured and recorded over the scalp and spine with surface electrodes. In many cases, needle electrodes are used for intraoperative SSEP monitoring, as they require less current, and reduce artifact. The recorded response is a series of waves that reflect activation of neural structures.) SSEP, SEP, MEP or EMG feedback may be monitored and/or recorded visually, or may be monitored audibly, potentially conveying quantitative feedback related to the volume or frequency of the auditory signal (e.g., a Geiger counter type of quantitative auditory feedback). Intensity of signal or stimulation may be monitored and used to localize the nerve during placement, as well.

For example, the surgeon may use the neural stimulator to ensure that there is not stimulation of vulnerable neurons on the working side of the barrier, prior to initiating tissue manipulation with the working tools. For example, with the barrier in position in the lateral recess or neural foramina, the surgeon may send electrical current first along the working side of the barrier, then along the backside of the barrier. Low level stimulation of the working side would be expected to result in no neural stimulation, while the same stimulation on the backside of the barrier would be expected to stimulate dorsal roots, nerve roots, or ganglia.

Neural localization may be further enabled by the addition of surgical instruments (e.g. cautery devices, graspers, shavers, burrs, probes, etc.) that are able to selectively stimulate electrically while monitoring nerve stimulation in similar fashions. Quantification of stimulation may enable neural localization. For instance, one might use a calibrated sensor input that recognizes stronger stimulation as the device is closer the neural structures. For added safety, a surgical device may be designed to automatically stimulate before or during resection, and may even be designed to automatically stop resection when nerve stimulation has been sensed.

A method for modifying spinal anatomy is disclosed. The method includes delivering a surgical apparatus to an epidural space and surgically altering tissues that impinge neural or vascular structures in the lateral recess, neural foramina or central canal of the spine with the apparatus. Surgically altering tissues can include ablating tissue, resecting tissue, removing tissue, abrading tissue, retracting tissue, stenting tissue, retaining tissue, or thermally shrinking tissue. Surgically altering tissues can additionally include enlarging the lateral recess, neural foramina or central canal of the spine.

Delivering the surgical apparatus to an epidural space can include delivering an epidural needle to the epidural space, and enlarging the lateral recess, neural foramina or central canal of the spine can include focally altering tissue with tools delivered through the epidural needle. Delivering the surgical apparatus to an epidural space also can include delivering an epidural needle to the epidural space, and enlarging the lateral recess, neural foramina or central canal of the spine also can include focally altering tissue with tools delivered through a working channel disposed adjacent to the epidural needle.

Delivering the surgical apparatus can include converting the epidural needle to an endoscope within the epidural space. Delivering the surgical apparatus to an epidural space also can include delivering a working endoscope to the epidural space, and enlarging the lateral recess, neural foramina or central canal of the spine can also include focally altering tissue with tools delivered through the working endoscope. Delivering the surgical apparatus can also include converting the epidural needle into a blunt tipped instrument after placement of the needle's tip within the epidural space. Converting the epidural needle can also include threading an epidural catheter through the epidural needle into the epidural space, and covering the needle's tip with an epidural needle cover delivered via the catheter.

Delivering the surgical apparatus can also include converting the epidural needle into an endoscope via a visualization element disposed within the epidural catheter. Delivering the surgical apparatus can include infusing fluid into the epidural space to improve visualization. Delivering the surgical apparatus can include inserting a removable working channel alongside the surgical apparatus. Delivering the surgical apparatus can include inserting a distal tip of a dual lumened epidural needle into the epidural space and using at least one of the dual lumens as a working channel for the delivery of instruments into the epidural space. Delivering the surgical apparatus can include inserting an instrument chosen from the group consisting of a tissue cauterization tool, a tissue laser device, a radiofrequency delivery device, a ronguer, a tissue grasper, a tissue rasp, a probe, a bone drill, a tissue shaver, a burr, a tissue sander and combinations thereof through the surgical apparatus.

Delivering the epidural needle can include inserting the epidural needle to a position with a tip of the needle in proximity to where treatment will be directed. Delivering the epidural needle can include inserting the epidural needle at an interspace below the level of the spine where the treatment will be directed.

Delivering surgical apparatus can include delivering the apparatus via an open surgical route. Delivering the epidural needle can include delivering the needle via a posterior, interlaminar percutaneous route. Delivering the epidural needle can include delivering the needle via a posterior, translaminar, percutaneous route. Delivering the epidural needle can include delivering the needle via a posterior, midline, interspinous, percutaneous route. Delivering the epidural needle can include delivering the needle via a percutaneous route through the neural foramen from its lateral aspect. Enlarging can include placing a mechanical barrier or backstop between tissue to be resected and adjacent neural or vascular structures. The barrier can be steerable.

The method of modifying the spinal anatomy can include confirming proper placement of the surgical apparatus. Confirming proper placement can include confirming proper placement with a nerve stimulator. Confirming proper placement with a nerve stimulator further comprises confirming proper placement with stimulation leads placed on a tissue remodeling side of the surgical apparatus. The method of modifying the spinal anatomy can include confirming proper placement of the surgical apparatus or barrier with a nerve stimulator having stimulation leads placed on a tissue remodeling side of the barrier or on a back side of the barrier.

The method of modifying the spinal anatomy can include monitoring nerve stimulation with the nerve stimulator via somatosensory evoked potentials (SSEPs). The method of modifying the spinal anatomy can include monitoring nerve stimulation with the nerve stimulator via motor evoked potentials (MEPs). The method of modifying the spinal anatomy can include monitoring nerve stimulation with the nerve stimulator via motor evoked patient movement. The method of modifying the spinal anatomy can include monitoring nerve stimulation via verbal patient sensory response to the nerve stimulator.

The method of modifying the spinal anatomy can include monitoring enlargement via imaging. The method of modifying the spinal anatomy can include surgically altering the tissues under fluoroscopic imaging, MRI imaging, CT imaging, ultrasound imaging, radiological imaging, surgical triangulation, infrared or RF surgical triangulation.

The method of modifying the spinal anatomy can include placing an element that provides tissue compression of surgically remodeled tissue or bone surface in order to enlarge the neural pathway or foramina post-surgical enlargement. The method of modifying the spinal anatomy can include placing an element that provides tissue compression and retention in order to remodel tissue or bone surface in order to enlarge the neural pathway or foramina de novo. Placing the element can include placing the element using a percutaneous technique via the epidural space, through a neural foramen at a level to be treated for spinal stenosis, and around a facet complex or a lamina adjacent to the facet complex. The method of modifying the spinal anatomy can include tightening the element to a determined tension. Placing the element can include placing an element having a posterior anchor that is a cord or tie looped through a hole that has been drilled in the cephalad lamina of the immediately adjacent vertebrae. The method of modifying the spinal anatomy can include tensioning the element to a determined level via a tension gauge or other measurement device element holding tension against the tissue to be remodeled.

The method of modifying the spinal anatomy can include releasing a biologically active material for the purposes of decreasing inflammation, or promoting remodeling of soft tissue or bone growth from the element.

Apparatus for focal tissue alteration are disclosed herein. The apparatus have an element configured for placement into an epidural space, and surgical tools configured for delivery through the element into the epidural space to remodel spinal anatomy that impinges upon neural, neurovascular or tendon structures. The element can include an epidural needle, and wherein the surgical tools further comprise a tissue remodeling device configured for placement via the epidural needle.

The epidural needle can be configured for placement into the epidural space via an approach chosen from the group consisting of a posterior interspinal midline approach, a posterior paramedian interlaminar approach, a posterior translaminar paramedian approach through a hole in the lamina, a neural foramina approach around an anterior border of a facet joint, and combinations thereof. The epidural needle can include two adjacent lumens, the second lumen configured to act as a working channel for the delivery of the surgical tools into the epidural space.

The apparatus can have an epidural catheter configured to convert the epidural needle into a blunt tipped instrument via an epidural needle tip cover that may be opened and then pulled back to cover the needle's tip. The epidural catheter can have a fiberoptic cable for visualization. The apparatus can have an insertable and removable working channel for tool access configured for placement alongside the needle.

The tissue remodeling device can be chosen from the group consisting of a tissue cauterization tool, a tissue laser device, a radiofrequency delivery device, a ronguer, a tissue grasper, a tissue rasp, a probe, a bone drill, a tissue shaver, a burr, a tissue sander, and combinations thereof.

The surgical tools can produce nerve stimulation. The apparatus can have a device for monitoring neural stimulation to identify when a working surface of the surgical tools is in close proximity to vulnerable neural tissue during tissue remodeling.

An apparatus for protecting adjacent structures during remodeling of spinal anatomy that impinges upon neural, neurovascular or tendon structures is disclosed. The apparatus has a mechanical barrier configured for placement between tissue to be resected and the adjacent structures. The mechanical barrier can be configured for insertion through an open incision. The mechanical barrier can be configured for insertion through a working channel of an endoscope.

The apparatus can be configured for use with a visualization element. The visualization element can be chosen from the group consisting of an epidural endoscope, a fluoroscope, ultrasound, XRay, MRI and combinations thereof. The apparatus can have a nerve stimulator to facilitate proper placement of the barrier. A conductive element can be included on a tissue modification side of the barrier or on a backside of the barrier to facilitate nerve localization. A working surface of the tissue remodeling device can have neurostimulation capabilities, thereby allowing for a positive and negative control in localizing neural tissue prior to tissue removal.

The apparatus can include a monitoring technique for monitoring electrical nerve stimulation. The monitoring technique can be chosen from the group consisting of SSEPs (somatosensory evoked potentials); MEPs (motor evoked potentials); EMG; verbal inquiries of the patient's sensory experience to the electrical stimulation; visual techniques, mechanical techniques, tactile techniques monitoring neuro muscular stimulation and movement, and combinations thereof.

The apparatus can include an element configured to provide tissue compression against surgically remodeled tissue or bone surface in a neural pathway or foramina post-enlargement. The element is configured for percutaneous placement via the epidural space, through the neuroforamen at the level to be treated for spinal stenosis, and around the facet complex or the lamina adjacent to the facet complex. The element is configured to release a biologically active material for the purposes of decreasing inflammation, or promoting remodeling of soft tissue or bone growth.

The apparatus can be configured for tightening to a determined tension for purposes of relieving spinal stenosis. The element can include a posterior anchor having a cord or tie looped through a hole that has been drilled in the cephalad lamina of the immediately adjacent vertebrae. Tension of the element is configured to be set at a determined level by a tension gauge, or other measurement device element holding tension against tissue to be remodeled.

The apparatus can have a neuro foraminal compression element configured to retract and hold pressure on spinal tissue when placed under tension, in order to relieve pressure on impinged neural and vascular structures and promote tissue remodeling. The apparatus can have a tensioning device for the neuro foraminal compression element configured to secure two ends of the element together at a posterior aspect of the vertebral lamina at a desired tension by pulling the element to the desired level of tension prior to locking the opposite ends of the element together at said tension.

The apparatus can have a tensioning device configured to tighten a loop formed by the neuro foraminal compression element around the facet joint complex, within the lateral aspect of the lamina, and configured to tighten the compression element across a locking or crimping element to a specified tension, pulling the ligamentum flavum posteriorly in the spinal canal, in the lateral recess and in the neural foramen.

The apparatus can have a tensioning device configured to tighten a loop formed by the neural foraminal compression element around the lamina, close to a facet joint complex, within a lateral aspect of the lamina, and configured to tighten the compression element across a locking or crimping element to a specified tension, pulling the ligamentum flavum posteriorly in the spinal canal, in the lateral recess and in the neural foramen.

At least one free end of the neural foraminal compression element can be configured for subcutaneous placement to facilitate future removal of the element. The compression element can be biodegradable.

The compression element can contain a therapeutic agent chosen from the group consisting of medications, bioactive compounds, steroids, depot steroids, anti-inflammatories, and combinations thereof. The agent can be configured for immediate release. The agent can be configured for sustained local delivery.

A method of altering bone or soft tissue in a patient is disclosed. The method includes placing a tissue abrasion device through tissue to be altered, holding the tissue abrasion device under tension to bring an abrasive surface of the device firmly against the tissue to be altered, and sliding the abrasive surface of the abrasive element against the tissue to be altered, thereby altering bone or soft tissue immediately adjacent to the abrasive surface. Altering can include abrading, removing, or remodeling. Placing the tissue abrasion device through tissue to be altered can include placing the device through spinal tissue that impinges on neural, neurovascular or ligamentous structures in the patient's spine. Placing the tissue abrasion device can include placing the tissue abrasion device through a neural, neurovascular, or ligamentous pathway within the patient's spine, holding the tissue abrasion device under tension to bring the abrasive surface against tissue within the pathway, and where sliding includes enlarging the pathway via frictional abrasion of the tissue. Placing a tissue abrasion device through the pathway can include placing the tissue abrasion device through neural foramina of the patient's spine and around the anterior border of a facet joint. Placing the tissue abrasion device through neural foramina of the patient's spine and around the anterior border of a facet joint can include placing the device via a route chosen from the group consisting of an open surgical approach, a percutaneous approach, a posterior percutaneous approach, an interlaminar percutaneous approach, a translaminar percutaneous approach, an interspinous percutaneous approach, through the neural foramen from a lateral direction, and combinations thereof. Placing the tissue abrasion device can include placing the device within a protective sheath or cover.

The method can include altering spinal tissues that impinge on neural, neurovascular, or ligamentous structures in the patient's spine.

Enlarging the pathway can include enlarging a diseased pathway within the patient's spine.

Holding the tissue abrasion device under tension against tissue within the pathway can include placing an abrasive surface of the tissue abrasion device against tissue chosen from the group consisting of an anterior surface of facet joint capsule, a medial surface of facet joint capsule, a superior articular process of the facet joint, ligamentum flavum, tissues attached to ligamentum flavum, extruded spinal disc material, scar tissue, and combinations thereof.

Sliding the tissue abrasion device against the tissue can include sliding the abrasive surface of the tissue abrasion device against the tissue. Sliding the abrasive surface can include enlarging the lateral recess, neural foramina or central spinal canal via frictional abrasion. Sliding the abrasive surface can include preferentially abrading tissue chosen from the group consisting of ligamentum flavum, bone spurs, facet capsule, superior articular process, extruded spinal disc material, scar tissue and combinations thereof that impinge on neural or vascular structures.

The method can include confirming proper placement of the tissue abrasion device. Confirming proper placement of the device can include confirming proper placement with a nerve stimulator. Confirming proper placement with a nerve stimulator can include confirming proper placement with a nerve stimulator having stimulation leads placed at a location chosen from the group consisting of a non-abrasive side of the tissue abrasion device, a back side of a protective sleeve or cover placed over the tissue abrasion device, an abrasive side of the tissue abrasion device, a working side of the tissue abrasion device, and combinations thereof. Confirming proper placement can include confirming placement via a modality chosen from the group consisting of fluoroscopic, MRI, CT, infrared, ultrasound imaging, surgical triangulation, and combinations thereof.

The method can include monitoring nerve stimulation via somatosensory-evoked potentials (SSEPs) with the nerve stimulator. The method can include monitoring nerve stimulation via motor-evoked potentials (MEPs) with the nerve stimulator. The method can include monitoring nerve stimulation via verbal patient sensory response to the nerve stimulator.

The method can include replacing the tissue abrasion device with a compression element that is held against altered tissue or bone.

Apparatus for the removal of impinging soft tissue or bone within a patient are disclosed. The apparatus can have a tissue abrasion device configured for placement through impinged tissue pathways. The tissue abrasion device can have an abrasive surface configured for placement adjacent to the impinging tissue. The impinged tissue pathways can have pathways chosen from the group consisting of neural pathways, neurovascular pathways, ligamentous pathways, and combinations thereof. The tissue abrasion device can be configured for the removal of spinal structures that impinge neural or neurovascular tissues within the patient, and wherein the tissue abrasion device is configured for placement through neural foramina of the patient's spine and around the anterior border of a facet joint.

The apparatus can have a protective cover disposed about the tissue abrasion device, where the protective cover is configured to limit exposure of an abrasive surface of the device to areas where tissue removal is desired. The apparatus can have a nerve stimulator in communication with the tissue abrasion device to facilitate proper placement of the device.

The apparatus can have a conductive element disposed on an abrasive surface of the device to enable nerve localization by sending a small electrical current through the conductive element.

The apparatus can have an epidural needle, where the tissue abrasion device is configured for placement through the epidural needle.

The apparatus can have a visualization element for direct visualization of the neural foramina. The apparatus can have a neural foramina compression element.

The compression element can be configured to promote hemostasis and desired tissue remodeling during healing. The element can be configured to be left in place after being secured with adequate tension against tissue abraded with the tissue abrasion device. The compression element can be configured to protect a tissue surface abraded with the device. The compression element can be configured to prevent adhesions during healing. The compression element can be configured to protect vulnerable structures adjacent to tissue abraded with the tissue abrasion device from an inflammatory response triggered by tissue abrasion.

The tissue abrasion device can be configured for placement in front of, across, and then behind tissue to be abraded, such as through a naturally occurring or artificially created anatomical foramen or tissue pathway. The abrasive surface can be disposed on all or part of one side of the tissue abrasion device. The abrasive surface can be disposed on an element chosen from the group consisting of a length of ribbon, strap, cable, belt, cord, string, suture, wire and combinations thereof. The ends of the device can be configured for manual grasping. The apparatus can have a handle to which ends of the device are attached for manual grasping. The device can be configured for attachment to an electromechanical power-driven device.

The device can be configured to be placed under tension in order to bring the abrasive surface into contact with tissue to be removed. The abrasive surface can be configured to be pulled against tissue to be removed. The abrasive device can have multiple abrasive elements with different abrasive surfaces, configured for interchangeable use. The multiple abrasive elements can have varying grades of abrasive material. The multiple abrasive elements can have different grooves, patterns of grooves, or material patterns on the abrasive surface to facilitate preferential abrasion of tissue at desired locations. The patterns of grooves can have diagonal parallel grooves that preferentially move the abrasive element towards one direction on the surface being abraded as the abrasive element is pulled in one direction, and towards an opposing direction as the abrasive element is pulled in a second direction. The multiple abrasive elements can have different shapes that guide the extent and location of tissue removal.

The apparatus can be configured to carry debris away from the site of tissue removal.

The tissue abrasion device can vary in profile along its length. The tissue abrasion device can have openings that facilitate passage of debris behind the device for storage or removal.

The apparatus can have a monitor for monitoring electrical nerve stimulation with the nerve stimulator. The monitor can be configured to monitor a feedback chosen from the group consisting of SSEPs, MEPs, EMG, verbal communication of patient sensation, visual monitoring, mechanical monitoring, tactile means, monitoring of neuromuscular stimulation and movement, and combinations thereof.

The compression element can be biodegradable. The compression element can contain a therapeutic agent configured for delivery to abraded tissue or adjacent neural and neurovascular structures. The therapeutic agent can be a medication, bioactive compound, steroid, depot steroid, anti-inflammatory, adhesion barrier, procoagulant compound, or combination thereof.

The protective cover can be attached, external to the patient, to a suspension system that includes elements to firmly and individually grasp each end of the cover and hold it in position under tension against the tissue surface to be abraded, with an open portion of the cover exposing the abrasive element directly over tissue to be abraded. The protective cover can be configured to protect a non-abrasive side of the tissue abrasion device. The protective cover can have channels along its lateral aspects for the insertion and sliding of the tissue abrasion device. The protective cover can include channels along its lateral aspects for the insertion and sliding of a second protective cover configured for placement between an abrasive surface of the tissue abrasion device, and tissue adjacent to tissue to be abraded with the abrasive surface.

Finally, the present invention also describes methods and apparatus that promote tissue remodeling, separate from the tissue resection or ablation. These devices tightly wrap, retract, or hold in position, under tension, impinging tissues within the spinous posterior elements.

It is expected that the apparatus and methods of the present invention will facilitate a minimally invasive approach to the selective elimination of pathological spinal tissue, thereby enabling symptomatic relief in patients suffering from spinal stenosis.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 3 a, b, c are sagittal views through a patient's spine, illustrating a prior art method for epidural needle insertion, a loss of resistance method;

FIGS. 12 d, e are schematic side views of an epidural portal over needle apparatus, as shown in FIGS. 12 a, b, c; with a distal anchor engaged anterior to the ligamentum flavum, when the portal has been inserted over the needle, into the epidural space;

FIG. 23b is a frontal view from above;

FIG. 23c is a front view;

FIG. 23d is a frontal view of the working backstop or barrier apparatus folded for compact delivery;

FIG. 24 is a cross-sectional view through a patient's spine that illustrates a methods and apparatuses for providing neural stimulation and neural localization, within a working backstop or barrier, and/or within a tool (a bone burr placed djacent to a spinal bone spur in the lateral recess, in this illustrative example), for safety in tissue resection, abrasion or remodeling;

FIGS. 37a-e are cross-sectional views through a patient's spine, illustrating another variation of the method and apparatus of FIGS. 25-32;

FIG. 61 is a schematic cross-sectional view through a patient's spine, illustrating a method and apparatus for achieving neural localization prior to or during use of the tissue removal apparatus;

FIG. 62 are schematic views of additional apparatus, showing a spool or reel to reel configuration of a portion of the device that may be utilized for selective surgical removal of tissue;

FIG. 81 are sagittal cryosection images through 3 cadaveric spines (images courtesy of Wolfgang Rauschning, Md.) that illustrate pathological anterior bulging and "buckling" of the ligamentum flavum, encroaching on the spinal canal or lateral recess, a frequent contributing factor in spinal stenosis. In circumstances when similarly protruding ligamentum flavum impinges neural and neurovascular structures in the spinal canal, lateral recess, or neural foramina, then retraction of said ligaments, as in FIGS. 79 and 80 may be beneficial to the patient;

FIGS. 88-93 are schematic lateral views of additional apparatus that may be utilized for visualization in the epidural space, enabling the selective surgical removal of tissue;

FIG. 88 illustrate an embodiment of an endoscope in a clear tipped cannula;

FIG. 89 illustrate an embodiment of a 0-degree endoscope rotated in unison with a curved, clear tipped cannula;

FIG. 90 illustrate an embodiment of a 30-degree endoscope rotated separately inside of a clear tipped cannula;

FIG. 92 illustrate an embodiment of a clear tipped cannula with a flexible neck;

FIG. 93 illustrates an embodiment of an endoscope with a built-in clear cover (e.g., a combination device embodiment);

FIGS. 94-99 are schematic lateral views of similar apparatus for visualization in the epidural space, along with additional method and apparatus that enable the safe placement and use of tools for selective surgical ablation, resection, abrasion and remodeling of tissue;

FIG. 94 illustrate various embodiments of a clear tipped cannula with a free adjacent tool;

FIG. 95 illustrate various embodiments of a clear tipped cannula with an attached adjacent tool;

FIG. 96a illustrates an embodiment of a clear tipped cannula with a working channel for a tool;

FIG. 96b illustrates an embodiment of a clear tipped cannula with a nerve stimulator at a working channel exit;

FIG. 97 illustrate various embodiments of cannulas with a nerve stimulator at the tip (e.g., EMG sensors peripherally placed);

FIG. 98 illustrate various embodiments of a clear tipped cannula with a nerve stimulator at a tip of the free tool; and FIG. 99 illustrate various embodiments of a clear tipped cannula with a nerve stimulator at a tip of the free or attached tool.

DETAILED DESCRIPTION

Figure 1:
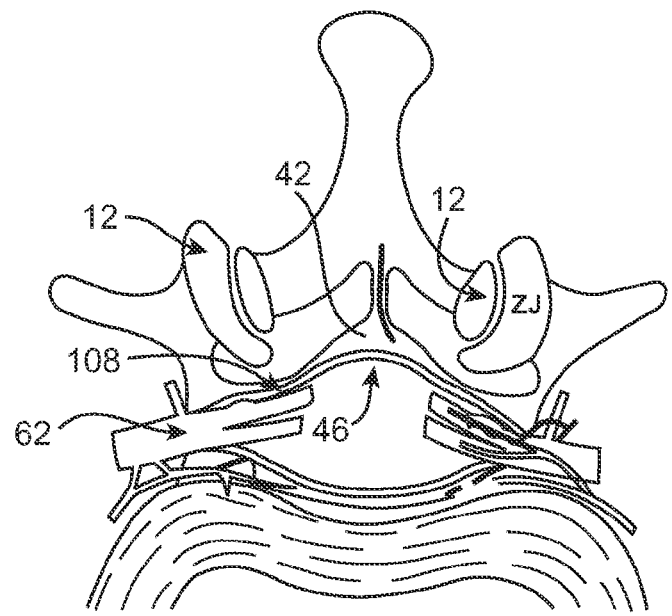
FIG. 1 is a cross section through the posterior aspect of the lumbar spine.

The present invention relates to methods and apparatus for the selective surgical removal or alteration of tissue that impinges upon spinal neural or vascular structures, with particular attention towards avoiding injury to the affected or adjacent neural and neurovascular structures. More particularly, a preferred embodiment of the present invention relates to methods and apparatus for lateral recess 108 and neural foraminal enlargement of the spine, in cases of neurovascular impingement, through a novel approach to selective and safe enlargement of the pathologically narrow spinal neural foramen 110, impinged lateral recess 108 and/or compromised central spinal canal. Tissues that impinge the spine's central canal, lateral recess 108, and neural foramen 110 may include, but are not limited to, ligamentum flavum 10; bone spurs or ligamentous calcifications; localized disc extrusions; enlarged facet joint complex 12, facet capsule, and superior articular processes; and scar tissue or adhesions.

The variations of the invention designed to treat spinal stenosis are summarized in this paragraph, and described in greater detail in the paragraphs that follow. The methods begin with insertion of an epidural needle 2 apparatus, which is converted, after placement in the epidural space, from a sharp tipped instrument, into a blunt tipped tool. The blunt tool is manipulated within the epidural space. Accurate tool manipulation may be facilitated with the use of image guidance; direct vision via an accompanying epidural endoscope; or direct vision when the instrument itself is given endoscopic function. The same blunt tipped epidural instrument may have an attached fixed or removable working channel. An additional apparatus of the current invention, a working backstop or barrier 96 that serves to protect adjacent vulnerable structures during the procedure, may subsequently be inserted into the epidural space, as well as through the neural foramina, through the needle or endoscope or an adjacent working channel. Safe resection, ablation, and remodeling may be further ensured through integration into the invention of electrical neural stimulation and monitoring for localization, optionally available through nerve stimulation functionality in the epidural instrument; in the working tools used through the needle or working channel; and/or in either or both sides of the working backstop 96. Finally, further variations of the device and method enable the surgeon to remodel stenotic spinal anatomy, either after tissue resection, cutting, or abrasion or as stand-alone procedures, through the placement of devices for holding, retracting or retaining anatomic structures away from vulnerable neural and neurovascular structures within the posterior elements of the spine.

Figure 2:
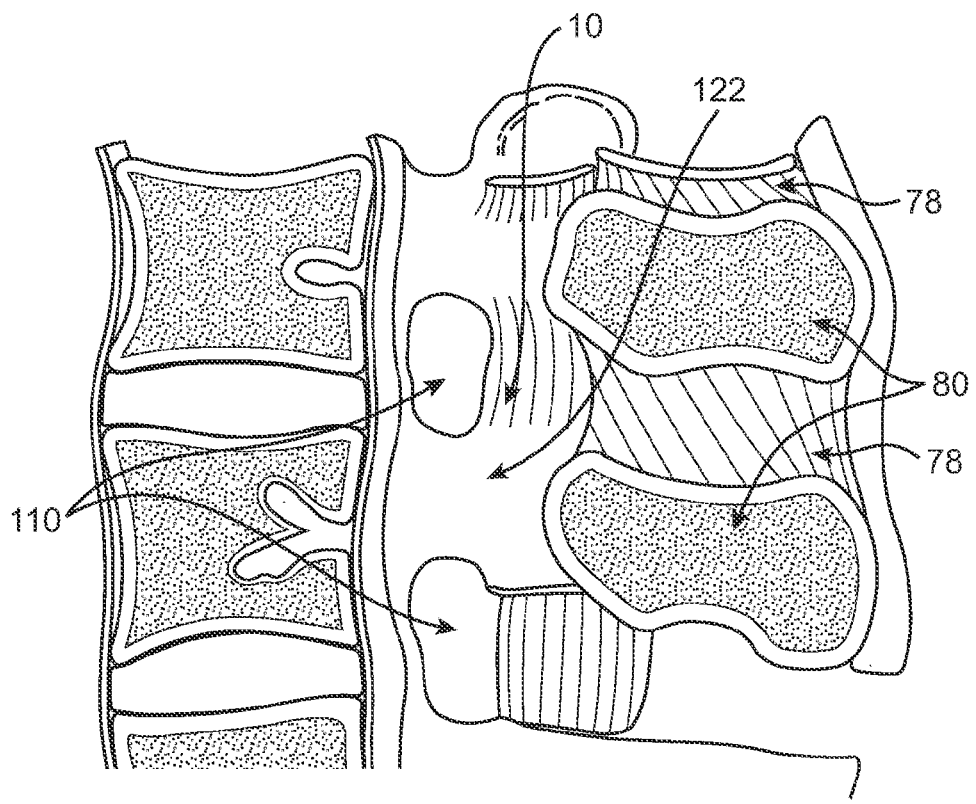
FIG. 2 is a sagittal section through the lumbar spine.

FIG. 1 shows the posterior elements of the spine in axial cross section. The epidural space 42 in the spine is consistently more accessible in its posterior most aspect, a fat filled zone most popular for safe epidural needle 2 placement, posterior to the dura mater 46. The dura 46 covers and contains the central neural elements of the spine, including the spinal cord, cauda equina 140, nerve roots 62, and spinal fluid. FIG. 2 illustrates the spine in sagittal section. FIGS. 1 and 2 show two of the most important anatomic structures involved in the impingement of neural and neurovascular tissue in spinal stenosis—the ligamentum flavum 10 and the facet joint complex 12. FIG. 2 illustrates spinous processes 80.

Figure 3A:
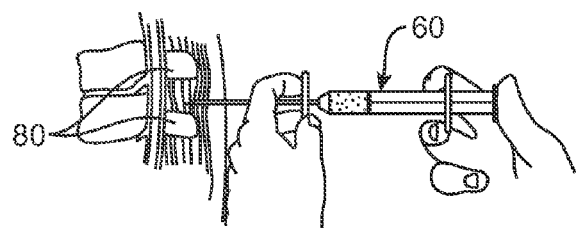
FIG. 3a illustrates a needle inserted to an interspinal ligament.
Figure 3B:
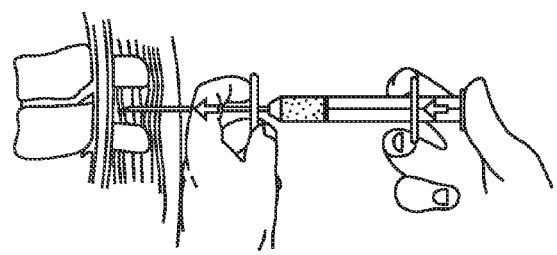
FIG. 3b illustrates constant pressure applied on the syringe plunger.
Figure 3C:
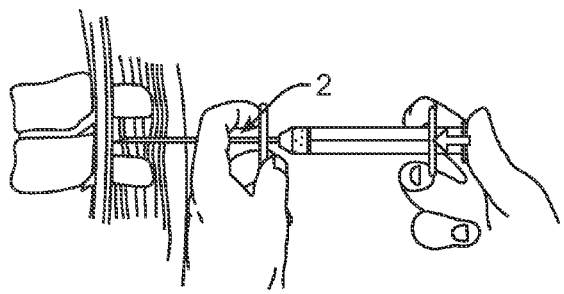
FIG. 3c illustrates saline injected into the epidural space.

For posterior approaches to the lateral recess 108 and neural foramen 110, the needle 2 is inserted at or one level below the spinal interspace where tissue abrasion and removal is desired. The epidural needle 2 may be inserted into the epidural space 42, midline, ipsilateral, or contralateral to the area where the spinal canal, lateral recess 108 and/or neuroforaminal stenosis or impingement is to be treated. Referring now to FIG. 3, a prior art method for epidural needle 2 insertion is shown, comprising a standard loss-of-resistance technique. Needle based device placement may be approached from either the medial or the lateral side of the neural foramen 110. FIG. 3 illustrate a midline interspinous approach to the posterior epidural space 42. Using this technique, a large bore (e.g. 12 to 18 gauge) epidural needle 2 is inserted into interspinal ligaments, and is directed towards the posterior epidural space 42, while fluid (e.g. sterile saline) or air is compressed within the syringe 60, meeting resistance to injection. Upon entry of the needle tip into the epidural space 42, perhaps through the ligamentum flavum 10, there is a manually perceptible "loss of resistance" to the continued pressure on the plunger of the syringe 60, as the compressed fluid or air easily enters the epidural space 42, without resistance, signifying correct needle tip position (i.e., placement). The epidural space has a slight negative pressure.

Figure 4:
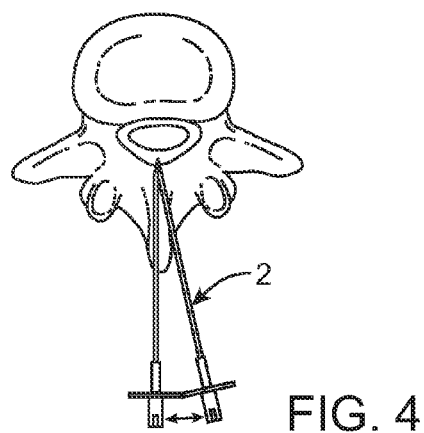
FIG. 4 is a cross-sectional view through a patient's spine, illustrating two prior art variations of the method of FIGS. 3 a, b, c.
Figure 5:
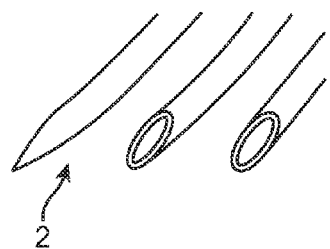
FIG. 5 is an illustration of standard Touhy epidural needle tips.
Figure 71A:
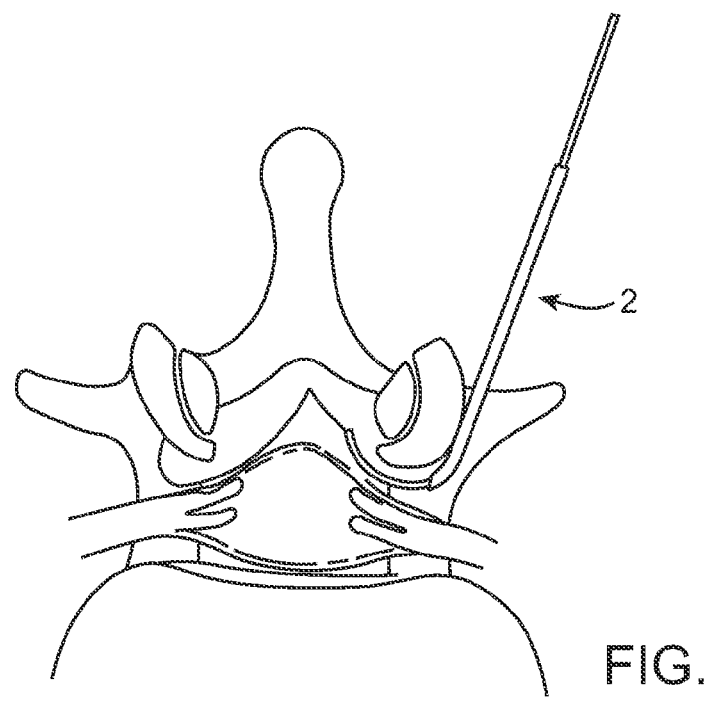
FIG. 71 are schematic cross-sectional views through a patient's spine illustrating a posterior lateral approach to placement of the spinal compression, retraction or retention apparatuses.
Figure 71B:
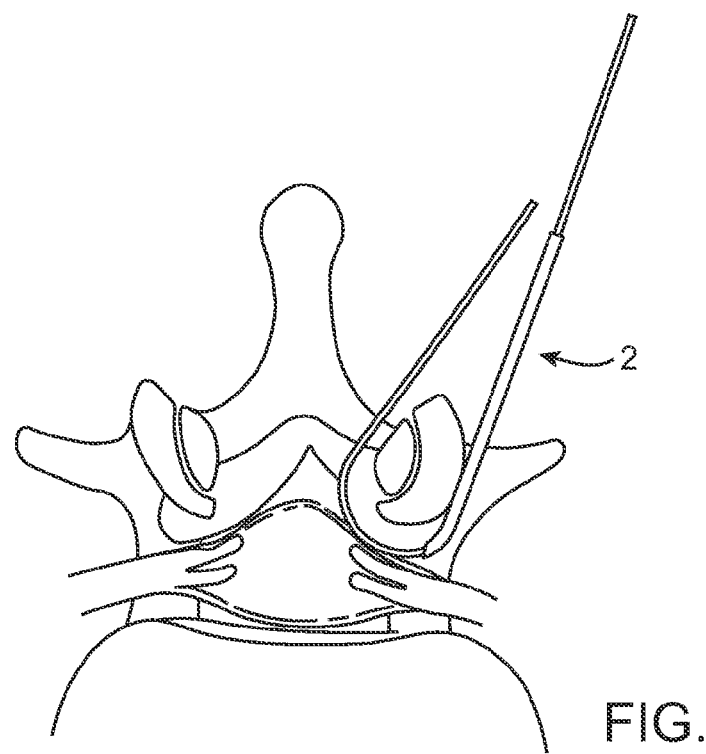

Alternative posterior epidural needle 2 entry approaches into the epidural space are illustrated in FIG. 4, including interlaminar paramedian and midline interspinous techniques, a preferred approach to the medial side of the neural foramen 110. An alternative posterior translaminar approach, where the needle is placed through a hole in the lamina 122 [LA], is not shown. The epidural space may also be entered via a more lateral, neuroforaminal approach to needle placement, as shown in FIG. 71. With any percutaneous epidural approach, after a sterile prep and drape, the epidural needle's 2 sharp tip is inserted through the skin to perform a loss-of-resistance technique.

When a midline approach is used, the epidural needle's 2 sharp tip is inserted through the skin until it begins to engage the interspinous ligaments 78. Subsequently, a fluid or air filled (loss of resistance) syringe 60 is depressed and will meet resistance to injection, until the needle tip is advanced, through the ligamentum flavum 10, entering the epidural space 42, which actually has a slight negative pressure. There is a clear "loss of resistance" to the pressurized contents of the syringe 60, which occurs upon entering the epidural space 42, signifying correct needle tip placement.

When interlaminar access is not possible (e.g. unusual cases when laminae 122 are too tightly approximated, even with flexion of the back), the epidural space may be entered via a translaminar burr hole, using a drill 176 (e.g., an image guided drill) designed for safe epidural entry. Each of these approaches allows placement of the epidural needle 2 tip in the posterior epidural space 42, poised for access to the lateral recess 108 and neural foramen 110.

Figure 9A:
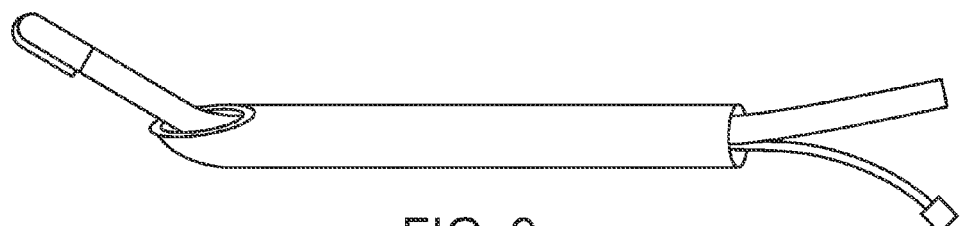
FIG. 9 are also a schematic side view of variations of the apparatus of FIG. 8.
Figure 9B:
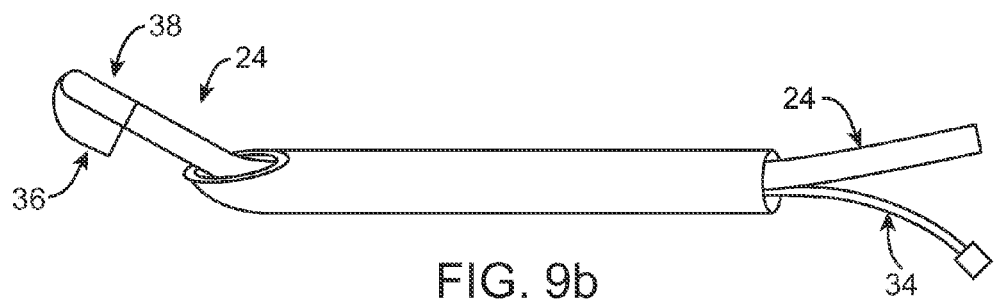
Figure 9C:
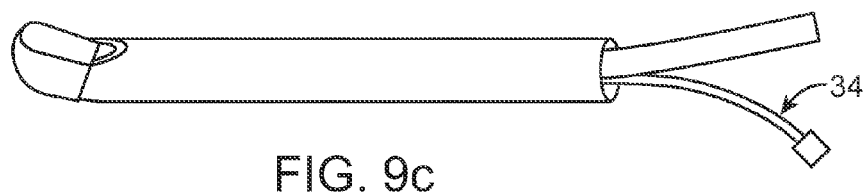
Figure 10A:
FIG. 10 are also a schematic side view of variations of the apparatus of FIG. 6 or 8.
Figure 10B:
Figure 10C:
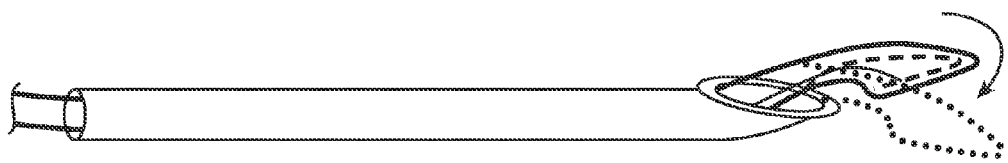
Figure 10D:
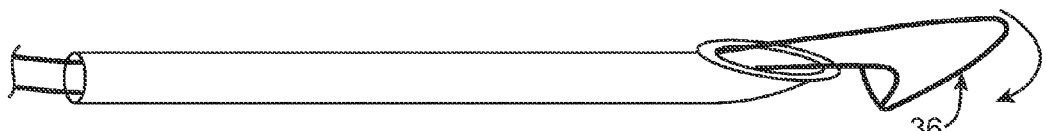
Figure 10E:
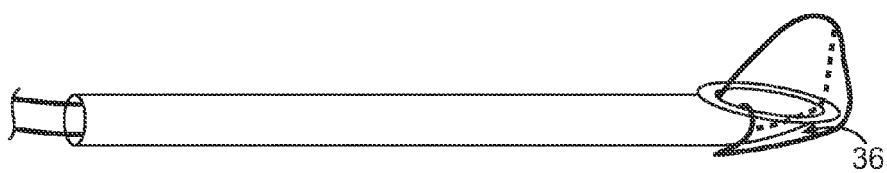
Figure 11A:
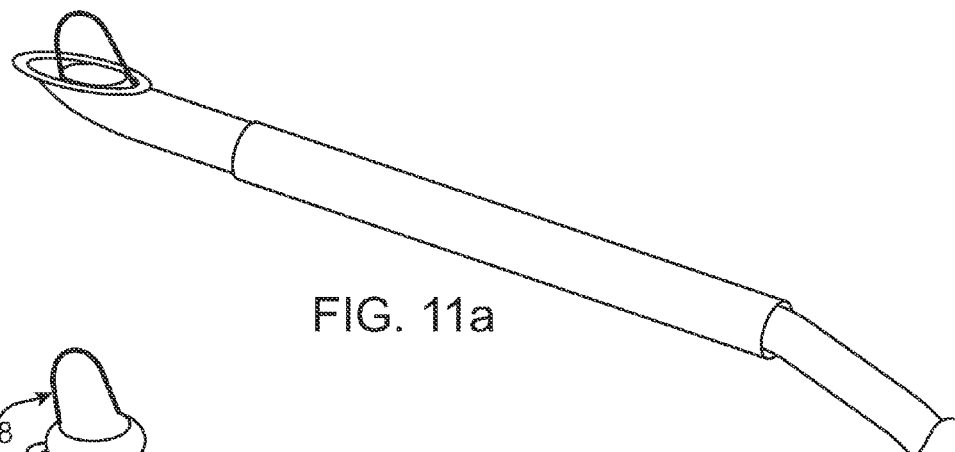
FIG. 11 are also a schematic side view of variations of the apparatus of FIG. 8.
Figure 11B:
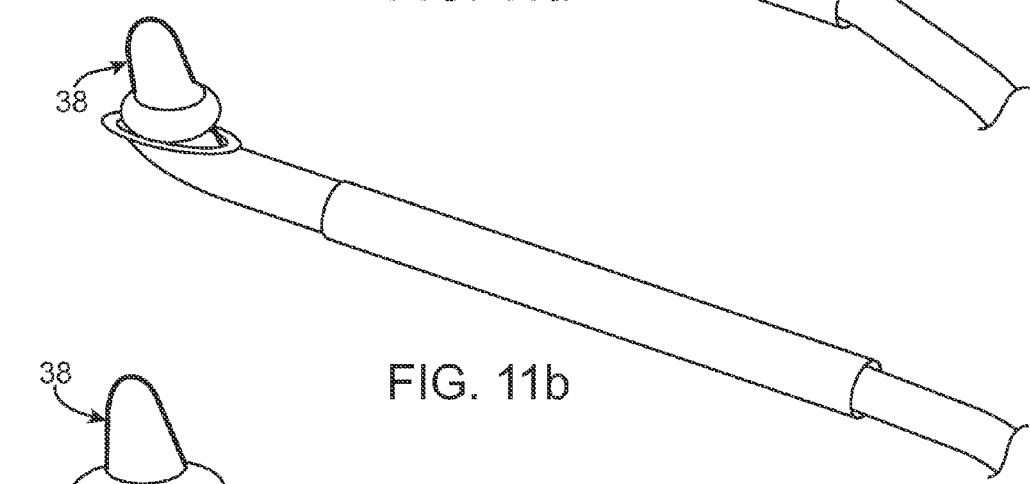
Figure 11C:
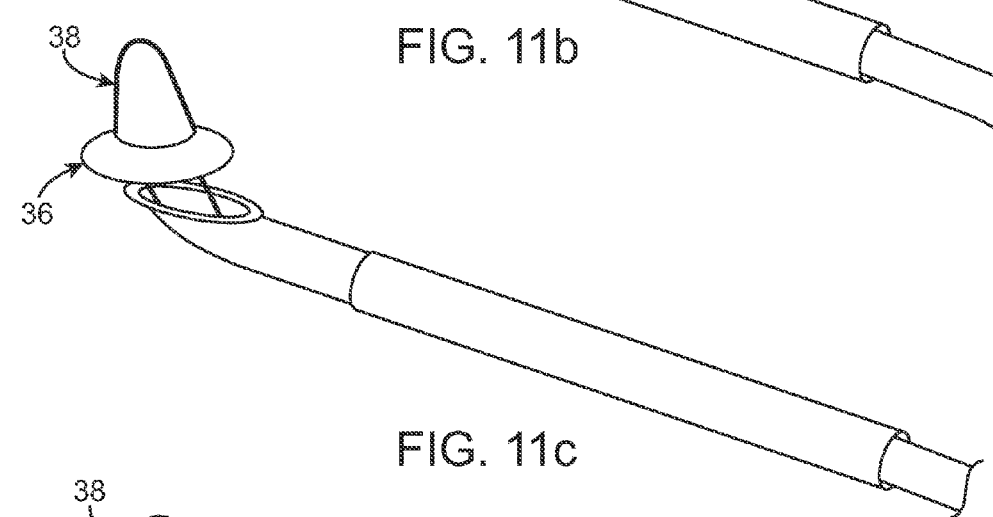
Figure 11D:
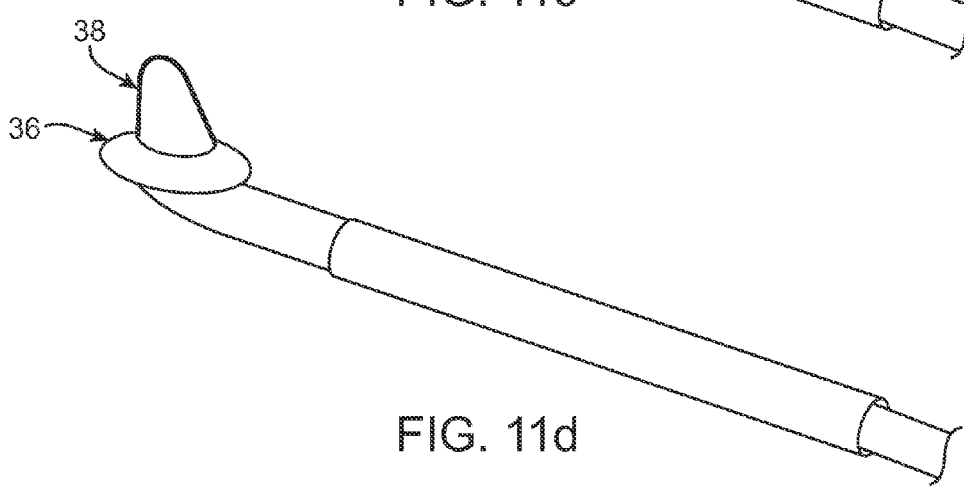
Figure 12A:
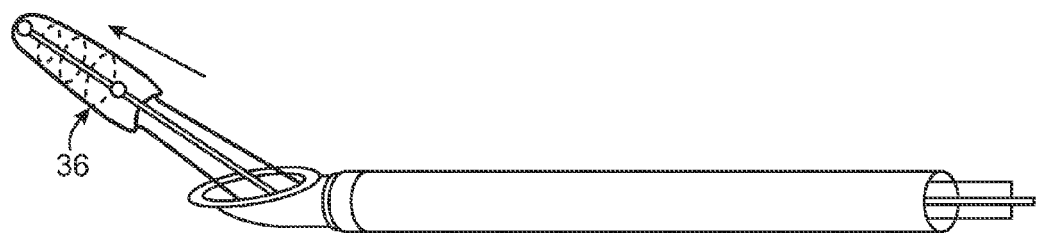
FIGS. 12 a, b, c are schematic side views of variations of the apparatus of FIG. 6 or 8.
Figure 12B:
Figure 12C:
Figure 12D:
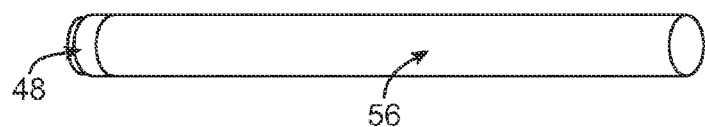
Figure 12E:
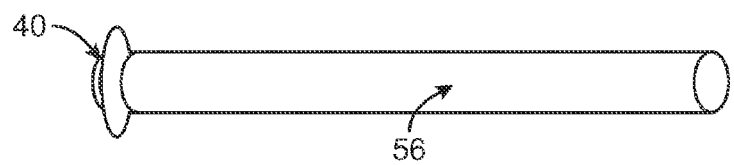
Figure 13A:
FIG. 13 is a schematic side view of variations of the apparatus of FIG. 6 or 8.
Figure 13B:
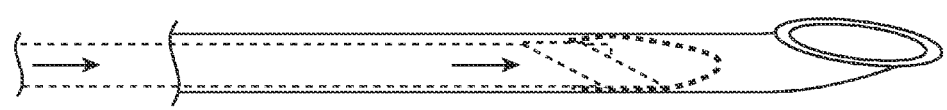
Figure 13C:
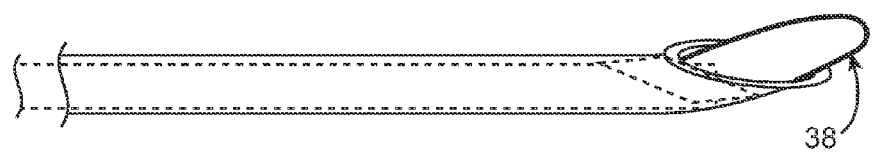
Figure 13D:
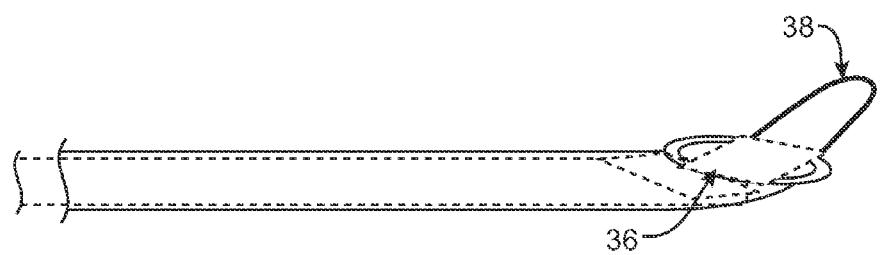
Figure 13E:
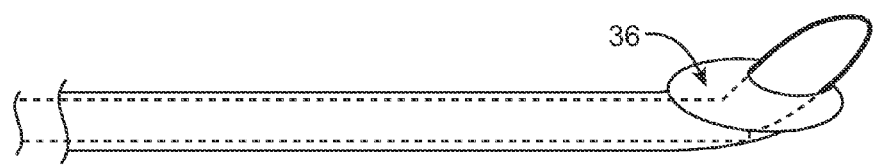

After the epidural needle's distal tip has been placed in the posterior epidural space 42, a specially designed epidural catheter 24 is threaded through the needle 2. Once threaded into the epidural space 42, the epidural catheter's unique epidural needle tip cap or cover 36, located in the distal end of the epidural catheter 24 (with needle tip covering capabilities) is opened and pulled back to cover the sharp epidural needle 2 tip, locked in place, and thereby converts the needle to a non-sharp (e.g., blunt) instrument. The needle, thus converted, may be manipulated and more safely advanced in the epidural space. The blunted needle is subsequently advanced in a direction parallel to the dura 46, in a gentle manner, taking care to avoid inadvertent dural, neural or vascular trauma. With reference to FIGS. 6, 8, 9, 10, 11, 12, and 13, methods and apparatus for protecting, covering and blunting the sharp tip of the epidural needle 2 post-insertion, and optionally converting the epidural needle 2 to an epidural endoscope 132, are described. The catheter apparatus 24 is inserted through the needle, and into the epidural space 42, as in FIGS. 6b, 8b, 9a, 10b, 11b, 12a, and 13c. The catheter tip may be converted to the open position by one of several mechanisms, for example, the catheter illustrated in FIG. 9 has a port 34 for injection of air or liquid to the open the epidural needle tip cover. The injected air or liquid drives (e.g., opens) the actuator for the catheter's tip (needle cover). By forcing air or fluid into port 34 in the epidural catheter 24, a portion of the catheter's tip 36 may be expanded, as in FIGS. 6b, 8c, 9b, 11c, 12b, or 13e, to inflate or otherwise open the needle's protective cover or cap 36. In another variation, an alternative means of actuation of the cap system on the epidural catheter 24 may be a wire or string that pulls the cap into a new shape. For example, FIG. 12 demonstrate a sliding umbrella-like mechanism for actuation of the distal epidural catheter 24 based needle tip cover 36. FIG. 9B shows the epidural "needle cap" or "fiber cap" 36 in the opened position. In certain embodiments, the catheter may next need to be pulled back proximally through the needle 2 until, as in FIG. 9C, until the epidural needle cover 36 is engaged over the distal needle tip, protecting the dura 46, neural and vascular structures from the sharp point of the needle 2, which is no longer exposed. Markings on the catheter may be used to demonstrate to the surgeon that the catheter is in the correct position, allowing the blunted epidural instrument to be safely advanced.

Once the tip of the epidural needle 2 has been blunted or capped, and no longer has a sharp exposed portion, the needle may be safely advanced within the epidural space, preferably in a direction parallel to the dura 46 (FIG. 13). In one variation, the epidural needle 2 tip is covered by the catheter based device, then is advanced through the epidural space under image guidance (e.g. fluoroscopy, CT, x-ray, MRI, Ultrasound, etc.), towards the area where tissue resection, ablation or remodeling is to be performed.

In an alternative variation of the method and device, as in FIGS. 8, 9, 11, and 13, the epidural catheter 24, in addition to a needle tip cover, also contains a fiberoptic cable 38 (or clear cover over the distal end of the fiberoptic cable within the epidural catheter), which enables conversion of the epidural needle 2 into an epidural endoscope 132. The fiberoptic component 38 of the catheter provides the surgeon with an ability to directly visualize the epidural space 42. In a further variation of the method, both fiberoptic visualization and image guidance may be used concurrently.

Figure 6A:
FIG. 6 are schematic side views illustrating a method and apparatus, in accordance with the present invention, for covering with a cap and blunting the sharp tip of an epidural needle post-insertion.
Figure 6B:
Figure 6C:
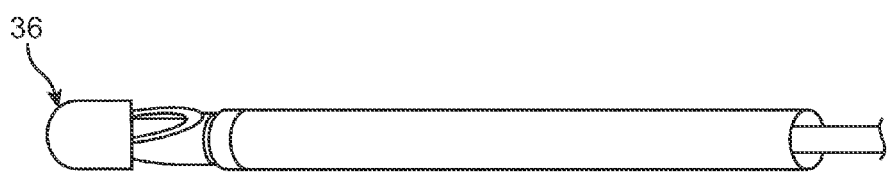

In this apparatus and method for enabling safe manipulation of the apparatus in the epidural space, an epidural needle 2 is first placed in the posterior epidural space 42 in a similar manner to what was described above. With the needle tip in the epidural space 42, an epidural catheter 24 apparatus is used to deliver a cover to the sharp epidural needle 2 tip, converting the needle to a blunt instrument for further atraumatic advancement of the apparatus into the epidural space, as shown in FIGS. 6, 9, 11, and 12. After the catheter 24 is advanced through the epidural needle 2 into the epidural space 42, as in FIGS. 6a and 9a, a distal portion of the catheter is converted to a shape that will be used to cover the sharp epidural needle 2 tip, as illustrated in FIG. 6b.

Once the cover 36 in the distal catheter 24 is opened, the catheter 24 is gently pulled back until the needle tip is covered and thereby blunted. The capped needle is next carefully advanced within the epidural space 42, between the ligamentum flavum 10 and the dura 46, somewhat parallel to both, towards one of the neural foramen 110, with much less risk of inadvertent dural puncture. In order to further facilitate safe advancement of the capped needle in the epidural space, image guidance may be used. Additionally or alternatively, the epidural needle 2 may be converted to an epidural endoscope. Conversion to an endoscope may be performed by either converting the epidural needle 2 to an endoscope directly ("needlescope"), or by utilizing the epidural needle 2 to enable placement of an endoscope cannula or portal 56, which will replace the needle 2. The needle 2 may be converted to an endoscope directly through use of the catheter 24 that is used to cover, blunt, or "safe" the epidural needle 2 tip. The epidural catheter 24 optionally may contain a rigid or flexible fiberoptic element 38, through which the surgeon may view the epidural space 42, thereby converting the epidural needle 2 into an epidural endoscope. The tip of the fiberoptic catheter would, in such a case, be clear 38.

Figure 7A:
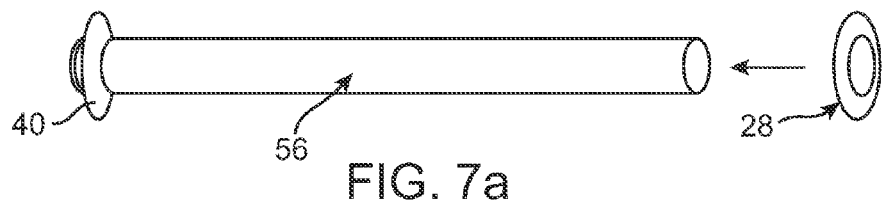
FIG. 7 are also a schematic side view of variations of the apparatus of FIG. 6 with a method for also limiting the depth of insertion of cannula, access portal, or needle.
Figure 7B:
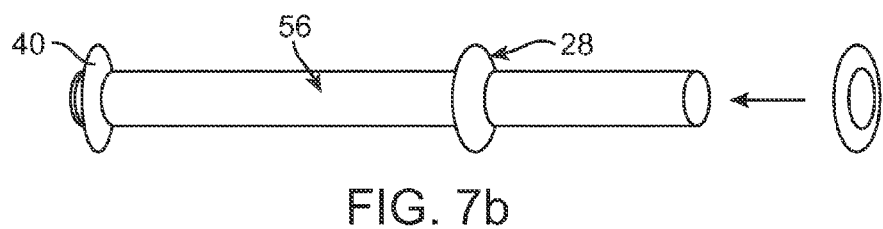
Figure 8A:
FIG. 8 are schematic side views illustrating a method and apparatus in accordance with the present invention for covering with a cap and blunting the tip of the epidural needle post-insertion, and optionally converting the epidural needle to an epidural endoscope, for safe further advancement of the needle into the epidural space.
Figure 8B:
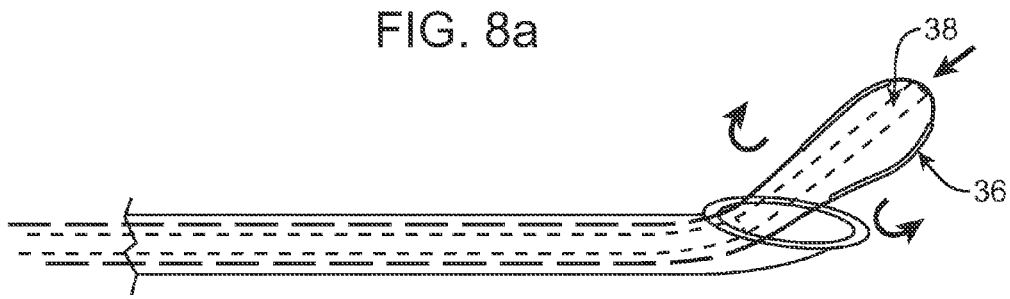
Figure 8C:
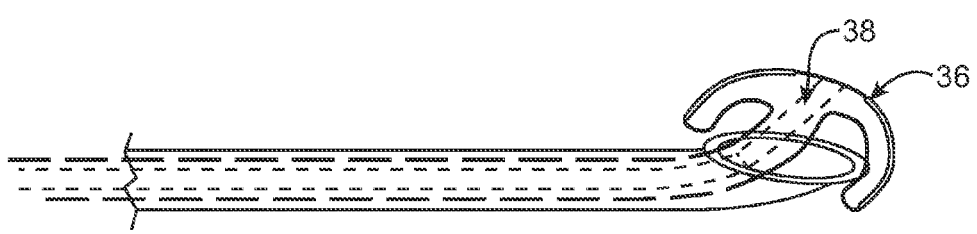

FIG. 7 illustrates a distal epidural anchor 40. The distal epidural portal anchor 40 can, in its engaged position, hold the distal portion of the epidural apparatus in the epidural space, anterior to the ligamentum flavum. FIG. 7 also illustrates that the portal, needle, or endoscope may include a proximal epidural anchor, stopper or lock 28 (e.g., to anchor on the skin) that may be advanced from the proximal end of the device (skin side), in order to help to prevent the percutaneous device from advancing further into the epidural space than is desired (as in FIG. 7b). The lock 28 can be inserted over the portal and against the skin when the portal is at a desired depth.

Figure 82A:
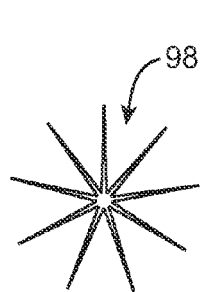
FIG. 82a-c are cross-sectional views through a protective sleeve or sheath, compact (a), during insertion (b), and expanded (c) by passing the apparatus through its lumen.
Figure 82B:
Figure 82C:
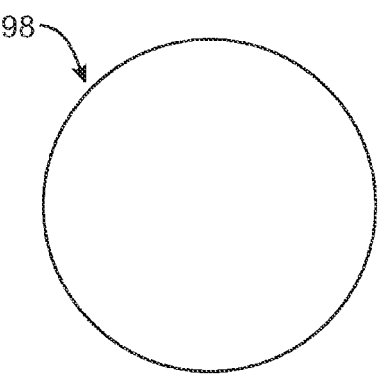

In a further variation of the apparatus and method, an epidural portal 56 would allow interchangeable epidural endoscopes to be used to view or work within the epidural space. An epidural needle 2 may be used to place an endoscope portal 56, using one of the three following general approaches: (a) In one variation, a portal is an expandable catheter (e.g. FIG. 82) that is delivered as a catheter through the epidural needle 2; (b) In another preferred embodiment, an epidural needle 2 may be inserted into the epidural space, with a thin walled epidural cannula or portal 56 already in place over it, similar to the method and apparatus of standard intravenous cannulation with IV catheters used today. This technique would ideally be used in conjunction with the epidural needle 2 method and apparatus, so that the needle may be advanced far enough to safely also place the neck of the cannula or portal 56, which is a short distance proximal to the distal tip of the epidural needle 2, into the epidural space. In order be able to safely advance the portal 56 into the epidural space, the needle may be covered or blunted, as described above, using a catheter that does not contain a fiberoptic element, as in FIG. 6. With the sharp tip covered, the needle may be subsequently advanced a few millimeters, until the distal tip of the portal has also been advanced into the epidural space 42; (c) In a third embodiment of the method and apparatus, the portal 56 may be inserted over a soft tipped flexible guidewire that has been placed through the epidural needle 2, analogous to the popular "Seldinger Technique" (a standard cannula over needle insertion approach to vascular access).

Figure 14A:
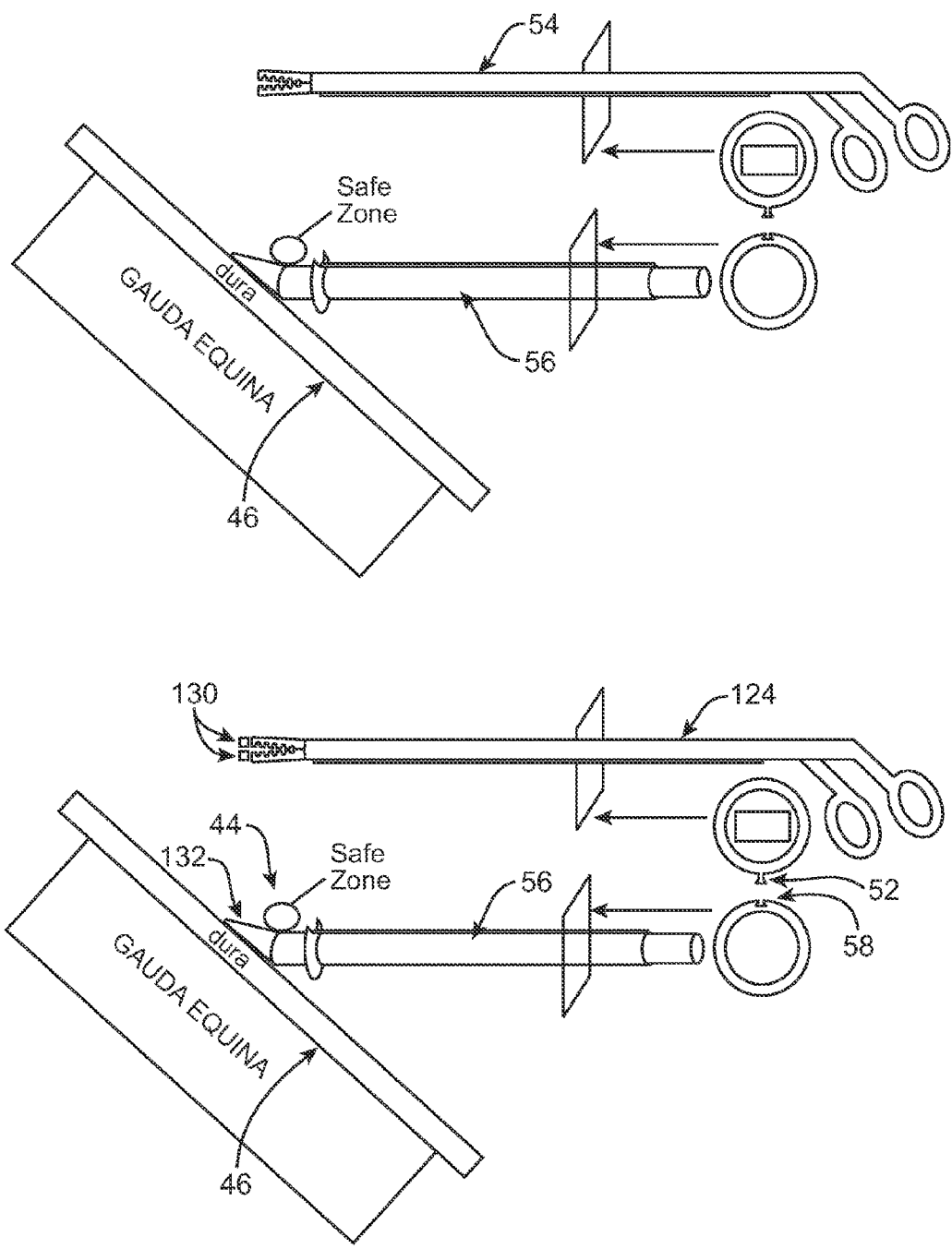
FIG. 14a is a schematic side view, partially in section, of variations of the apparatus, illustrating methods of safely utilizing the apparatus (e.g., safe tool access) for safe placement and use of surgical tools in or around the epidural space.

With reference to FIG. 14, additional variations of the apparatus of FIG. 9 are described, illustrating methods of safely utilizing the apparatus, in combination with additional surgical tools. Safe tool access, for example, may be facilitated by the inclusion of either a working channel 50 on an epidural endoscope, or by sliding the tool along a rail 52 and slot 58 interface on the epidural cannula or "needlescope" 56. FIG. 14A shows tool 54 (illustratively a grasper) fitted with rail 52 that mates with a slot 58 of epidural endoscope, so that it may be inserted directly into the epidural space 42 and placed in the "safe zone", without the need for a working channel along endoscope/needle.

Figure 14B:
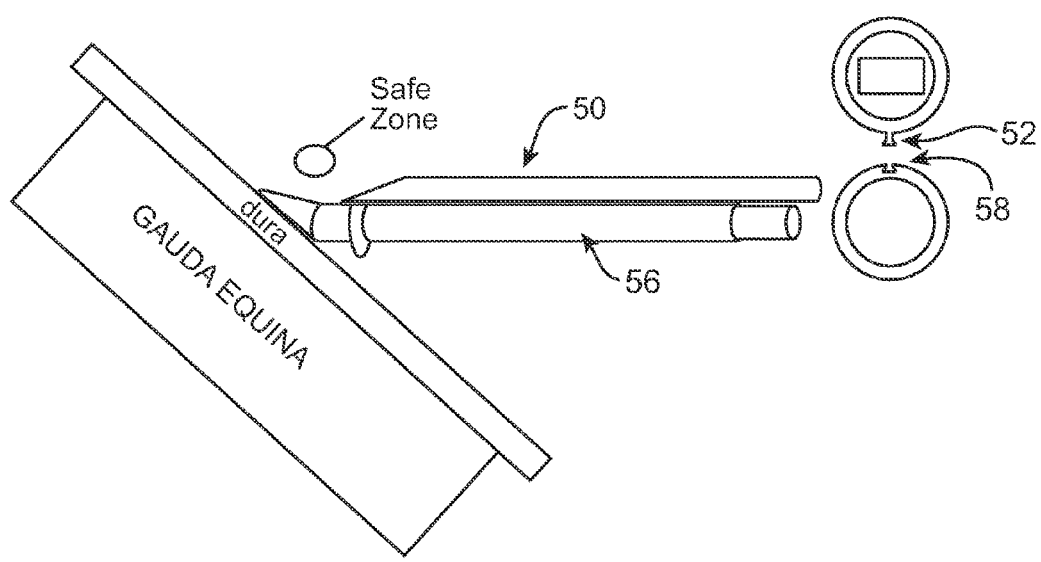
FIG. 14b are side views, partially in section, illustrating a method and apparatuses for safe placement of a tool or working channel into the epidural space.

In FIG. 14B, working channel 50 is disposed along epidural needle 2, "needlescope", or endoscope, e.g., is integrally formed with the endoscope or is positioned via a rail and slot mating, or a similar removable fastening mechanism, with the endoscope. FIG. 14B illustrates an epidural working channel 50 in place, connected to the cannula, needle, or endoscope, with its tool-presenting end adjacent to the "safe zone".

In order to further facilitate working in the epidural space 42, the epidural portal or cannula 56 may have, preferably close to its distal tip, an anchor system 40 to prevent said apparatus from inadvertently slipping out of the epidural space 42, as illustrated in FIG. 7. The anchor 40 may be engaged towards the distal tip of the cannula or portal 56, anterior to the ligamentum flavum 10. The portal 56 may also be anchored external to the epidural space 42, e.g., to the patient's skin 70 (e.g., of the patient's back), or within interspinous 78 or supraspinous ligaments.

Figure 15:
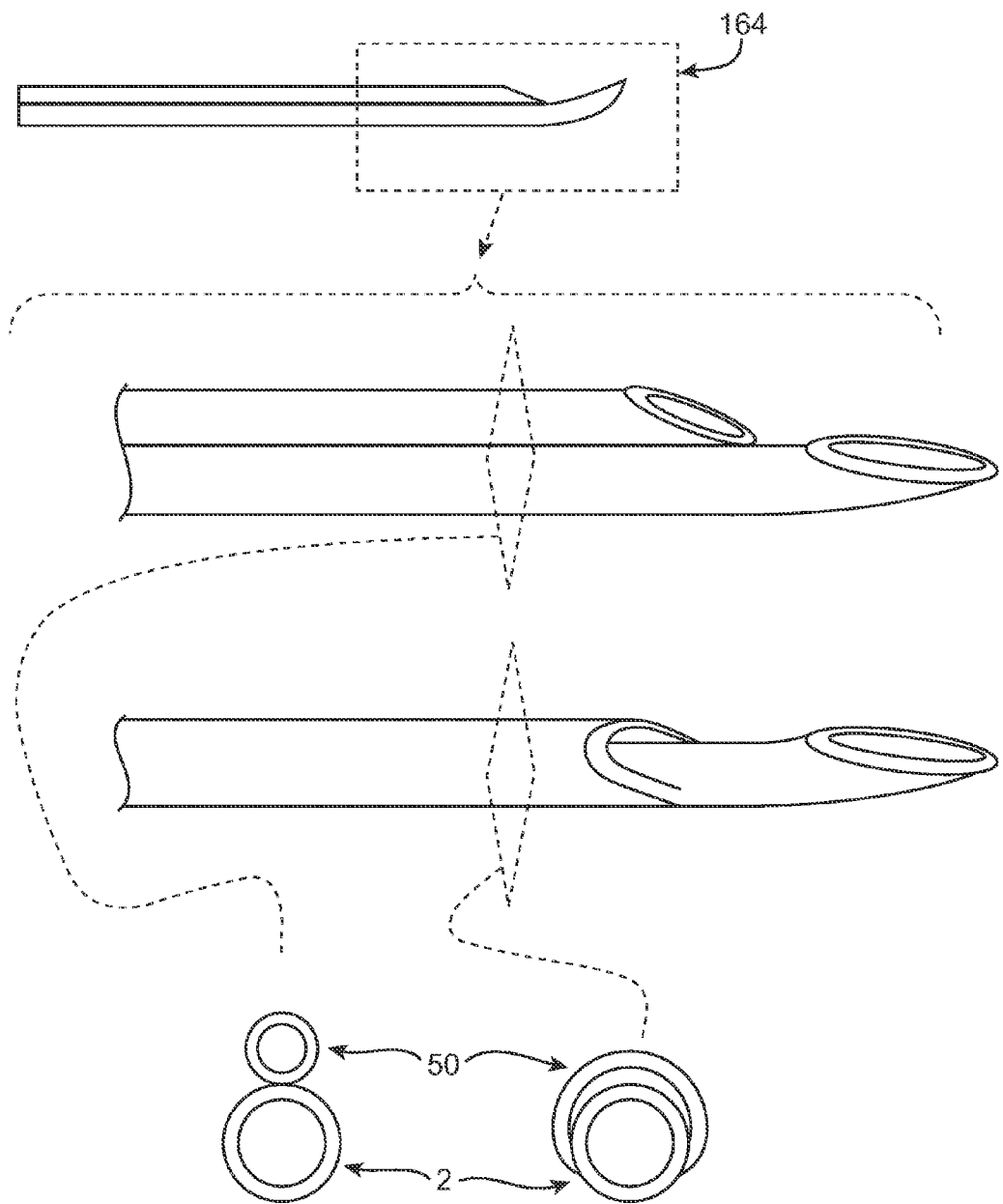
FIG. 15 are side views illustrating apparatuses that include a double barreled epidural needle, with the epidural needle as the most distal point, and with the working channel the more proximal tip. This system may also be converted to an endoscope and may be used for safe placement of instruments into the epidural space.

Referring now to FIG. 15, an additional method and apparatus for placement of the tissue modification elements is illustrated. A twin (i.e., double) lumen epidural needle 84 is illustrated, comprising a working channel 50 adjacent to the epidural needle 2. The second lumen serves as a working channel 50, or for the delivery of tools into or adjacent to the epidural space 42. Note that the distal beveled aperture of the working channel is proximal to the epidural needle 2 tip, and opens onto the side of the epidural needle 2 that the epidural bevel faces. The double lumen epidural needle 84 can have a proximal bevel representing a working channel and a distal bevel representing an epidural access needle and, potentially, an endoscopy port or an additional working channel.

Figure 16:
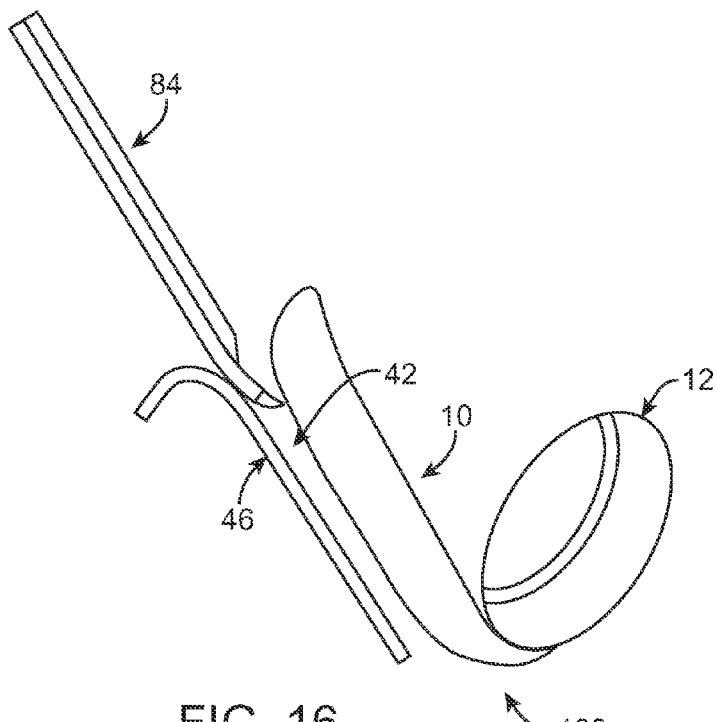
FIGS. 16-18 are cross-sectional views through a patient's spine, illustrating a method and apparatus for placement of a double barreled epidural needle or endoscope, the sharp tip of which has been covered in FIG. 17, and thereby blunted, for safe advancement towards the lateral recess and neural foramina. The blunted epidural needle apparatus may contain a fiberoptic cable for direct visualization, in a preferred embodiment.
Figure 17:
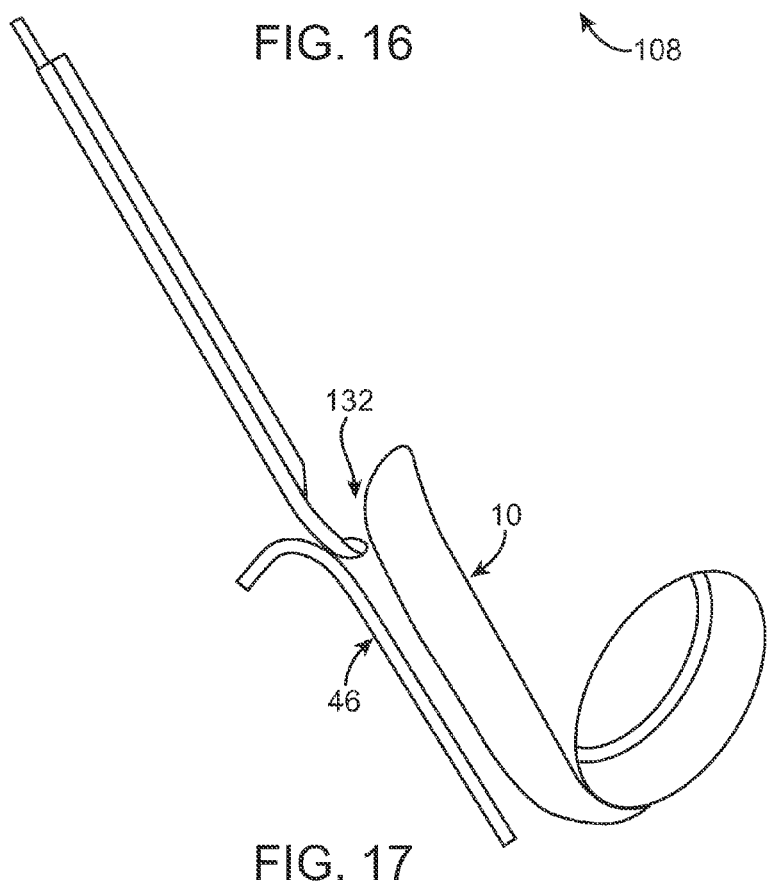
Figure 18:
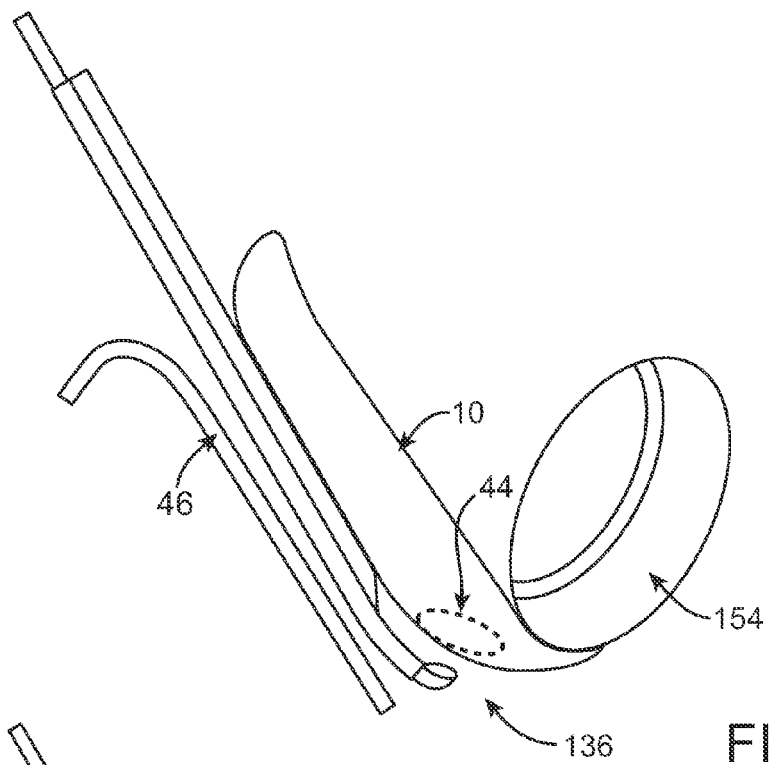
Figure 19:
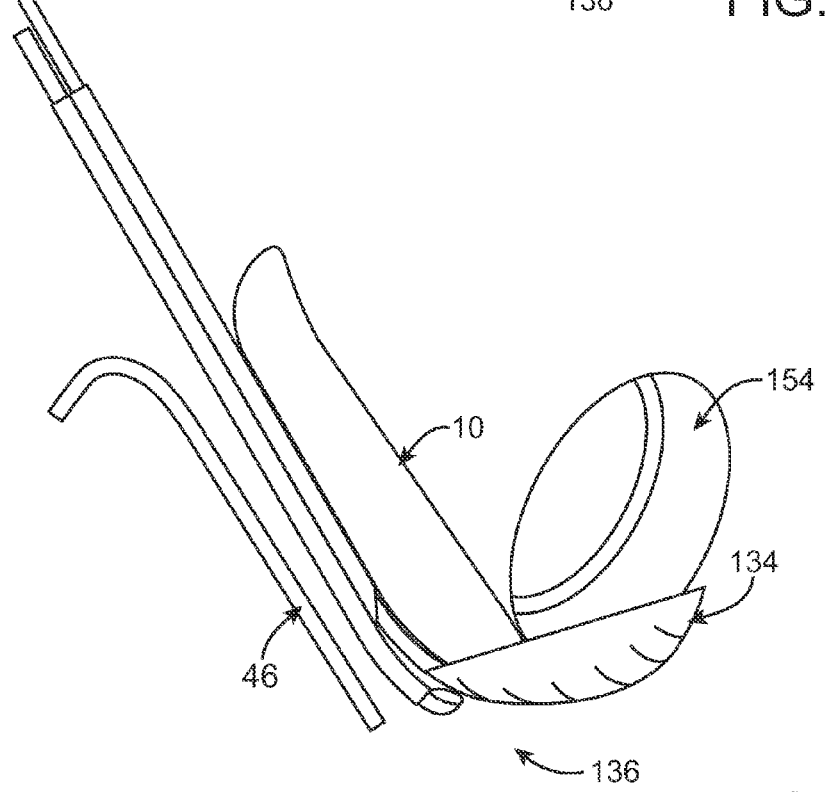
FIG. 19 is a cross-sectional view through a patient's spine that illustrates a method, following FIGS. 16-18, for placement of a working backstop or barrier into the lateral recess and/or neural foramina. The barrier or backstop may contain elements for neural localization.
Figure 20A:
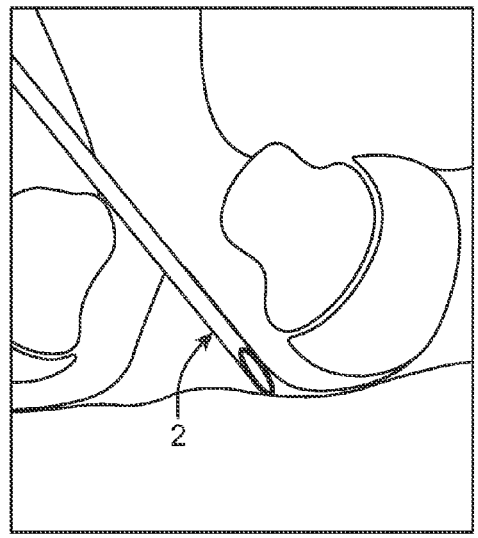
FIGS. 20-21 are cross-sectional views through a patient's spine that illustrate alternative methods and apparatuses for placement of a working backstop or barrier to enable safe tissue resection, ablation, abrasion or remodeling.
Figure 21A:
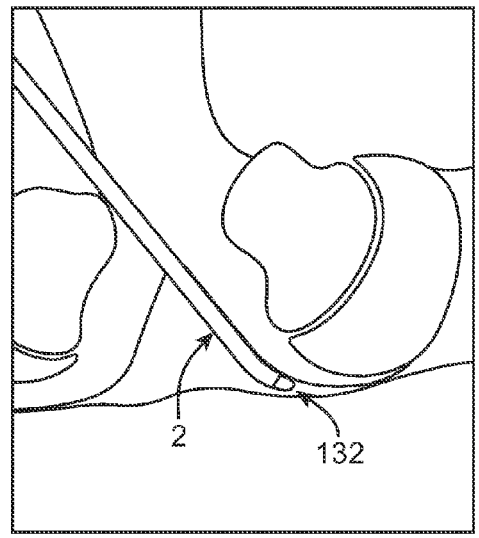
Figure 20B:
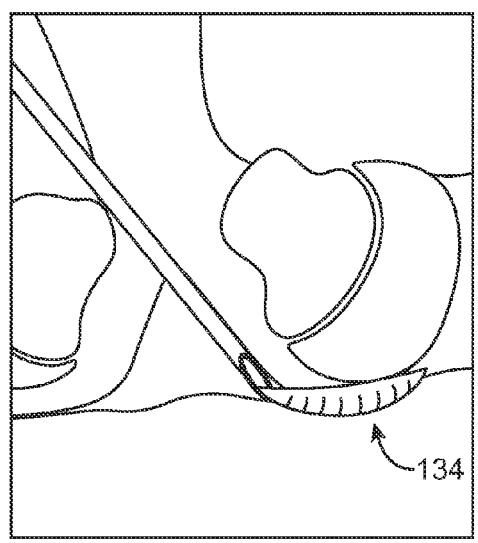
Figure 21B:
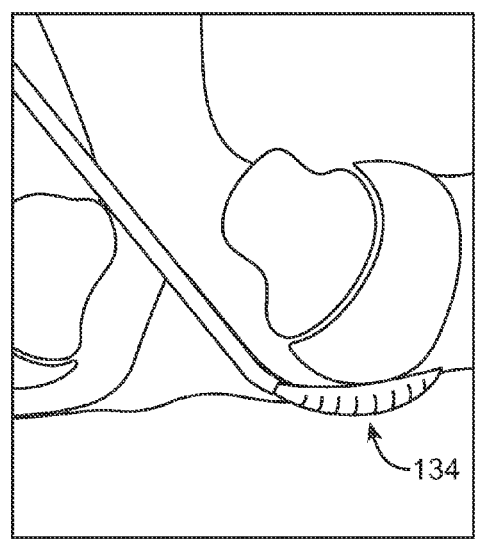
Figure 22:
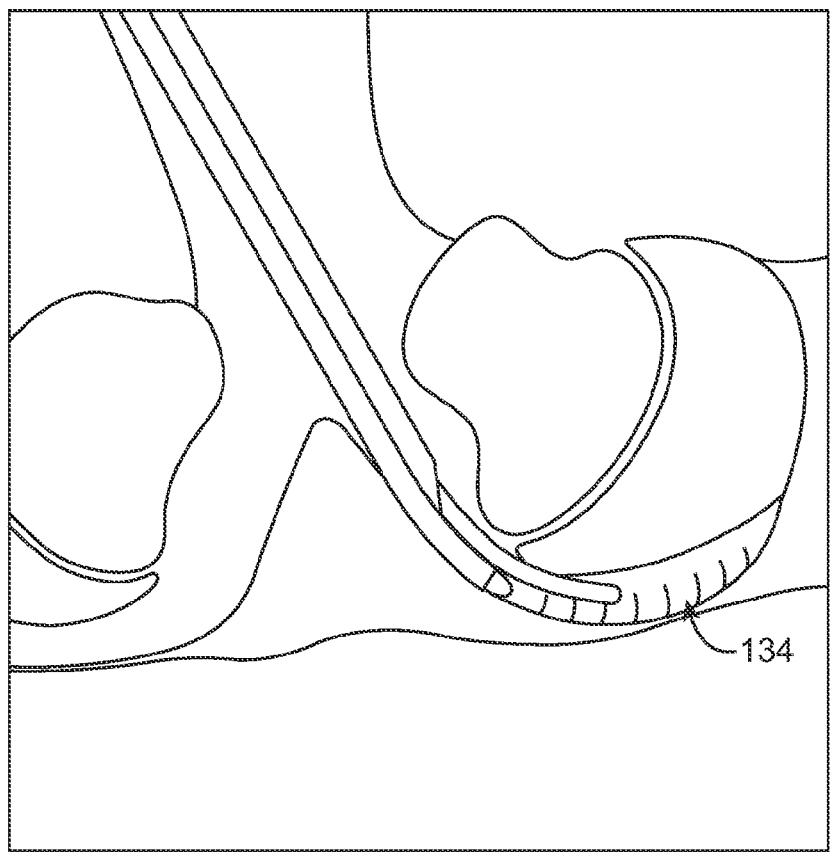
FIG. 22 is a cross-sectional view through a patient's spine that illustrates a tool inserted through the working channel (example shows a shaver or burr), with its tip in position for tissue removal or debridement, adjacent to a protective working backstop or barrier.
Figure 23A:
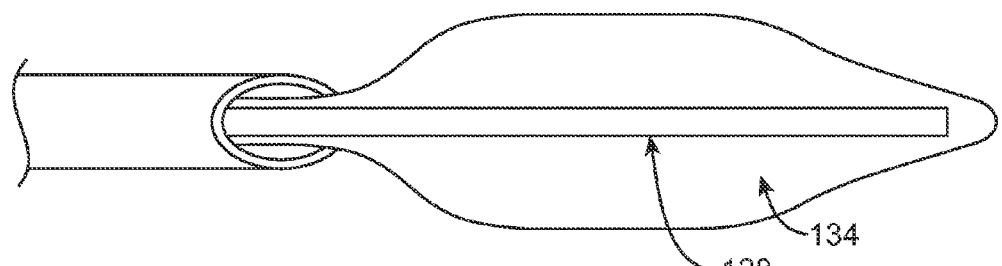
FIGS. 23a-23d are schematic views of a working backstop or barrier apparatus, including an optional rail for controlled tool placement in relation to the barrier, and an optional conductive element for neural localization.
Figure 23B:
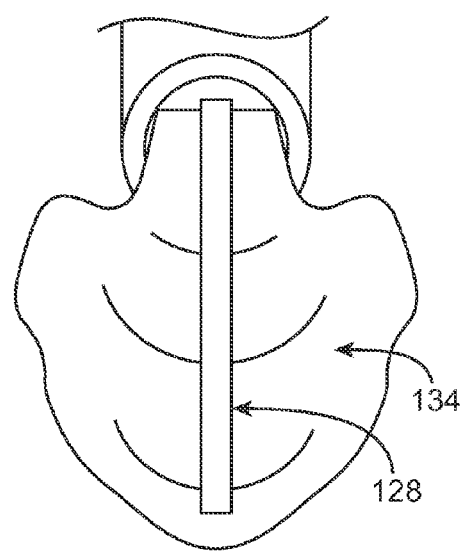
Figure 23C:
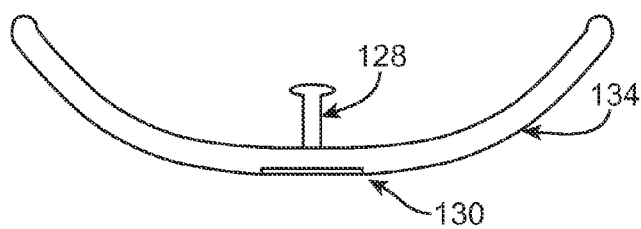
Figure 23D:
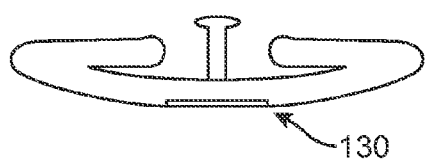
Figure 42:
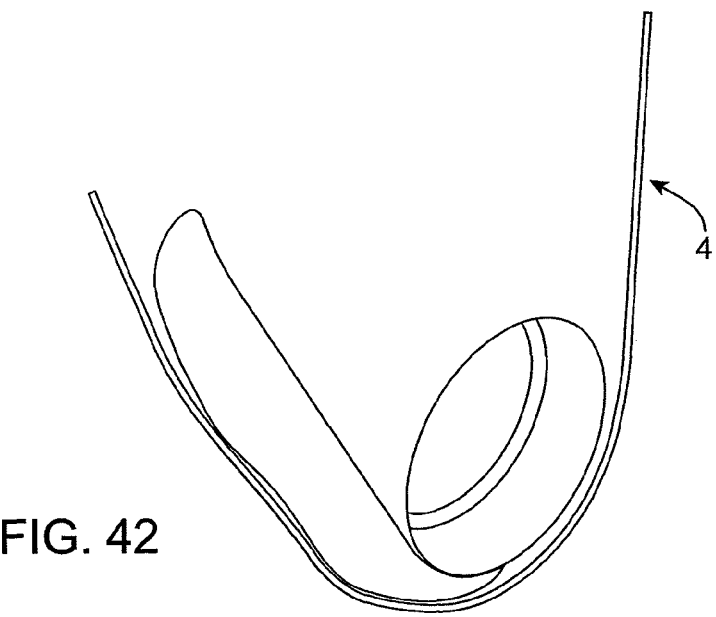
Figure 43:
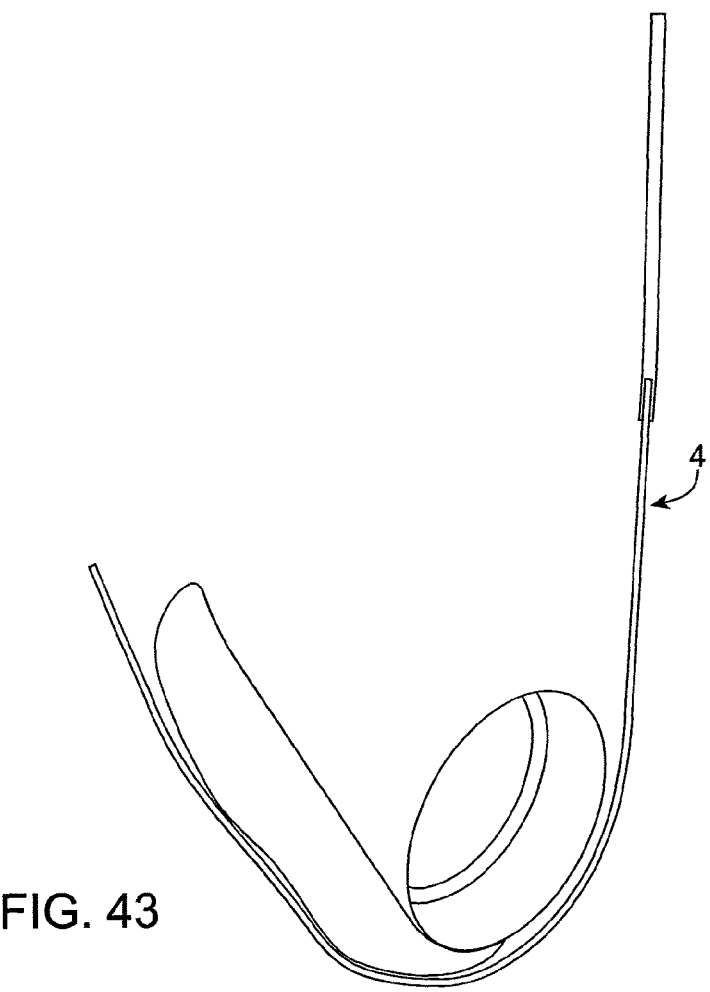
Figure 44:
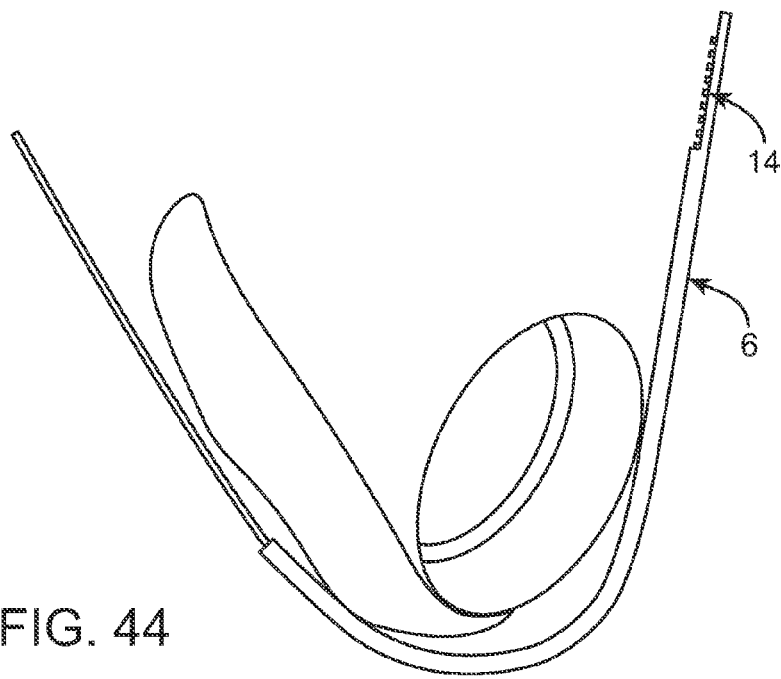
Figure 45:
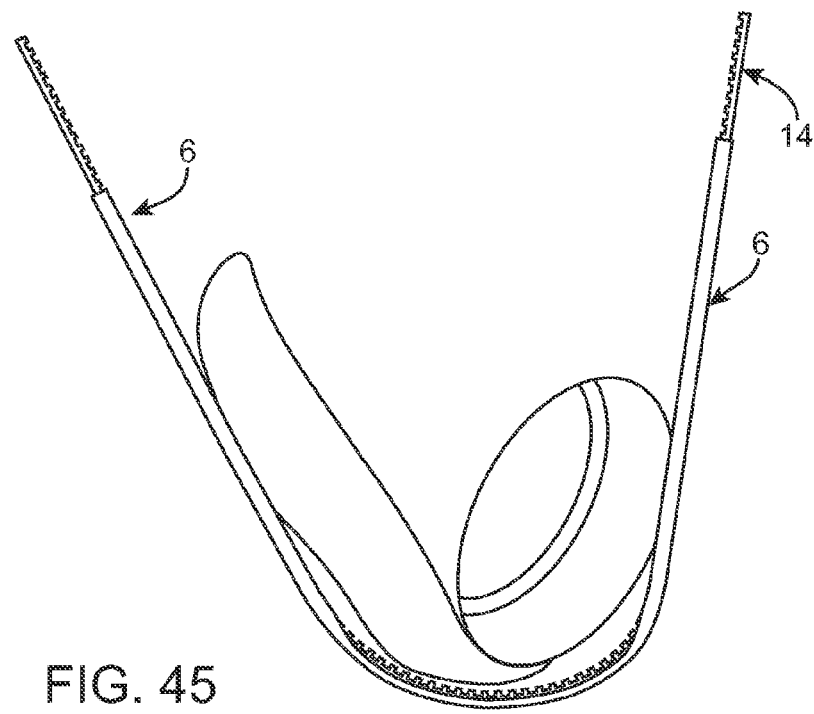

Referring now to FIGS. 16-19 and 42-45, an additional method and apparatus for placement of a tissue abrasion apparatus for selective surgical removal or remodeling of tissue is described. In FIG. 16, the double lumen epidural needle apparatus is positioned for advancement into the epidural space 42. FIGS. 17 and 18 show how the covered and blunt tip of the epidural needle 2, double lumen epidural needle 84, or the blunt end of the epidural endoscope, may be advanced into the ipsilateral or contralateral lateral recess 108, towards the neural foramen 110, in a direction parallel to both the adjacent ligamentum flavum 10 and the dura 46. In the illustrated example of the apparatus and method labeled FIG. 17, a fiberoptic element 38 has been placed within epidural needle 2, providing both a means for fiberoptic visualization of the epidural space 42 and a means to blunt the needle and thereby protect the tip of the needle from damaging the dura 46 or neural or vascular structures. In FIG. 18, the endoscope has been advanced along ligamentum flavum 10 (visually yellow, otherwise known as "the yellow ligament") to the lateral recess 108. "Safe zone" 44 designates the area in which a medical practitioner may resect, ablate, or otherwise modify tissue safely, directly visualizing the are of tissue modification through the fiberoptic element. The safe zone 44 is the area posterior to the apparatus in the epidural space, where dura is known to be on the other side of the apparatus, and is therefore a safe zone for tissue alteration without damaging dura or central nervous system structures, particularly when using fiberoptic visualization through the distal lumen. The second lumen of the two lumened needle 84 or endoscope may be used as a working channel 50, or to dispense the abrasive element 14 and/or its protective sleeve 6, or the working barrier described in the primary patent referenced herein. After the neural foramen 110 has been cannulated with a non-sharp curved needle 16 or catheter, and after the flexible, sharp, straight needle or wire 4 (e.g., a guidewire) has been passed through the curved needle 16 until its tip is advanced through the skin in the patient's back 70, the abrasion apparatus 14 and/or its sleeve or cover 6 are pulled through the neural foramen 110, as illustrated in FIGS. 43-45. The curved needle 16 or tube may, for example, be fabricated from a spring steel, Nitinol, or other memory material that will allow it to be inserted through a straight needle, but to return to a fixed curve upon exiting the straight epidural needle 2 or working channel 50. The curved needle 16 optionally may be steerable. Preferably, the curved needle tip is not sharp, but is rounded or designed in other fashions less likely to cut tissue, in order to reduce a risk of neural or vascular damage.

In yet an additional embodiment of the invention ("portal over epidural needle" variation), an epidural portal 56 may be inserted into the epidural space 42 as a catheter over the epidural needle 2 (as in FIG. 12), similar to the design for placement of standard intravenous catheters used today. With such an approach, advancing the blunted needle (sharp tip covered) by several millimeters will also bring the distal tip of the portal into the epidural space 42. Subsequently, the needle may be withdrawn from the portal, which is held in place by the surgeons other hand, leaving the epidural portal in the epidural space 42 as a working channel or endoscope guide.

In one variation, the epidural needle 2, needle based endoscope, flexible or rigid endoscope, or portal 56 (for placement over an epidural needle 2) may have, preferably close to its distal tip, an (e.g., distal) anchor mechanism 40 and 48 (in its un-engaged position) that may be inflated or otherwise opened (e.g., in the epidural space 42), to help prevent inadvertent removal of the device from the epidural space 42. It is expected that utilization of an anchor to, or within, the ligamentum flavum 10, will prevent the portal from being pulled inadvertently through the ligamentum flavum, and will enhance the reliability and safety of epidural access for minimally invasive endoscopic surgery.

FIG. 14 illustrates additional methods of safely utilizing a blunted epidural apparatus in conjunction with additional surgical tools. Safe tool access may, for example, be facilitated with either a fixed working channel 50, as shown in FIG. 15, or by the creation of a rail 52 and slot 58 interface on the tool or epidural endoscope, cannula or "needlescope" 132, as shown in FIG. 14b. The working channel 50 can be insertable and removable and can be for attachment to the epidural apparatus. The rail portion 52 of the epidural instrument can be for guiding the epidural tools along the blunted epidural apparatus into the epidural space. The slot portion 58 of the epidural instrument or portal can be for guiding the epidural tool or working channel into the epidural space. Note the rail 52 and slot 58 may be reversed, with the rail 52 on the sleeve or scope and the slot 58 on the tool or working channel.

FIG. 14a shows a tool 54 (illustratively a grasper) fitted with a rail 52 that mates with a slot 58 of epidural endoscope 132, so that it may be inserted directly into the epidural space 42 and then advanced until it is placed in the "safe zone" 44 (e.g., for tissue resection or modification, on an opposite side of the epidural tissue), without the need for a working channel along endoscope/needle 132. The part of the epidural tool that is expected to be in direct contact with the impinging spinal tissues 124 that the surgeon intends to modify provides an ideal location for neural stimulator lead placement 130. In the example illustrated in FIG. 14a, an insulated tool shaft is combined with a conductive surface 130 on the tip of the grasping tool 54, to be used for neural stimulation. (note: the use of neural stimulation with sensorimotor monitoring, for neural localization, in conjunction with the current invention, will be discussed later in this document)

In one variation, the epidural needle 2 is curved towards its distal end, e.g into a hockey stick shape. In a curved configuration, the lumen exits the bevel, distal to, and on the concave side of the bend in the needle's distal shaft. With such a configuration, a "safe zone" 44 is created by inserting the needle so that the side opposite the bevel (convex side of the bend) is in direct contact with the dura, and the lumen, on the concave side of the bend, faces the ligamentum flavum. This configuration provides a "safe zone" 44, where tools, or a working channel 50, may be reliably placed on the needle side opposite the dura 46.

In FIG. 14*b*, a removable working channel 50 is disposed along epidural needle/endoscope 132, e.g., is integrally formed with the endoscope or is positioned via a rail 52 and slot 58 mating with the endoscope 132. FIG. 14*b* illustrates an epidural "needlescope" 132 or endoscope cannula with the working channel 50 in place, with its tool-presenting end adjacent to the "safe zone".

Referring now to FIGS. 16-19, an additional method and apparatus for selective surgical removal of tissue is described. In FIG. 15, a double barrel epidural needle 164 is illustrated, comprising a working channel 50 adjacent to the epidural needle 2. In FIG. 16, the double lumen epidural needle apparatus is positioned for advancement into the epidural space 42 (e.g., a safe triangle, an area at the most posterior aspect of the epidural space 42, where epidural needle 2 tip insertion is most consistently safely performed). In FIG. 17, a catheter based fiberoptic element 38 has been placed within epidural needle 2, providing both a means for fiberoptic visualization of the epidural space 42 and a means to blunt the needle and thereby protect the tip of the needle from damaging the dura 46 or neural or vascular structures. In FIG. 18, the endoscope has been advanced along the ligamentum flavum 10 to the lateral recess 136. "Safe zone" 44 designates the area in which a medical practitioner may resect, ablate, or otherwise modify tissue safely, under direct visualization. The second barrel or lumen of the double barreled needle 164 or endoscope may be used as a working channel 50, or to dispense a tissue modification barrier or working barrier or backstop 134.

In addition to the insertion of tools through the epidural needle 2, or through an adjacent working channel 50, the same channels may be utilized to insert a barrier 134, or "working backstop" 134 (FIGS. 19, 20*b*, 21*b*, 22, 23, 24), into the spine. In a further variation of the present invention, a flexible, flat, thin mechanical barrier ("working backstop") 134 is placed between the tissue to be resected and adjacent vulnerable neural or vascular structures that are desired to be left intact and uninjured. The barrier provides protection for the dura 46, nerve root 62, dorsal root ganglia, and/or vasculature, by providing insulation and/or preventing direct contact between the tools and these vulnerable structures during tissue manipulation, resection, abrasion, or remodeling. The protective barrier may be placed between the needle based or endoscopically delivered tools and the dura 46 in the central spinal canal; in the lateral recess 136; or between the tools and the neural and neurovascular structures within the neural foramen 110. The barrier 134 may be placed through the neural foramen 110 anterior to the facet joint 77, either anterior to the ligamentum flavum 10 (epidural space 42) or within or posterior to the ligamentum flavum 10 (posterior to the epidural space 42). Tools that may be used in conjunction with this barrier include, but are not limited to, cautery devices (monopolar or bipolar), lasers (erbium, etc.), rasps, ronguers, graspers, burrs, sanders, drills, shavers, or probes.

The barrier or backstop 134 may be placed percutaneously via a needle 2, endoscope 132, or double barreled needle 164. In addition to epidural endoscopy, image guidance may be combined with the use of straight, curved, or steerable guidewires for the proper placement of the barrier or backstop 134. In an open surgical variation, the barrier or backstop device 134 may be placed through the surgical incision.

The barrier 134 may be synthesized from one of several possible materials, for example, it may be partially fabricated from a spring steel, Nitinol, polymers, or other memory material that will allow a thin, flat barrier to be reconfigured into a more condensed configuration for passage through a straight needle [23*d*], after which it returns to its desired shape [23*c*] upon exiting the needle 2. The barrier 134, optionally, may be steerable.

As is illustrated in FIG. 24, correct anatomic placement of the backstop device 134 may be validated via monitored electrical neural stimulation through the barrier device 134. Electrical nerve stimulation function may be added to the apparatus via dual conductive elements, the first conductive element 104 for neural stimulation and localization placed on the working side (e.g., on the surface) of the backstop (or the tool used on the working side or the epidural endoscope tip), where tissue remodeling and resection will occur. The neural stimulation delivery box 114 can be attached to the ground electrode 116. In the example illustrated in FIG. 23, the working nerve stimulator on the working side of the barrier may be integrated with the rail 128, through which nerve stimulation may be tested before sliding the tool or sleeve over the rail for tissue modification. A conductive element (e.g., for neural stimulation) may also be placed on the non-working side of the backstop 130. To gain accuracy in neural localization, the stimulation leads on the device are separated by insulation material within the backstop material.

The patient may be kept awake and responsive throughout this procedure, with no neuraxial anesthetics and no systemic analgesia. In this manner, the medical practitioner may, through verbal questioning, elicit responses from the patient in order to ensure that any severe pain that would accompany undue pressure on the nerve root 62 during placement of the tissue modification device and/or during tissue removal or remodeling is immediately recognized prior to nerve injury. Alternatively, for a deeply sedated patient, or one under general anesthesia, nerve stimulation may be monitored via SSEPs or SEPs; visually (motor movement of extremities); via MEPs; and/or via EMG (motor stimulation). In one embodiment of the device, one might use a calibrated sensor, combined with computer analysis, to accurately quantify neural stimulation at different locations, in order to more accurately localize neural structures.

As is illustrated in FIG. 24, there should be no nerve root 62 or dorsal root ganglion stimulation in the exact location where tissue alteration is intended to take place, when one sends appropriate small electrical current through an insulated electrode that is located on the working side of an insulated working barrier, prior to tissue modification tool placement. Correct neural location, relative to the tissue modification tools and barrier may further be ensured by the addition of focused neural stimulation functionality to accompanying surgical instruments. For example, tools used for probing, tissue resection, tissue cauterization, thermal treatment, tissue lasering, tissue manipulation, tissue retraction, and tissue abrasion may contain conductive elements for neural localization 104. The nerve stimulation capabilities may be used to ensure that the neural elements are not in dangerous proximity, or they may be used to assist with more concise neural localization. For instance, a probe fitted with neural stimulation capabilities in its tip may be used to identify neural structures, through monitoring of sensory or motor stimulation. However, electrical stimulation on the non-working surface of the working barrier, which is in direct or indirect contact with neural structures, should result in motor and/or sensory action potentials, which may be monitored as described above, thereby providing a positive control and assurance of proper barrier placement. For added safety, a surgical device may be designed to automatically stimulate before or during resection, and may even be designed to automatically block resection when nerve stimulation has been sensed.

In a preferred variation, impinging spinal tissue is removed using tissue abrasion apparatus and method. Variations of the apparatus and method may be utilized during an open surgical procedure(s); during an endoscopic surgical procedure(s); or via a percutaneous (needle delivered) surgical approach. Use of a needle-based posterior interlaminar or interspinous approach, a posterior-lateral neuroforaminal approach or a minimally-invasive surgical approach for placement of the neuroforaminal abrasive tissue removal device avoids unnecessary tissue resection and minimizes tissue injury. In addition, further embodiments of the device include nerve stimulation and monitoring capabilities, which, when added to a spinal tissue alteration device, may enable the surgeon to more safely perform the procedure.

Figure 25:
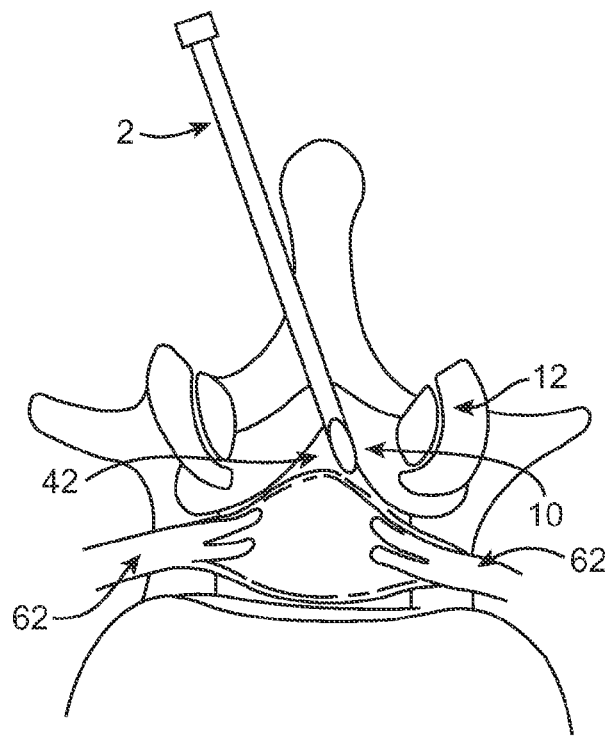
FIGS. 25-32 are cross-sectional views through a patient's spine, illustrating a method and apparatus for placement and use of elements for selective surgical removal of tissue.
Figure 26:
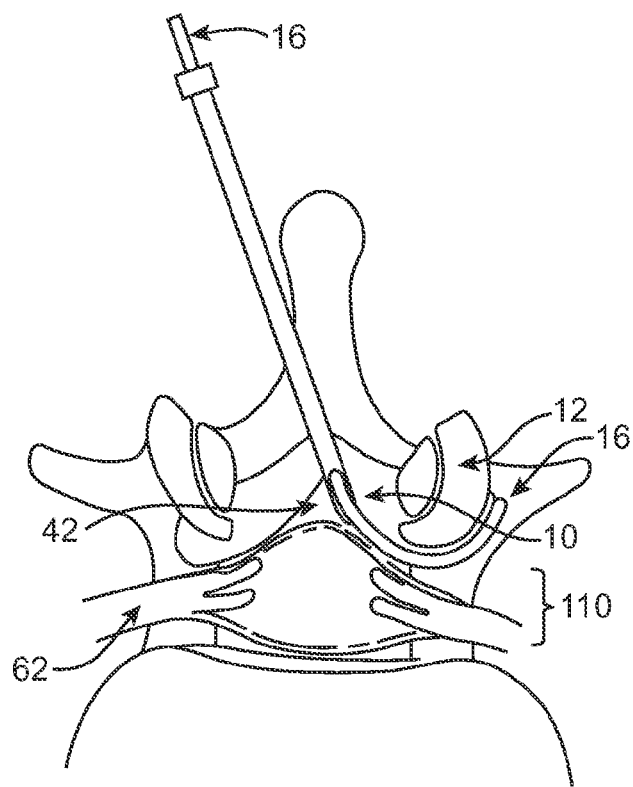
Figure 27:
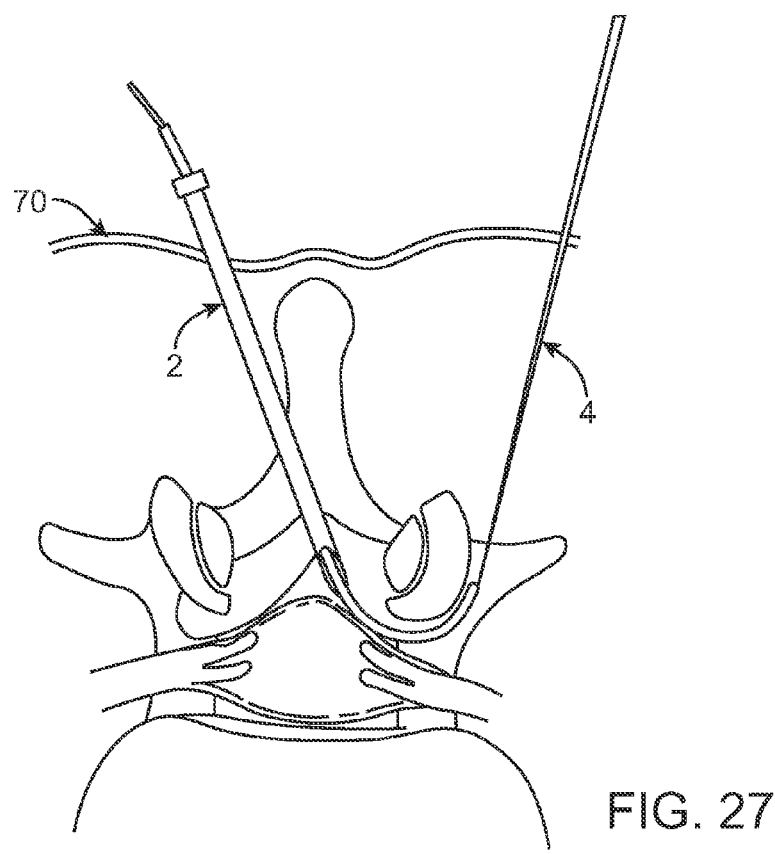

FIG. 25 shows the needle tip anterior to the ligamentum flavum 10, but still posterior to the dura 46 in the posterior epidural space 42. FIG. 26 illustrates a preferred method of cannulating the neural foramina, where a blunt, curved needle composed of memory material 16 is passed through the straight epidural needle 2 (alternatively, a stiff epidural catheter 24, or steerable guidewire may be inserted through the needle for this step). The curved needle 16 is flexible enough to be passed through the straight epidural needle 2, but is made of a memory material that returns it to its curved configuration upon when it is passed into tissue. The second needle 18 (alternatively, a steerable, stiff catheter, needle or guidewire), is advanced through the epidural space 42, possibly passing through a portion of the ligamentum flavum 10, towards and then through the ipsilateral or contralateral neural foramen 110. The surgeon may use any combination of tactile feel, image guidance, direct visualization, and/or fiberoptic visualization to ensure that the curved element 16 is driven through the neural foramen 110, anterior to the facet (zygapophysial) joint complex 12, but posterior to the nerve root 62 or ganglion. Once the curved element is in position through the neural foramen 110, the surgeon subsequently passes a smaller gauge straight and sharp flexible wire 4 (or needle), as in FIG. 27 through the lumen of the larger curved needle that is in position through the neural foramen 110, until it exits into the tissue lateral to the neural foramen 110 (FIG. 27). This straight wire 4 or straight needle exits the curved element with its tip facing in a posterior or posterior-lateral direction. It is advanced further in this direction, passing to, and then through the skin of the patient's back 70, as in FIG. 27.

Studies and tests may be performed to ensure that the transforaminally placed apparatus has been properly positioned between the nerve root 62 or ganglia and the facet joint complex 12. For example, imaging of the abrasion element and spinal anatomy (fluoroscopic or other imaging modalities); monitored neural stimulation through the apparatus; or direct (endoscopic or open) visualization may be utilized.

Figure 28:
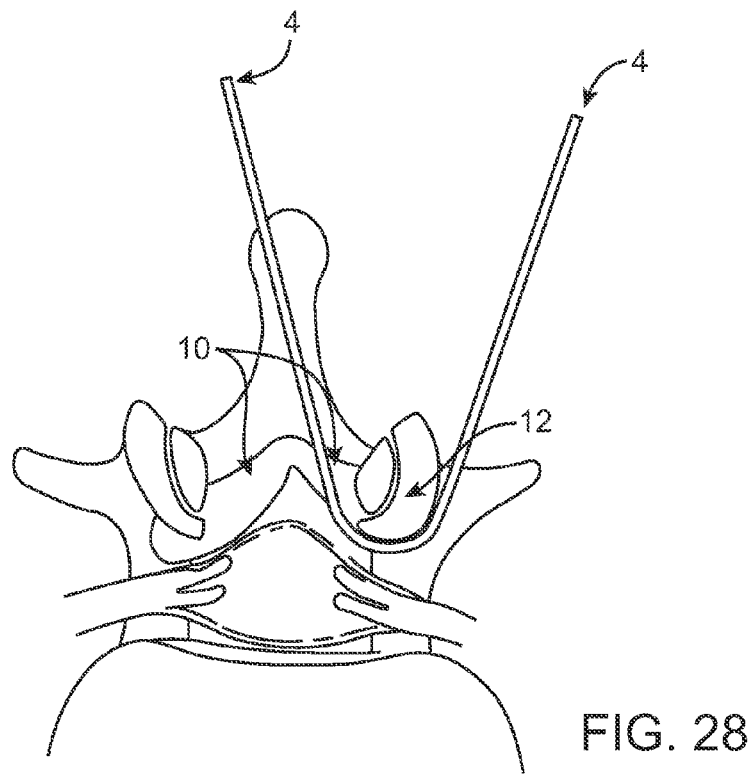

After proper placement has been confirmed, the curved element 16 that was used to initially cannulate the neural foramen 110 is removed, by pulling it back out of the hub of the epidural needle 2, leaving the transforaminal wire 4 in place, as illustrated in FIG. 28. Next the epidural needle 2 may also be removed, if desired, again leaving the wire 4 in its position, through the neural foramen 110. As shown, both ends of the element remain external to the patient, having exited the skin (percutaneous procedure) or exited the tissue through the surgical wound (open procedure).

Figure 29:
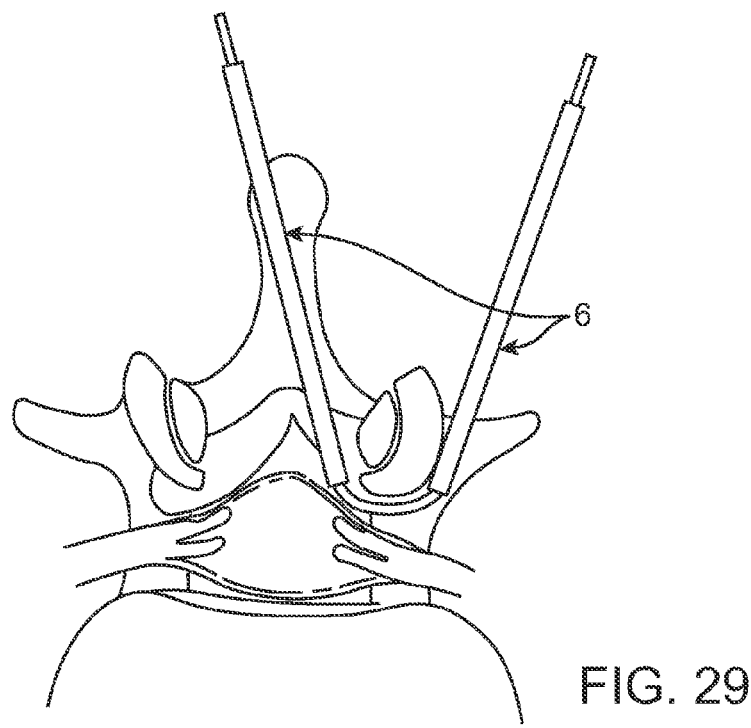
Figure 30:
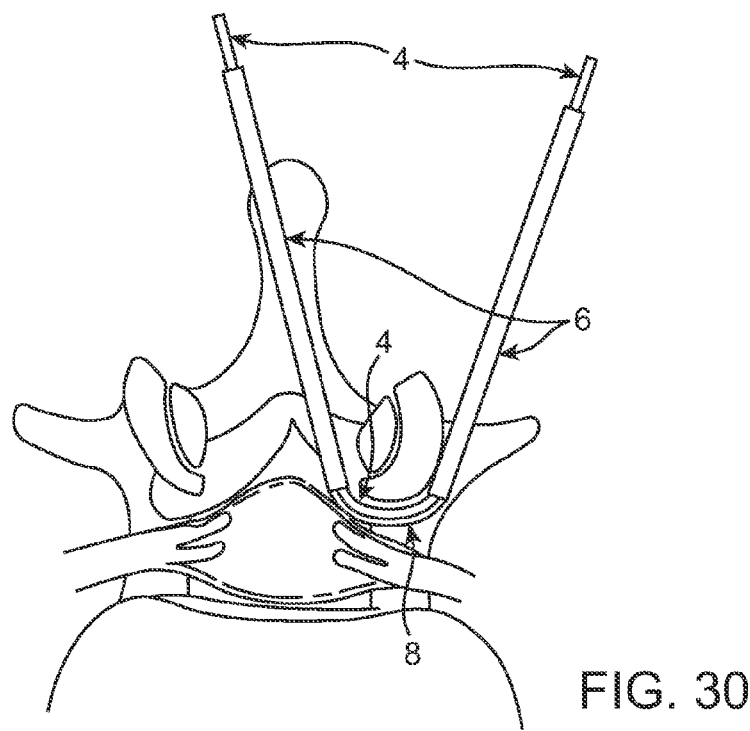
Figure 31:
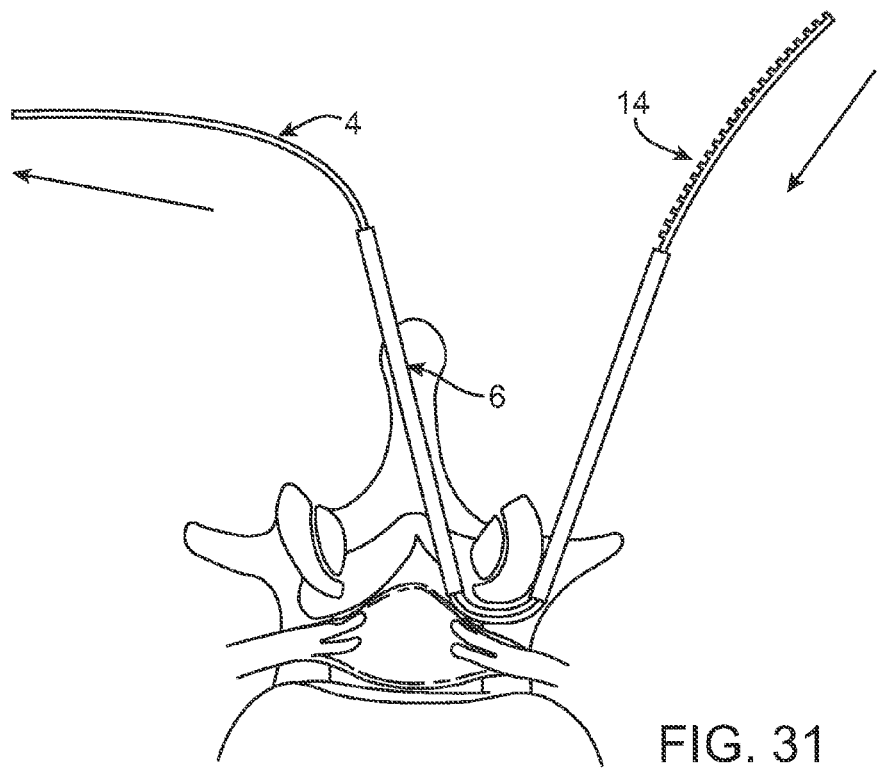
Figure 32:
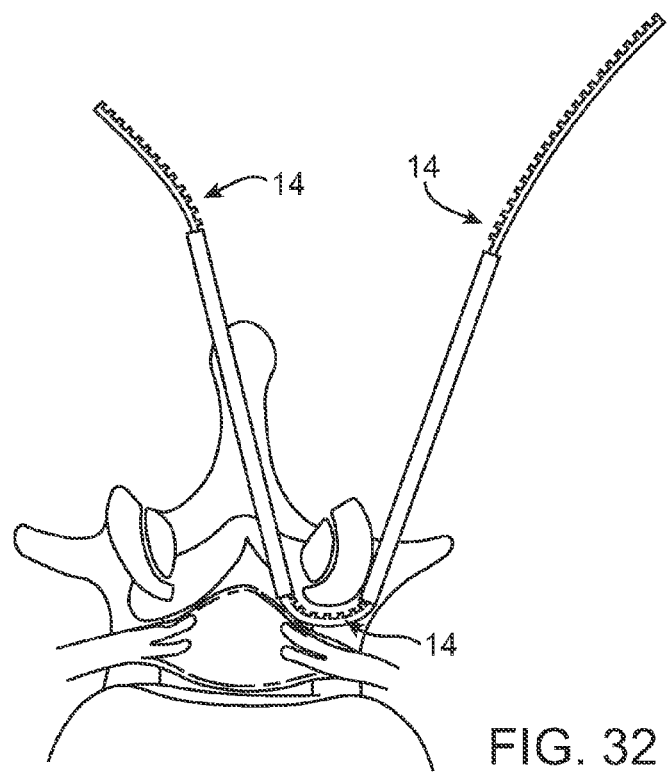
Figure 83A:
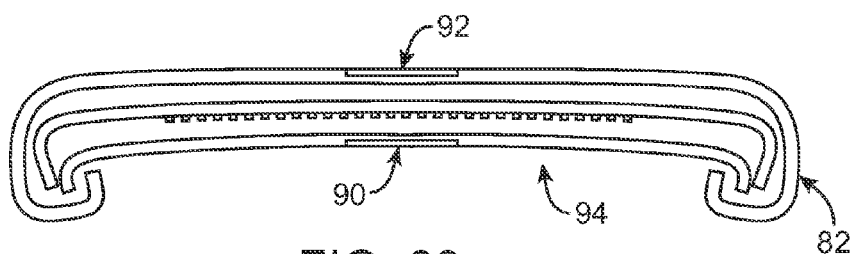
FIG. 83 are schematic cross section views of additional apparatus that may be utilized for selective surgical removal of tissue.
Figure 83B:
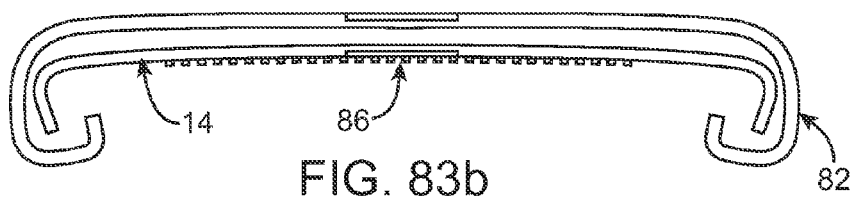
Figure 83C:
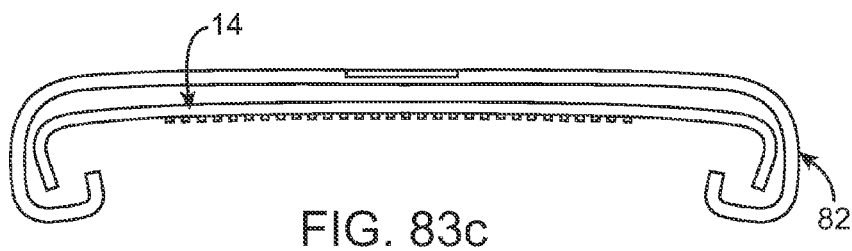
Figure 84A:
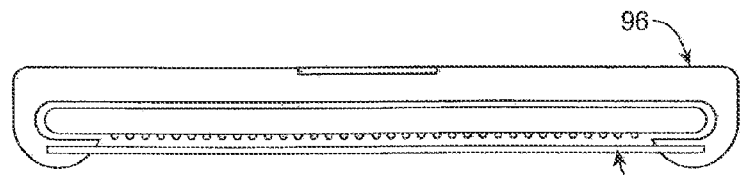
FIG. 84 are schematic cross section views of additional apparatus that may be utilized for selective surgical removal of tissue, and subsequently as a compression dressing, with the ability to act as a therapeutic drug depot.
Figure 84B:
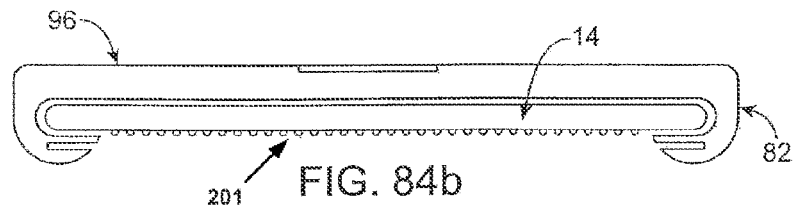
Figure 84C:
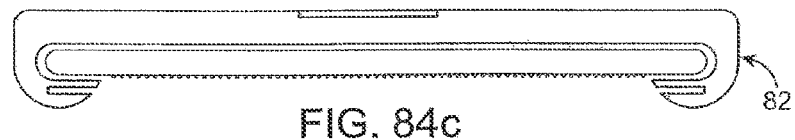
Figure 84D:
Figure 84E:
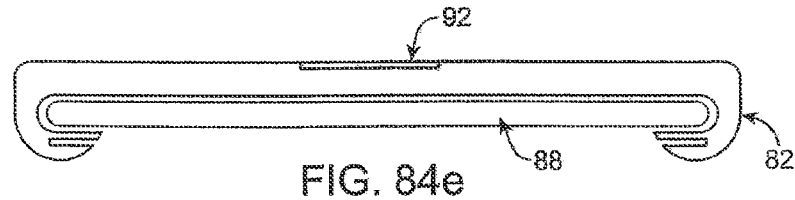
Figure 84F:
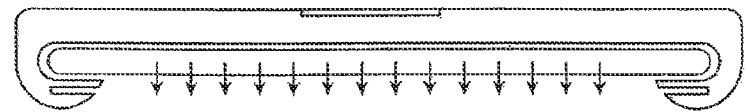
Figure 84G:
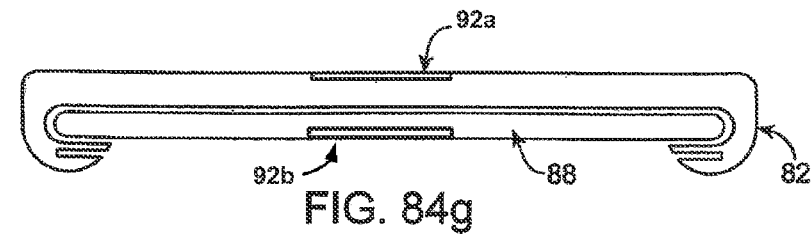

With the wire in position through the neural foramina, there are multiple possible methods for replacing the wire with the abrasion apparatus. One method is illustrated in FIGS. 43-45, where the wire 4 is used to pull into position the abrasion element 14; the abrasion element sleeve or cover 6; or the abrasion element 14 and cover 6 together, as is described in greater detail below. Alternatively, as shown in FIGS. 29 and 30, separate protective sleeves or covers 6 may be passed over both the proximal and distal ends of the transforaminal wire 4. Each sleeve or cover may be advanced to the neural foramen 110. Next, the neuroforaminally placed wire 4 is connected distally, or proximally, to the abrasive element 14, with an abrasive surface on one side. The abrasive element 14, connected by one end to the transforaminal wire 4, is pulled through the neural foramen 110, and through the protective sheaths or covers 6, as in FIGS. 31 and 32, until the abrasive element 14 has completely replaced the initially placed wire 4 (or needle). Passage of a tissue dilator over the transforaminal wire 4 or needle, may be helpful, either before or after placement of the sleeve. Protective sleeve(s) 6 illustratively are disposed over both ends of the transforaminal wire 4, in order to protect non-surgical tissues from the abrasive or cutting portion of the device, when it is pulled into place. Alternatively, a protective abrasive element sleeve 98, which may be expandable, as illustrated in FIG. 83, may be attached to the end of the wire and pulled through the neural foramina, thereby replacing the initial transforaminally placed element. The abrasive element sleeve 98 covers the abrasive element in tissue and is a conduit for insertion and exchange of abrasive elements.

In an alternative preferred embodiment, the abrasive element 14 is positioned within the protective sleeve cover 6, before or after placement of the abrasive element in position through the neural foramina. Please note that the terms "protective sleeve" and "protective cover" are used interchangeably in these descriptions of several examples of the apparatus and methods for protecting vulnerable tissue from the abrasion apparatus. Embodiments of the protective methods and apparatus are illustrated in FIGS. 82-85. With the abrasive element 14 already inside the protective apparatus 6 or 96, with or without an opening over the abrasive surface where tissue abrasion is to be performed the protective covering, with the abrasive apparatus already inserted within it, may be connected to one end of the needle or guidewire that remains in place through the neural foramen 110. In this preferred method, the combined protective sleeve and 6 the abrasive element 14 are then pulled simultaneously through the neural foramen 110, by pulling from the opposite end of the preliminarily placed neuroforaminal element, while it is removed. A conductive element 90 for neural stimulation can be on the working side of the apparatus.

Once the abrasion apparatus has been properly positioned through the neural foramina, with its protective cover in place, it is ready to be tested to ensure it has been properly located. The apparatus may subsequently be utilized for tissue abrasion, tissue removal, and tissue remodeling, as will be described in detail below. Before describing tissue modification in further detail, however, we will describe alternative approaches for placement of the abrasion device into position through the neural foramina.

Figure 33:
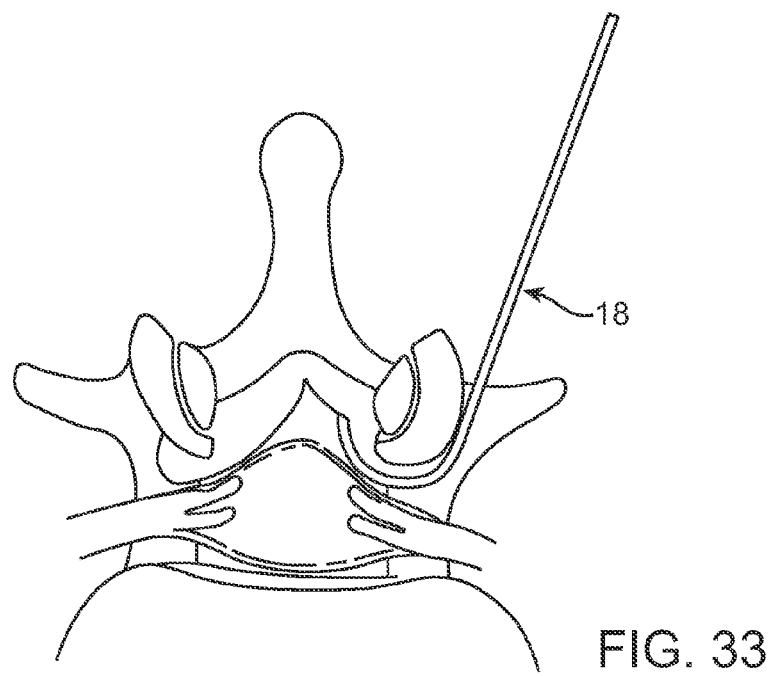
FIGS. 33-36 are cross-sectional views through a patient's spine, illustrating a variation of the method and apparatus of FIGS. 25-32.
Figure 34:
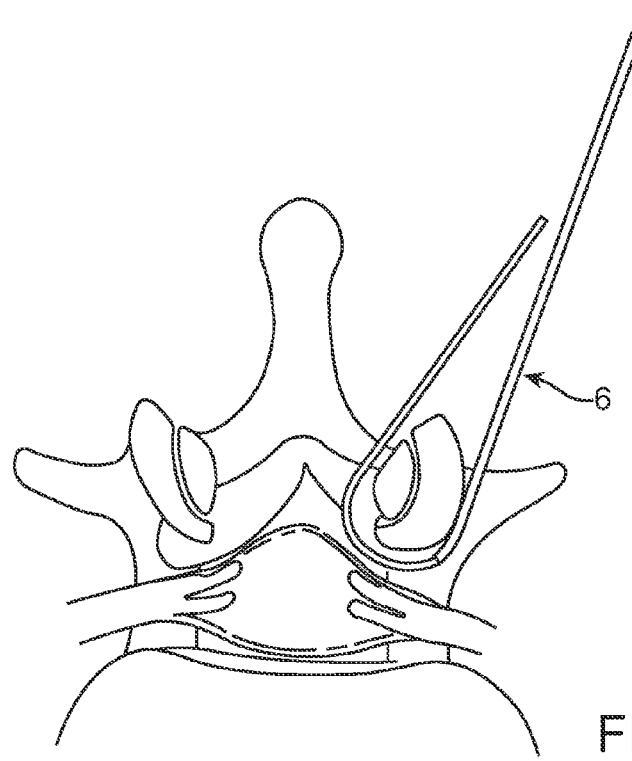
Figure 35:
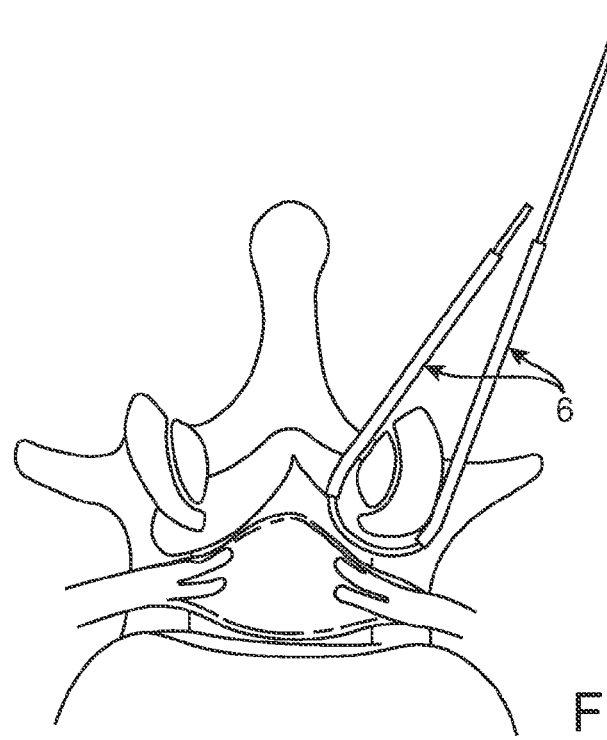

Referring now to FIGS. 33-36, a variation of the method and apparatus of FIGS. 25-32 is described comprising an alternative approach for placement of the tissue modification device, wherein the apparatus 14 is placed from the lateral side of the neural foramen 110. As seen in FIG. 33, a steerable or needle wire 18 is placed through the neural foramina 110 from the lateral towards the medial side of the foramen 110.

Figure 36:
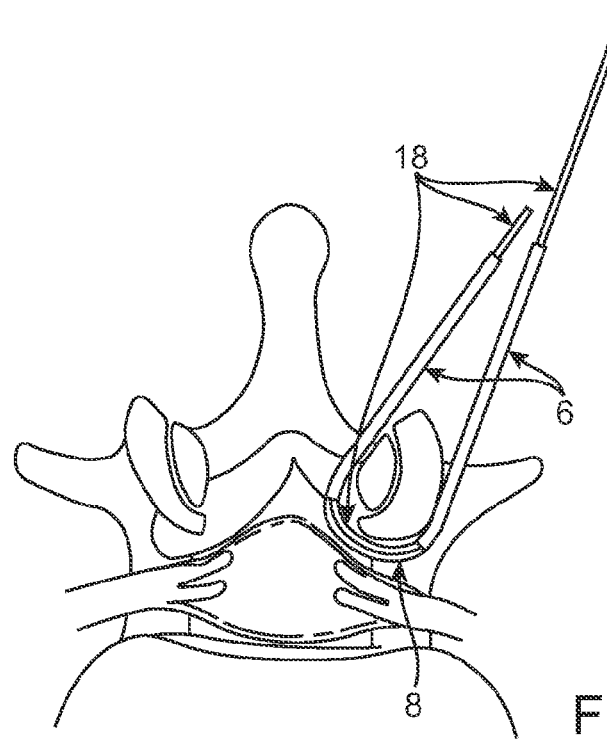

This lateral to medial neuroforaminal approach may begin with a curved, blunt wire through a straight needle (as described in the previous technique), or using a curved needle technique, a steerable guidewire technique, a needle-through-a-needle technique, or common variations thereof. FIG. 36 illustrates that the protective sleeve 6 or cover can have a neural barrier portion 8 for the abrasion element. While a loss of resistance technique is not as helpful with this transforaminal approach to the epidural space 42, as it was in the previously described posterior approach to the epidural space 42, the method is, in many other aspects, otherwise similar to the method illustrated in FIGS. 25-32.

Figure 37C:
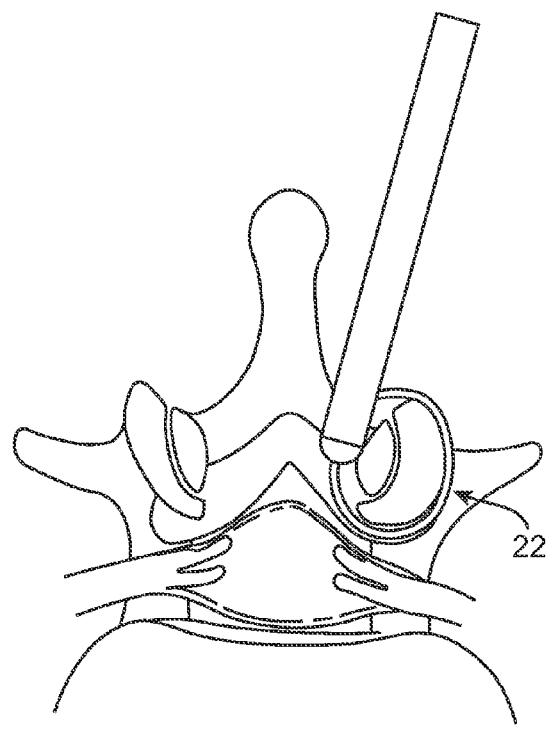
Figure 37D:
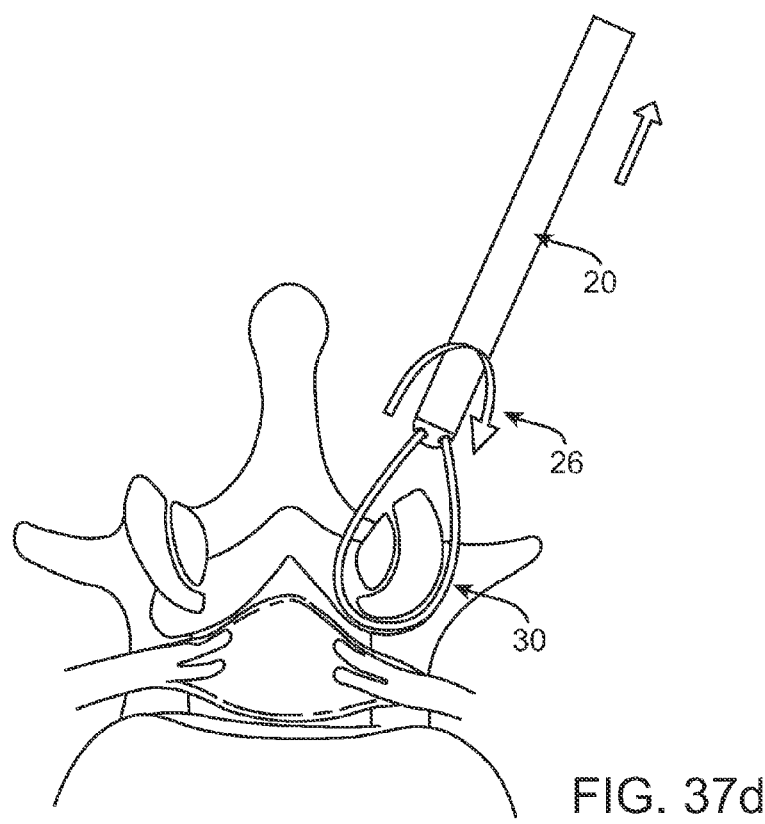
Figure 38:
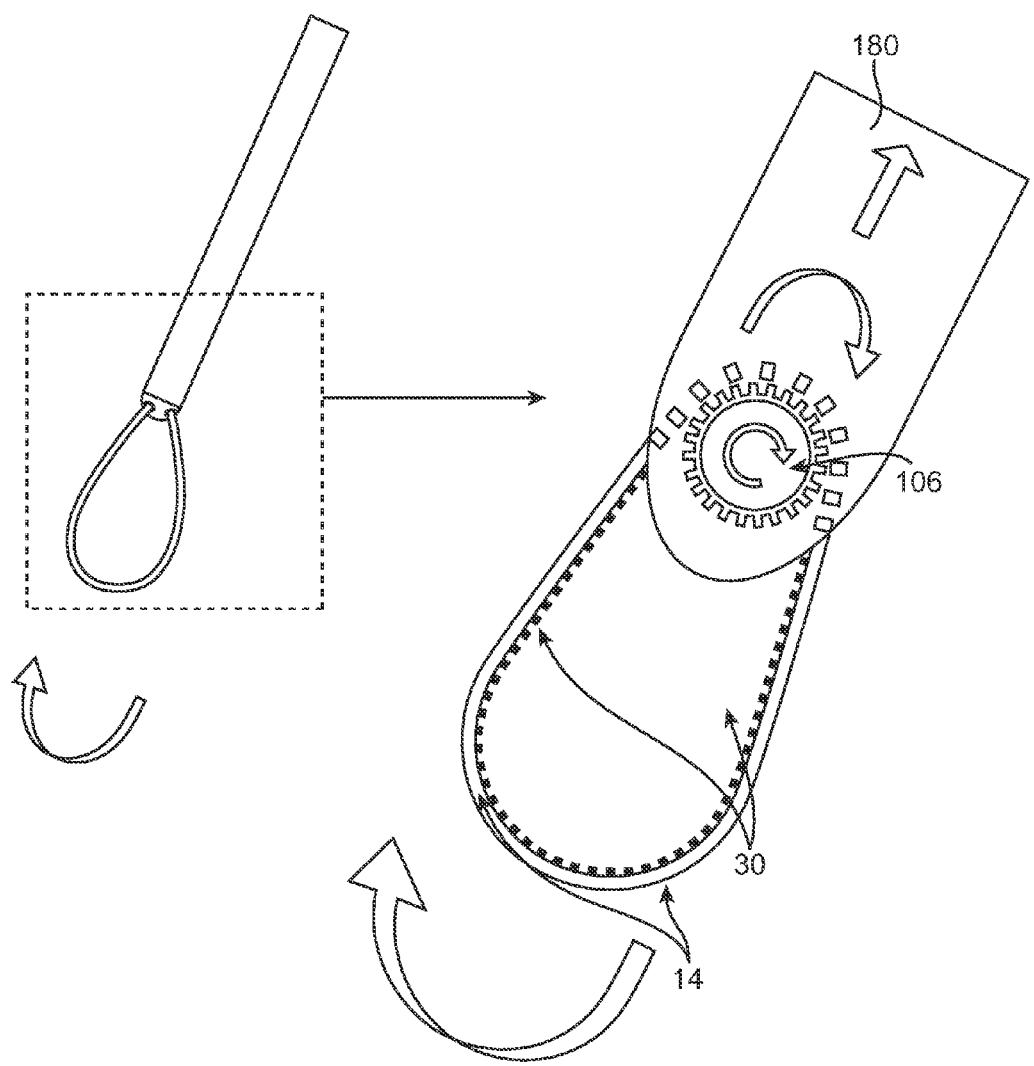
FIG. 38 are a detailed view and a close up of the cross section of a preferred embodiment of the apparatus used in FIG. 37d.
Figure 39:
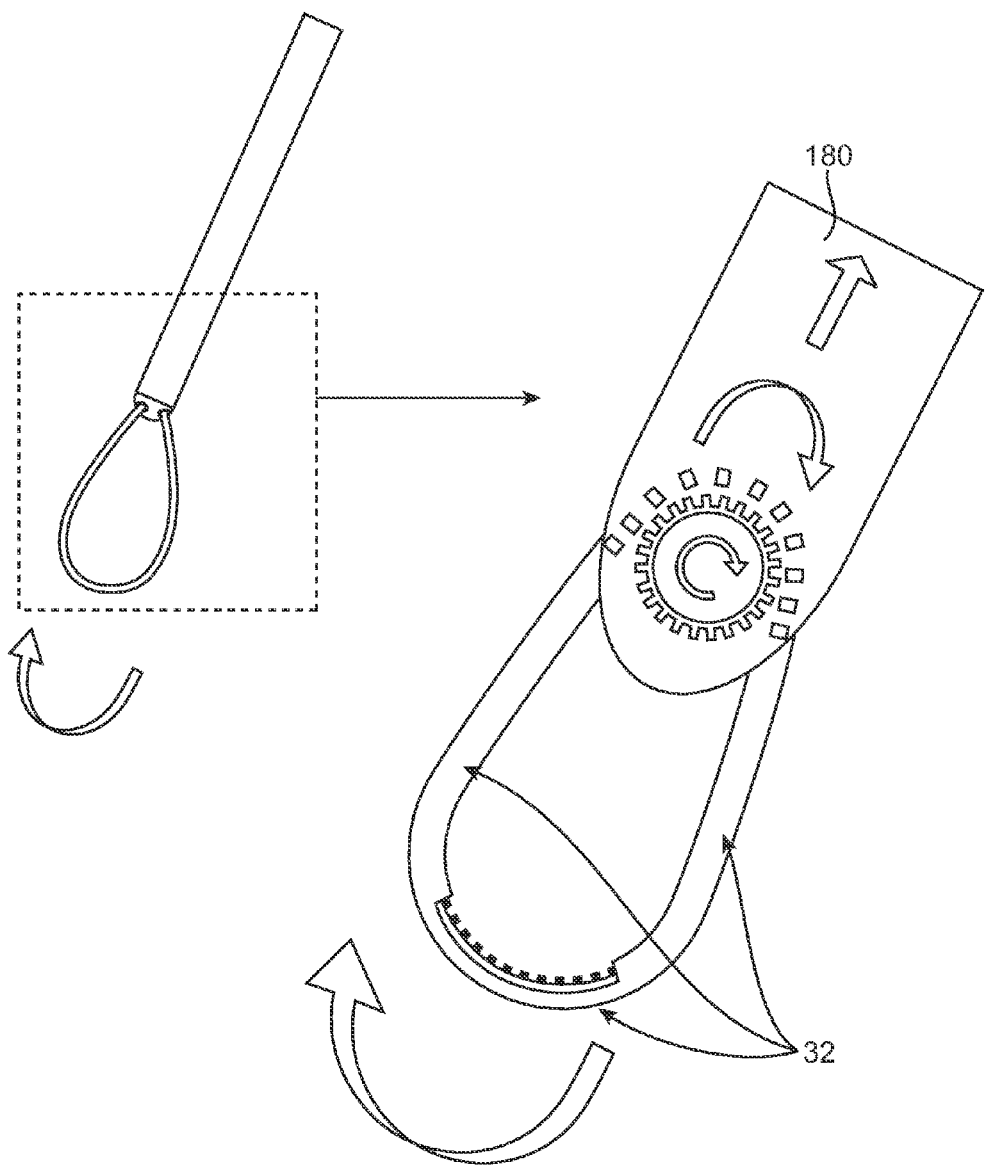
FIG. 39 an alternative embodiment of the apparatus of FIG. 38.

With reference to FIGS. 37 a-e, another variation of the method and apparatus of FIGS. 25-32 is described. In FIG. 37a, the apparatus 20 is placed from an interlaminar; a translaminar, interspinous; or a transforaminal insertion, illustratively via a paramedian, ipsilateral approach. A lateral to medial transforaminal approach with the same type of apparatus may alternatively be used. The blunt or rounded distal tip of apparatus 20 optionally may be somewhat sharper, to facilitate placement. The apparatus 20 may be preceded by a guidewire, a dilator, or a needle introducer (possibly with or followed by an expandable sheath). This variation of the apparatus and method, as seen in FIG. 37b, contains a rigid, curved wire or needle 22, which may be steerable, which is driven from the tip of the apparatus 20, laterally through the neural foramen 110 and then posteriorly, around the facet joint complex 12 and back towards apparatus 20, where the needle may be received once again by the apparatus. Arrow 26 in FIG. 37d illustrates the direction of movement of the abrasive element. FIG. 38 provides a cross section through apparatus 20 that illustrates an exemplary geometry for the apparatus comprising a feature that facilitates receiving of the distal end of the needle or rigid guidewire back within the apparatus. Alternative geometries will be apparent. Once received back within apparatus 20, the wire 22 completely encircles the facet joint 12, as in FIG. 37c, d. In FIGS. 37d, 38, and 39, guidewire 22 has been replaced by tissue abrasion device 32, e.g., a belt, strap or ribbon, preferably within a protective sheath or cover, with the abrasive surface of the device in contact with the anterior-medial facet complex. Apparatus 20 is pulled back, bringing the working surface (exposed abrasive portion) of the instrument into firm contact with operator controlled pressure against the surface from which tissue removal will occur. Neuroforaminal enlargement begins with the movement of the abrasive surface 30 against the anterior and medial portion of the facet complex 12, in the lateral recess and neural foramen 110. The abrasive surface 30 can be of an abrasive element in an electromechanical abrasion device.

With reference to FIG. 38, an enlarged view of the mechanical portion of apparatus 20 is described. An abrasive surface 30 is disposed along the inside side of tissue abrasion element. The abrasion device may be actuated, e.g., via rotation of a gear 106 within the apparatus 20. The gear or knob 106 engages with the abrasive element, and is turned to provide movement of the abrasive element within the apparatus. Debris may be captured within apparatus 20, and stored in the shaft and/or handle 68, or removed continuously during the procedure. The debris can be sent in the direction of arrow 180 for removal or storage.

Referring now to FIG. 39, a variation of the apparatus of FIG. 38 is described comprising an additional protective cover 32 that covers one or more sides of the abrasive elements 14 of the device 20 in all regions except for the area covering the tissue where abrasion is to take place. This cover may contain a conductive element in order to enable nerve stimulation 130 and/or to facilitate neural localization 104. Nerve stimulation capabilities may be present on the internal abrasive surface 30 of device abrasive element 14, and/or on the external side (non-tissue abrading) of the device, as an added safety measure. For example, the user may send an electric impulse through a conductive element within the back-side (external surface) of the device, expecting to achieve neural stimulation when the device is in place through the neural foramina, while neural stimulation should not be achievable with a similar electrical impulse conducted across a portion of the abrasive side of the device. In this manner, information from monitoring the nerve stimulation may ensure proper placement of the abrasion device and reduce a risk of inadvertent neural or perineural vascular abrasion.

Figure 40:
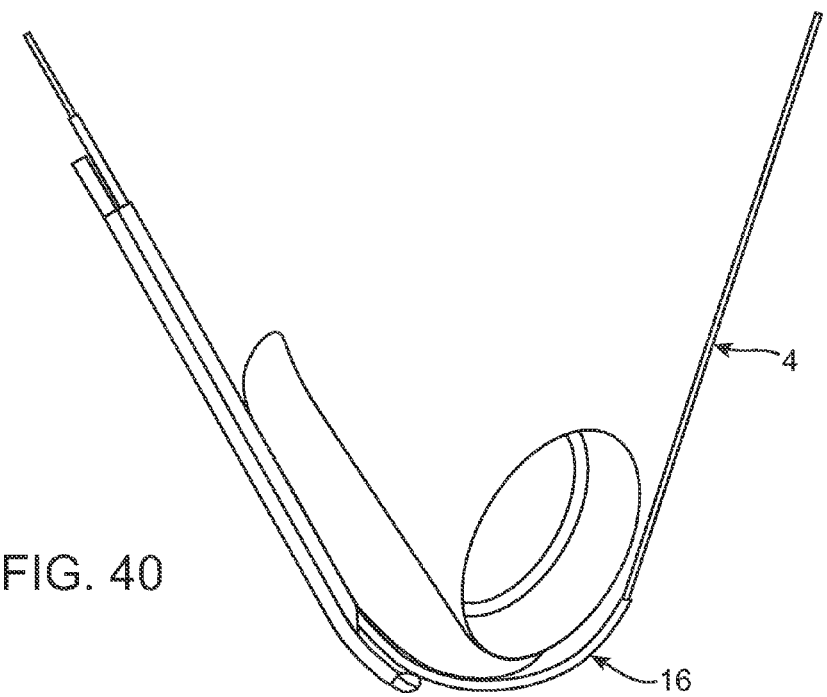
FIGS. 40-45 are partial cross-sectional views through a patient's spine, illustrating a method for use with single or multiple lumen delivery systems, for placement of an abrasion apparatus through the neural foramina for selective surgical removal of tissue.
Figure 41:
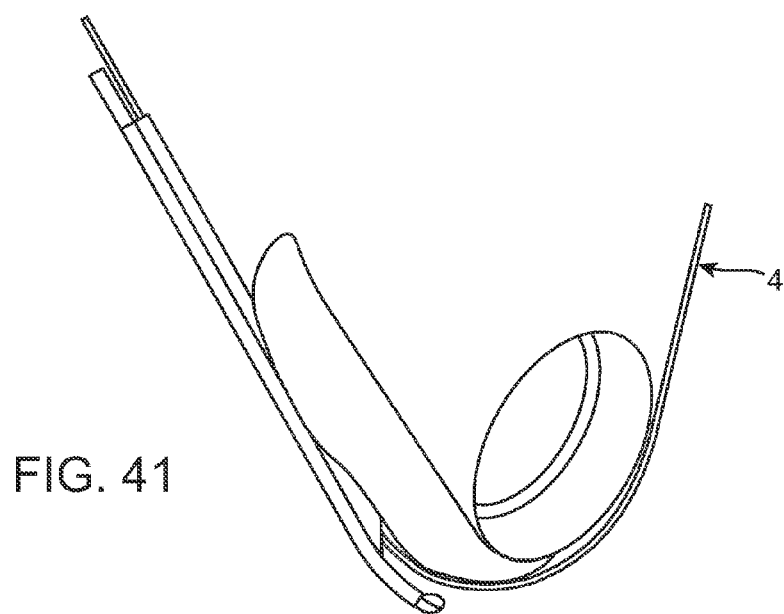

In FIG. 40, straight wire or needle 4 is driven through curved needle 16 disposed in working channel 50 of double barrel epidural needle 164. This straight wire or needle is advanced until it has penetrated through the skin and out of the patient's body. The straight wire preferably has a sharp tip. In FIG. 41, the curved needle 16 has been withdrawn from working channel 50, leaving straight wire or needle 4 in place. Then, as seen in FIG. 42, the epidural needle 2 and working channel may be withdrawn from the patient, or, in an alternative embodiment (FIG. 14b), when using a detachable working channel 50, the working channel alone may be withdrawn from the patient, leaving straight wire 4 in place. In FIG. 43, straight wire 4 has been hooked to abrasion device 14 and/or the abrasion device's protective sleeve 6. In FIG. 44, the abrasion device 14 and/or the device's protective sleeve are pulled into position by wire 4 as the wire is removed. In FIG. 45, wire 4 has been completely removed, and the abrasion device 14 and its protective sleeve 6 are properly positioned for tissue resection, anterior to the facet 12 and ligamentum flavum 10.

In an open surgical variation, the abrasive element 14 and its cover 6 may be placed through the surgical incision, from a interlaminar, translaminar, or neuroforaminal approach. Visualization and placement may be aided via partial or complete laminectomy, facetectomy, or ligamentectomy. Methods for threading the neural foramina include, but are not limited to the use of a wire, blunt needle, probe, endoscope, or suture. After spinal neuroforaminal placement, the abrasion device 14 is used to selectively remove tissues that impinge on the neurovascular structures within the lateral recess 108 and neural foramen 110, on the anterior side of the facet joint 12. In an open approach, as with a percutaneous approach, the device may be inserted through a needle, optionally under image guidance or with the aid of an epidural endoscope. Once placed through the neural foramina 110 of the spine, around the anterior border of the facet joint 12, and anterior to the ligamentum flavum 10, the medical practitioner may enlarge the lateral recess and neural foramina via frictional abrasion, i.e., by sliding the abrasive surface across the tissue to be resected (e.g., far lateral ligamentum flavum 10, anterior and medial facet, osteophytes). The abrasion device alternatively or additionally may be placed through the neural foramen 110 anterior to the facet joint 12, but through or posterior to the ligamentum flavum 10. The medical practitioner controls the force and speed of the abrasive surface against the tissue to be removed, while optional protective covers, tubes or sleeves 6 help limit the area exposed to the abrasive element for treatment.

Figure 46:
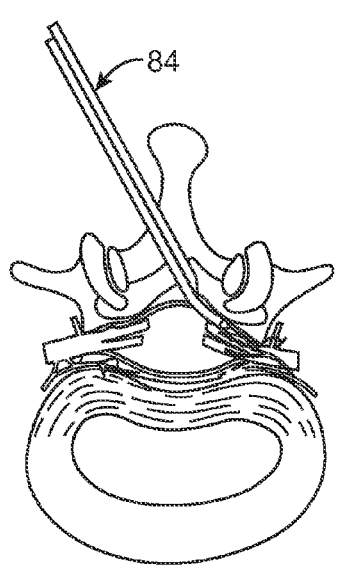
FIGS. 46-58 are cross-sectional views through a patient's spine, illustrating a variation of the methods and apparatus of FIGS. 40-45, which may also be used with single or multiple lumen delivery systems.
Figure 47:
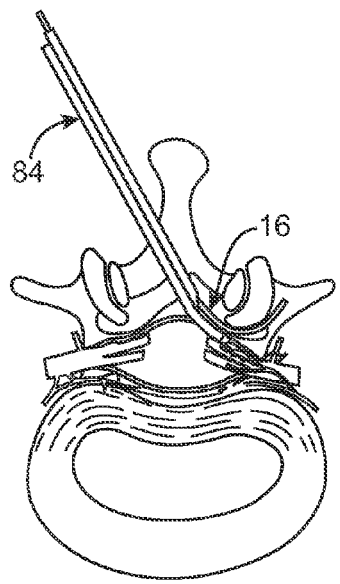
Figure 48:
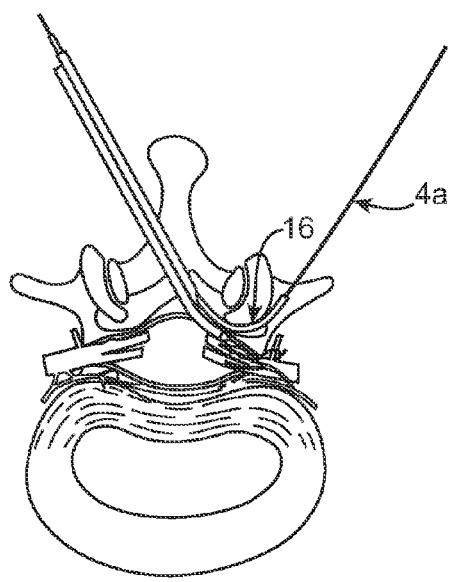
Figure 49:
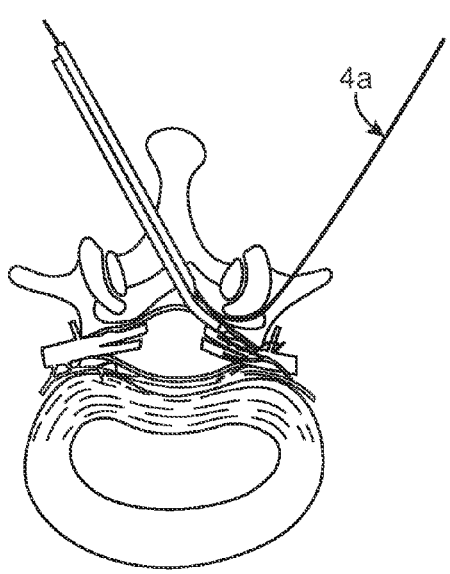
Figure 50:
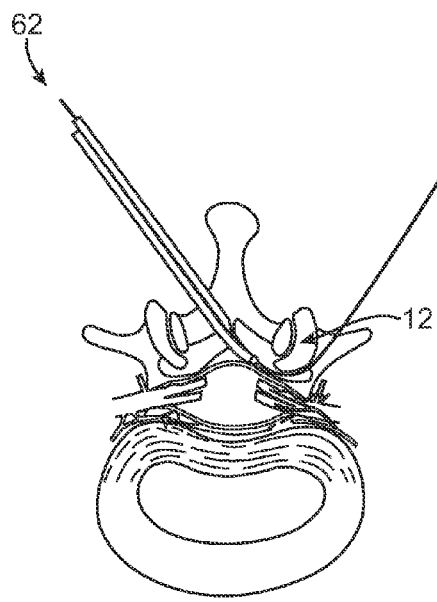
Figure 51:
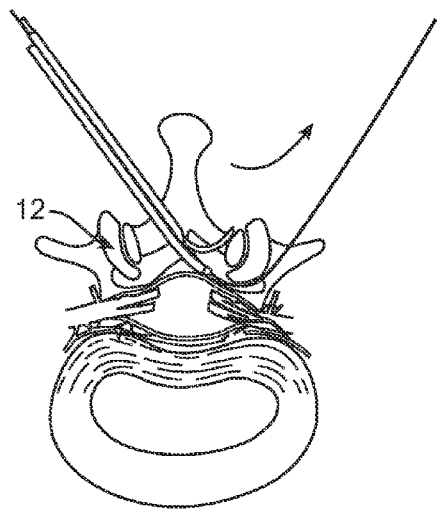
Figure 52:
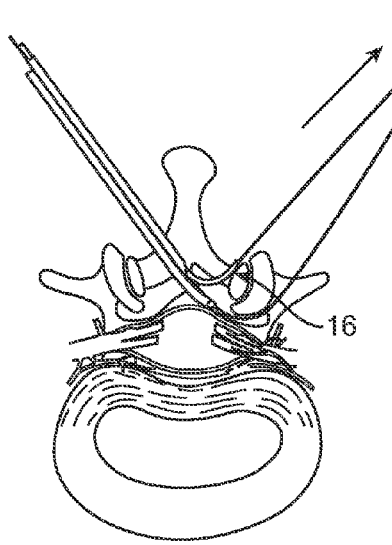
Figure 53:
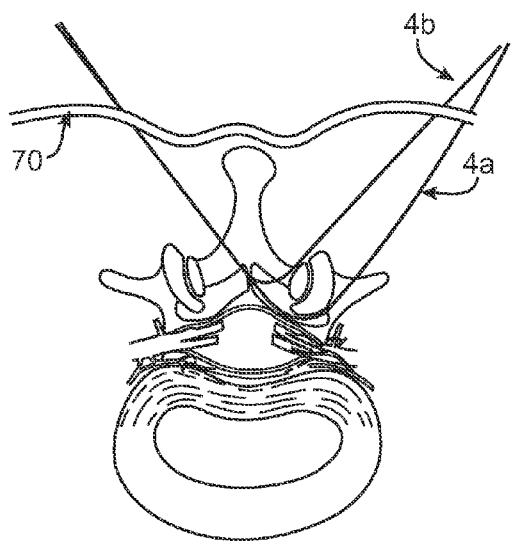
Figure 54:
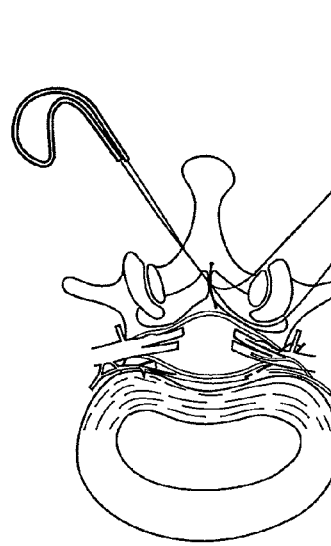
Figure 55:
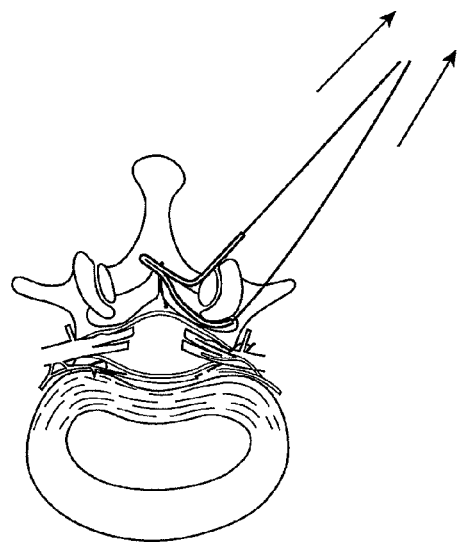
Figure 56:
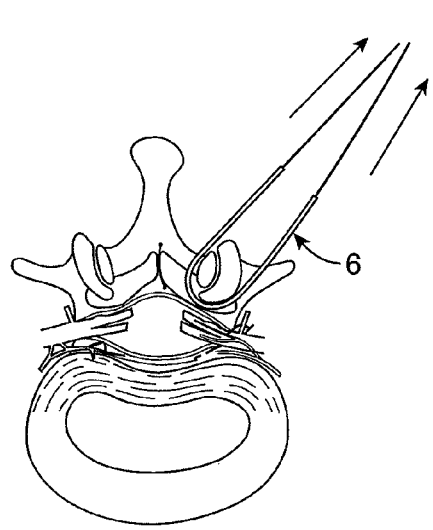
Figure 57:
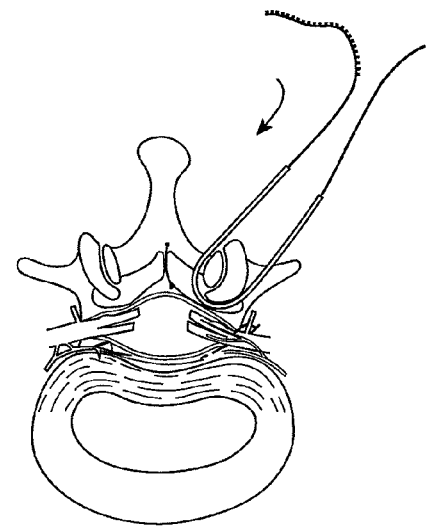
Figures 58, 59:
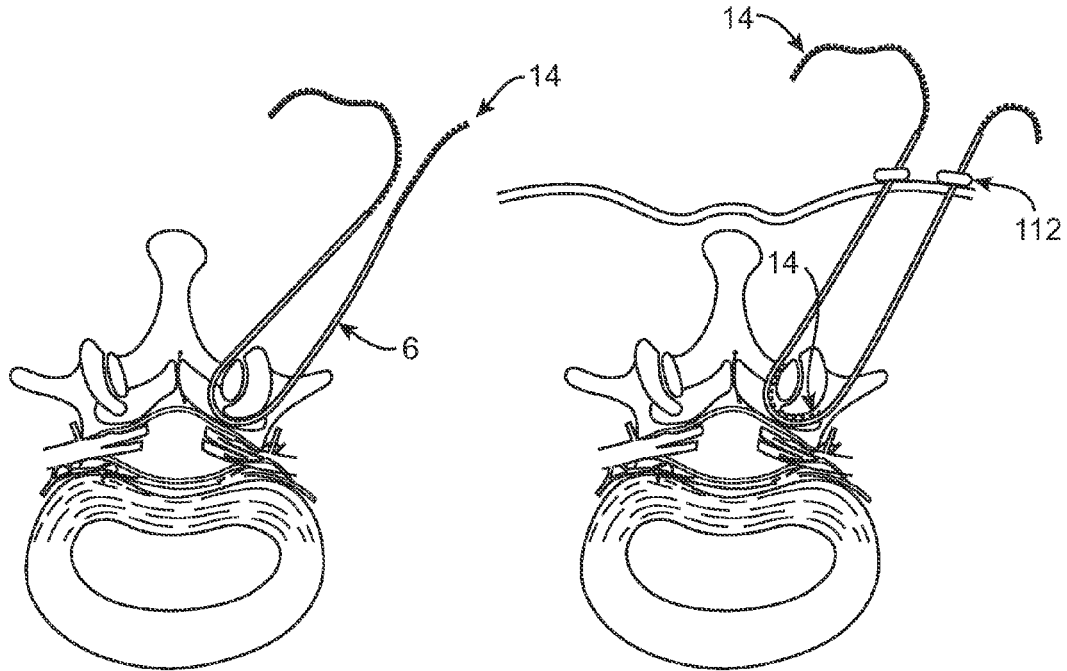
FIG. 59 is a cross-sectional view through a patient's spine, illustrating a methods and apparatus that, under tension, anchors and suspends the working sheath or protective sleeve that covers the neuroforaminal abrasion device.
Figure 60:
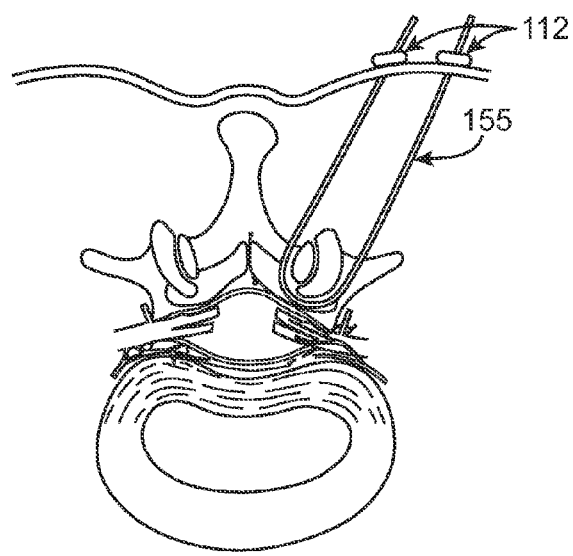
FIG. 60 is a cross-sectional view through a patient's spine, illustrating a method and apparatus that, under tension, provides a percutaneous compression dressing over the abraded area. In this illustration, the compression dressing is the same working sheath or protective sleeve that had covered the neuroforaminal abrasion device.
Figure 63:
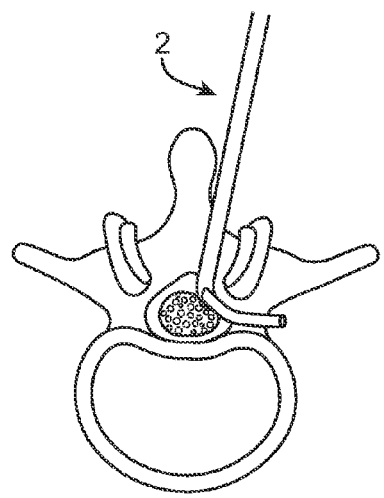
FIGS. 63-70 are schematic cross-sectional views through a patient's spine of a method and apparatus for a posterior midline or paramedian approach to placement of a posterior elements compression, retraction or retention device around the facet complex, through the neural foramina.
Figure 64:
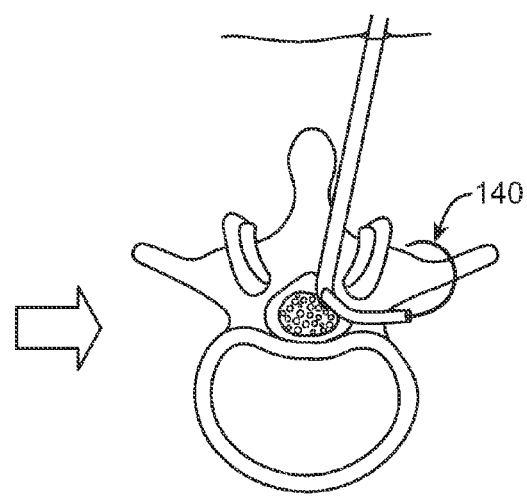
Figure 65:
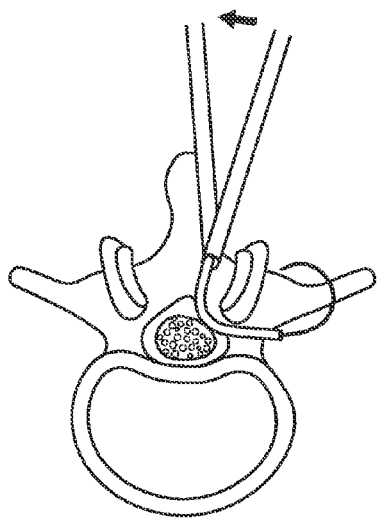
Figure 66:
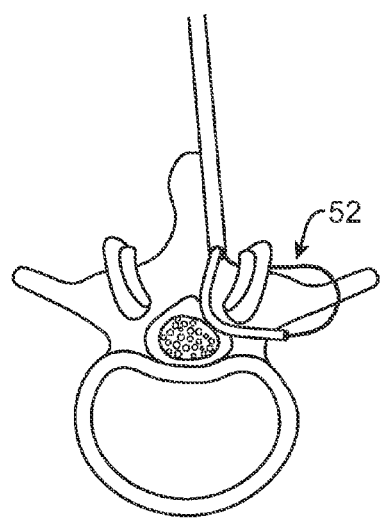

Referring now to FIGS. 46-61, a variation of the method and apparatus of FIGS. 40-45 is described, comprising another preferred approach for placement of the abrasion device. This series begins with FIG. 46, in which a double lumen, blunt tipped, epidural device 84, has already been advanced to the lateral recess 108, using a technique similar to FIG. 18. Next, FIG. 47 shows a curved flexible needle 16, preferably with an atraumatic tip, that has been advanced, via the working channel 50 (FIG. 15), through the neural foramina 110. FIG. 48 illustrates threading of the straight, flexible, sharp tipped wire 4a through the curved needle 16, and advanced posteriorly until it exits the skin of the back 70. In FIG. 49, the curved needle has been withdrawn, leaving the straight wire 4a in place. In FIG. 50, the double lumen epidural apparatus 84 is slightly withdrawn, from the patient, so that the working channel 50 is directed towards the medial side of the facet complex 12. FIG. 51 shows the curved needle 16 advanced through the working channel again, adjacent to the first wire 4a, this time advancing the same or a different curved, flexible needle 16, towards the opposite side of the facet complex 12. FIG. 52 shows where a second straight flexible wire 4b is advanced through the second placement of a curved needle 16, this time on the medial side of the facet joint. The second sharp, flexible, straight wire 4b is threaded through this second curved needle, and subsequently advanced posteriorly, until the sharp tip of the wire 4b exits the skin. FIG. 53 next shows both the curved needles and the double lumen apparatus removed, leaving the wires 4a and 4b in place. FIG. 54 shows that both wires have been attached to the two ends of the abrasive element and/or the cover 32 of the abrasive element. Alternatively, the two wires 4a and 4b may be opposite ends of the same continuous wire, with the cover 32 for the abrasive element already placed over the midportion of the wire 4. Alternatively, the abrasive element 14 may already have been placed inside said cover 32, and attached at each end to the wires 4a and 4b. FIGS. 55 and 56 show the two wires 4a and 4b pulled and bringing the abrasive element cover, possibly with the abrasive element 14 already placed inside said cover 32, into position through the neural foramina. FIG. 57 illustrates the step that follows placement of the abrasion element cover alone. In FIG. 57, with the wire in place inside the abrasion element cover 6, the abrasive element 14 is now seen to have been attached to the end of the wire. Subsequently, the cover 32 is held open at each end by a grasping device, which also holds the cover under tension against the tissue to be abraded. With the cover anchored thus, the abrasive element is pulled into place by the wire, replacing the wire, as has occurred for FIGS. 58 and 59. With the abrasive element in position and the abrasive element cover tightly held open and against the tissue to be abraded, the abrasion element 14 may be pulled back and forth, under tension, against the tissue to be abraded, as in FIG. 59. Alternatively, the abrasive element may be pulled in a single direction across the tissue to be abraded. FIG. 60 illustrates the cover following removal of the abrasive element. Said cover may remain in place as a compression bandage 168, under tension against the freshly abraded surface, in order to promote hemostasis, promote tissue remodeling, and trap debris post operatively. The compression bandage 168 can be a percutaneous retention and compression dressing or tissue remodeling strap, or a retention strap or belt.

A nerve stimulator may be incorporated into the abrasive surface of the abrasive element, and/or incorporated into the protective cover 88 or sheath for the abrasive element, in order to verify correct placement and enhance safety by allowing the medical practitioner to ensure that neural tissue is not subject to inadvertent abrasion. FIG. 61 illustrates a neural stimulation apparatus. FIG. 61 also illustrates an abrasion element 14, disposed inside of a sheath or cover 6, and held in place by tension retaining elements 112 (shown in FIG. 60). The skin anchor 112 for the abrasive element cover or sheath can hold the cover under tension, allowing the abrasive element to be moved freely within. The stimulation apparatus 114 (e.g., the neural stimulation delivery box) delivers a small electrical current through the working surface and/or the non-working surface (backside) of either the tools used in the epidural space 42, the abrasive element, and/or the protective cover of the abrasive element. Preferably, one electrode, or wire 120 to the electrode, would be connected to each side (abrasive and non-abrasive) of the entire device and sheath complex, along the full distance where tissue abrasion is planned to occur, in the lateral recess, central canal, or neural foramen 110. Neural stimulation may be monitored via verbal response to stimulation in an awake or lightly sedated patient, or SSEP, MEP, EMG, or motor evoked muscular movement in an asleep or sedated patient. One possible mechanism for avoiding inadvertent neural damage may be to ensure that there is no neural stimulation when stimulating the working surface of the device. A positive control should be obtainable in the lateral recess and neural foramen 110, when stimulating the non working surface (back side) of the device or, preferably, the backside of the device cover or sheath 172 (e.g., first portion of locking mechanism).

After the abrasion element, and possibly its protective sheath or cover [3, 49, 50], have been placed through the neural foramina 110 the abrasive surface is brought into firm contact with the tissue to be abraded by pulling tension simultaneously on each end of the abrasion element. When both ends of the abrasive element 14 are pulled simultaneously, the abrasive surface of the device is brought under tension and into firm contact with the impinging spinal tissue on the anterior and medial sides of the facet joint complex 12. Subsequently, one end of the abrasive element is pulled more forcefully than the other, sliding the abrasive surface is across the target tissue. When one end of the abrasive element is pulled with more force than the other, the ribbon moves in the direction of the stronger pull, while the lesser pull on the opposite end maintains force and creates friction with movement between the abrasive surface and the tissue to be resected. When the optional protective cover 6 or sheath is provided, both of its ends of the are, in one variation, pulled under traction and anchored in place, such that the abrasive element 14 may be pulled in either or both directions through the cover 6 or sheath without significant friction against and/or without causing trauma to adjacent tissues.

Alternatively, the abrasive element 14 may be pulled in a single direction across the tissue. The abrasive belt, strap or ribbon may be a single length, pulled alternately in each direction, or it may be dispensed from a spool, as in FIG. 62a, or from a reel to reel configuration, as in FIG. 62b, and pulled in both directions or pulled in a single direction, across the tissue to be abraded. An alternative variation of the apparatus and method utilize an electromechanical, belt driven abrasive tool, an example of which was described previously in FIGS. 38 and 39.

In one variation of the invention, a tissue retention or compression dressing (FIGS. 60, 70, 72) method and apparatus are utilized immediately following the tissue removal, ablation and remodeling procedures described previously. For example, following neuroforaminal and lateral recess enlargement, it may be advantageous to leave, as a surgical dressing, a thin flat element 150 pulled tightly against the resected, abraded, or remodeled tissue surface (e.g., around the facet complex 12). The neuroforaminal compression element can be placed around the facet complex. It is expected that a compression dressing of this nature will enhance hemostasis, promote healing and promote subsequent tissue remodeling with the neural foramen 110 widely open. Furthermore, the surgical dressing 150 would provide a barrier to trap tissue debris away from neural or neurovascular structures, while providing an optional technique for delivering medication, possibly as a depot, to the operative site. The dressing 150 would also present a smooth surface towards the nerve root 62 in the immediate post-operative period.

Figure 70:
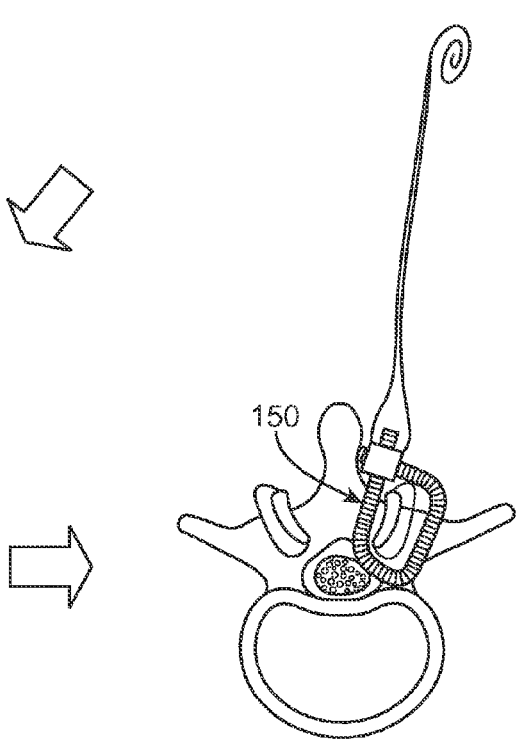
Figure 72A:
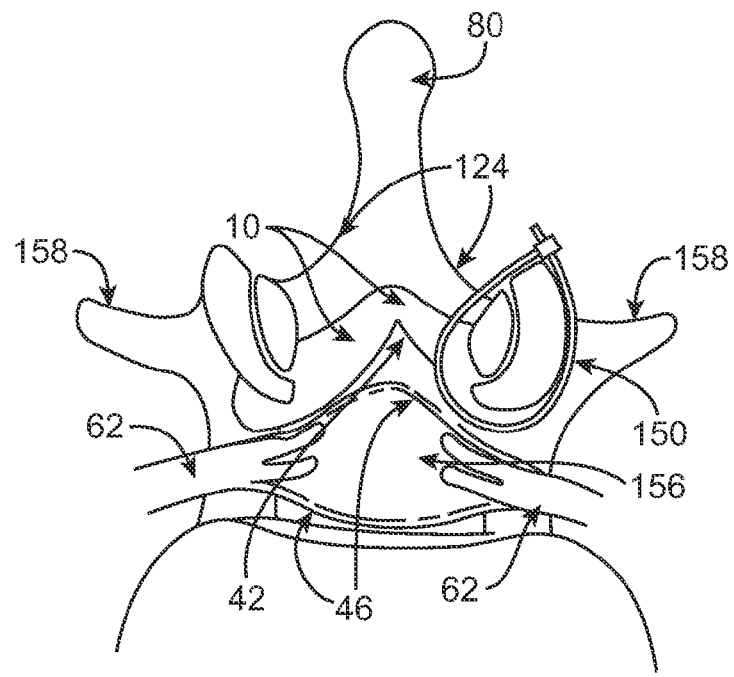
FIG. 72 are schematic cross-sectional views through a patient's spine of a fully implanted compression or retraction remodeling apparatus or compression dressing apparatus.
Figure 72B:
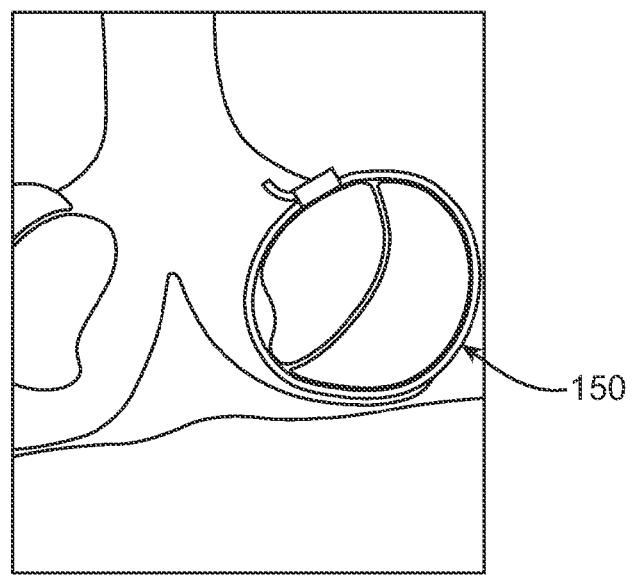

As in FIG. 60, this neuroforaminal compression dressing may be percutaneously held tightly in place against the resected, abraded, or otherwise remodeled surface (e.g., zygapophysial (facet) joint) 77. In certain embodiments, the compression dressing may be either percutaneously removable (as shown in FIGS. 60 and 70), either by pulling the dressing through the neural foramen 110, or by the inclusion of a biodegradable central component of the dressing, such that the two ends may be removed, with the dressing separating at its biodegradable portion in the middle. Other variations such a compression dressing include a totally implanted and completely biodegradable dressing, as illustrated in FIGS. 72*a* or *b*. FIG. 72*a* also illustrates the transverse processes.

Figure 67:
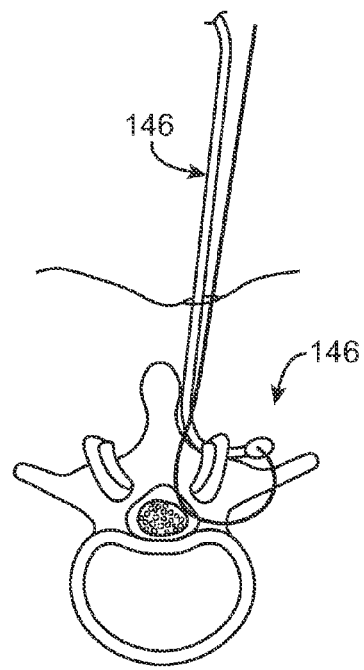
Figure 68:
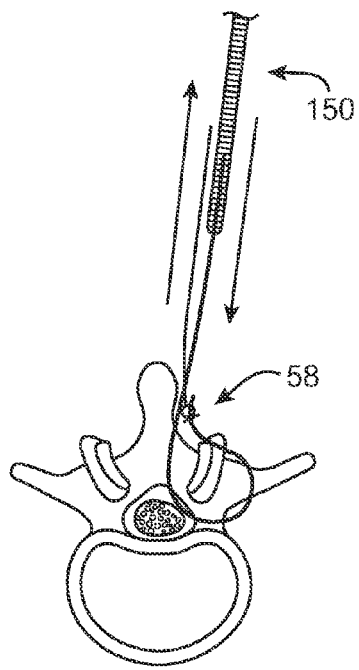
Figure 69:
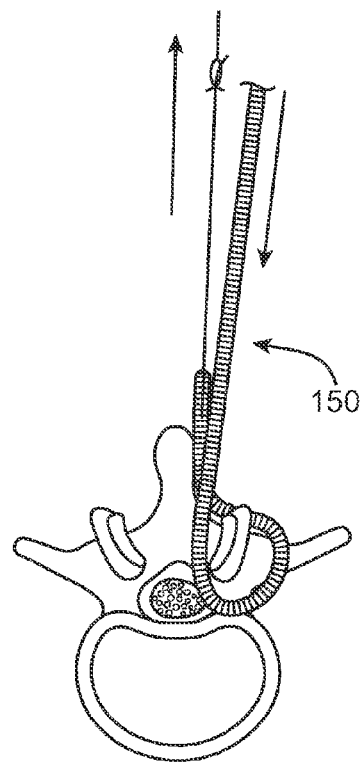

FIGS. 46-56 and 60, and FIGS. 63-70 illustrate midline or paramedian approaches to percutaneous placement of a neuroforaminal compression device (e.g., percutaneous retention compression dressing or tissue remodeling strap) 155 that is wrapped around the facet complex 12 and retracts the posterior aspect of the neural foramina, effectively dilating the space available for the neural and vascular structures. FIGS. 67*a* and *b* illustrate the first steps in a posterior lateral neuroforaminal approach to placement of a compression element (subsequent steps would share similarities with the approach illustrated in FIGS. 46-56 and 60). A grasper, loop or hook 146 can be used for grabbing an end of the guidewire.

Figure 73:
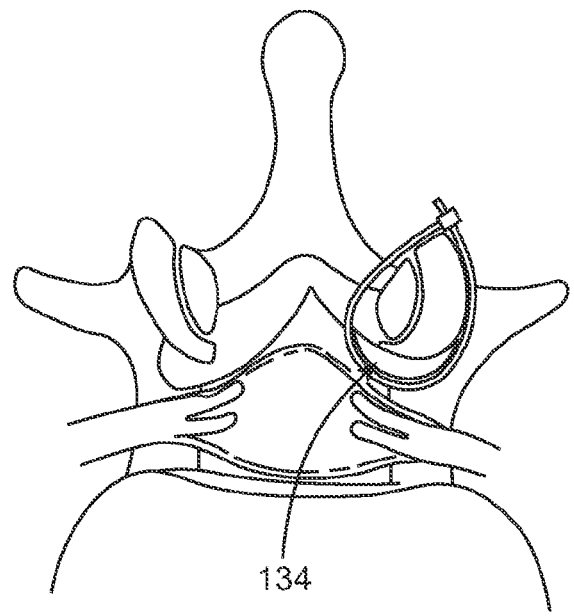
FIG. 73 is a schematic cross-sectional view through a patient's spine of an apparatuses for a compression remodeling strap integrated with a working backstop or barrier.
Figure 74:
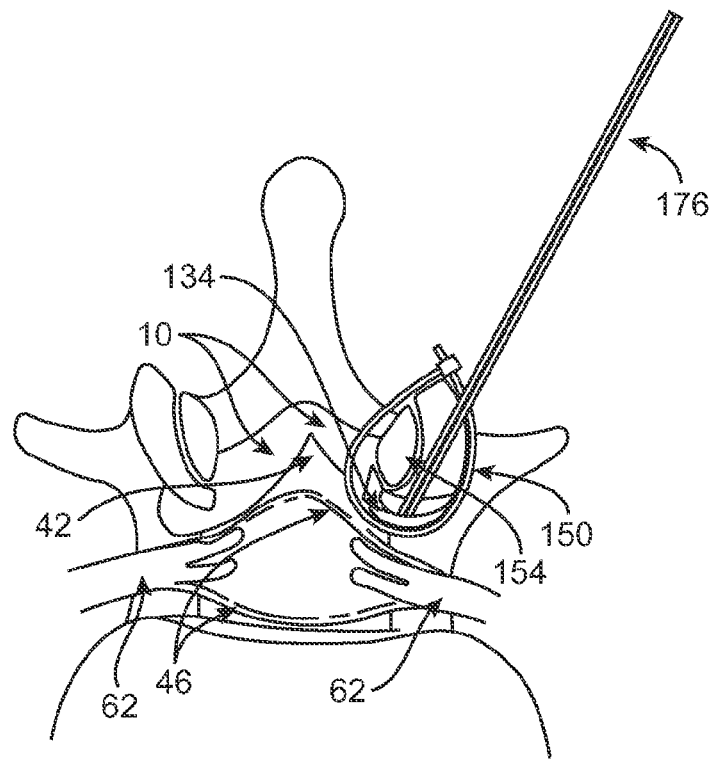
FIG. 74 is a cross-sectional view through a patient's spine that shows a facet drill with a ligament retraction device around a working backstop, and demonstrates a image guided drill used in conjunction with the backstop.
Figure 75:
FIGS. 75-78 are schematic views of cable strap configurations for temporary removable, permanent, or biodegradable compression dressings or remodeling tools.

An additional embodiment of the method and apparatus may combine both the working backstop 134 and the compression element 150, 155, as illustrated in FIGS. 73 and 74. In these illustrations, the compression element 150, 155 serves to keep the working barrier 134 in proper position. Subsequently, image guidance may be used to guide tools used in open or percutaneous procedural approaches to neuroforaminal and lateral recess enlargement. The example in FIG. 74 illustrates an image guided drill 176 removing a portion of the impinging facet complex 12. With the barrier in place, possibly further aided by neural stimulation/localization capabilities, selective and safe tissue removal may be more readily performed.

Figure 76:
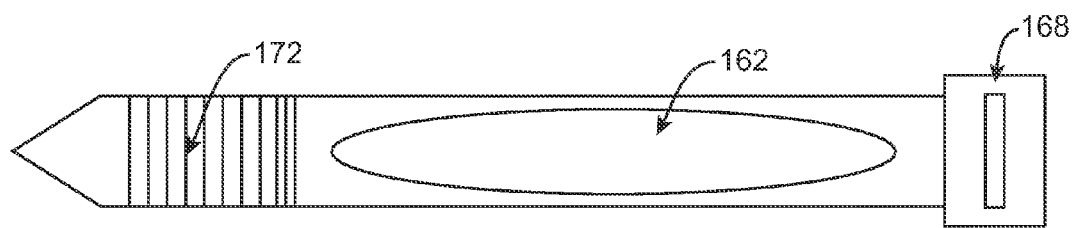
Figure 77:
Figure 78:
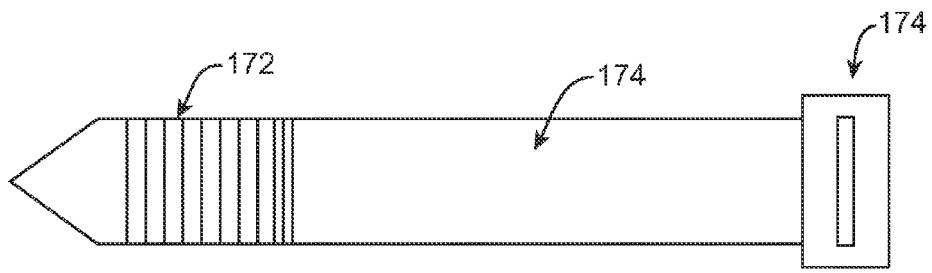

FIGS. 75-78 illustrate some of the compression element embodiments 150, 155. FIG. 76 also contains an area (e.g., a drug depot in a retention strap or compression dressing) 162 for storage of medications for delivery to the tissue retracted by the compression element 150, 155. The compression element can have a locking mechanism that can have a first portion 172 that can insert through a second portion. The compression element can have a locking mechanism that can have a second portion 174 that can receive a first portion 172.

Figure 79:
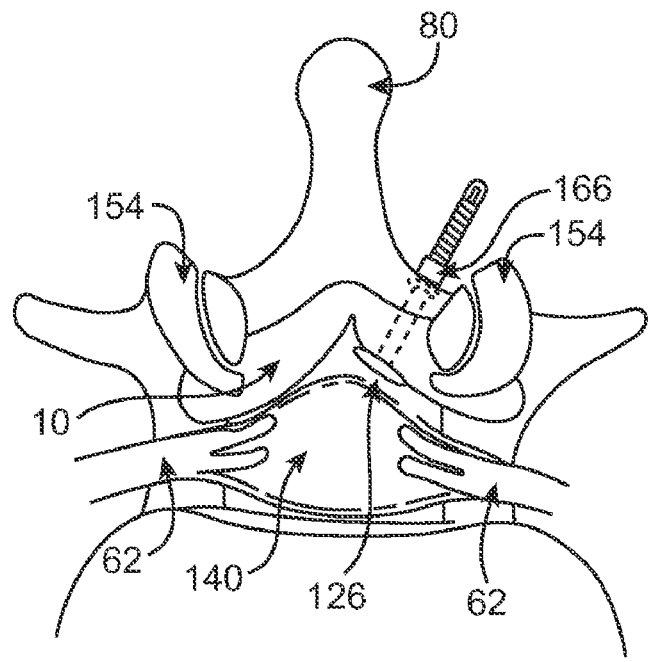
FIGS. 79-80 are schematic cross-sectional and lateral views through a patient's spine of apparatuses for temporary or permanent retraction and retention of the ligamentum flavum.
Figure 80:
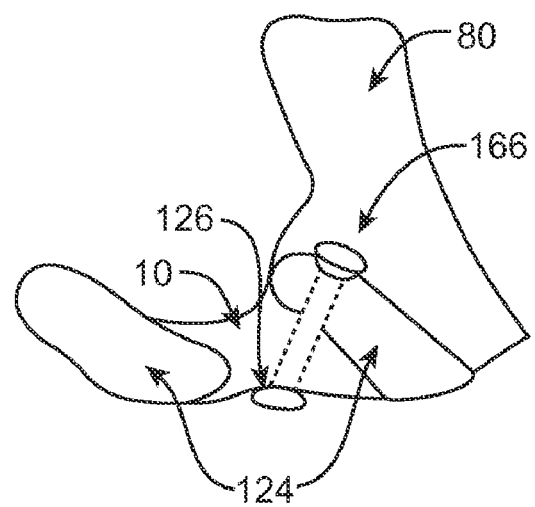

FIGS. 79 and 80 demonstrate additional methods and apparatus for enlargement of the central spinal canal and lateral recess, by retracting the posterior spinal anatomy, in particular the ligamentum flavum 10 (FIGS. 79 and 80 illustrate translaminar ligamentum 10 retraction), in a further posterior direction, away from the dura 46, cauda equina 140, nerve roots 62, and dorsal root ganglia. Such a device would both serve both to retract the spinal tissue posteriorly, and to prevent the posterior elements, particularly the ligamentum flavum 10, from buckling anteriorly 138 into the spinal canal or lateral recess. FIG. 79 illustrates an apparatus with an anchor 126 anterior to or within the ligamentum flavum 10, a second (e.g., laminar) anchor 166 posterior to the lamina 122 (e.g., for posterior retention) and a mechanism for maintaining tension in order to retract the tissues posteriorly, towards the lamina 122. FIG. 80 illustrates a rivet type device that is placed through a hole that has been drilled through the lamina 122. Such a rivet has an anchor 126 placed anterior to the ligamentum flavum 10, which is retracted posteriorly in order to enlarge the central spinal canal and/or lateral recess. Spinal endoscopy may be used as a tool to place a ligamentum flavum 10 retraction system, or in order to confirm that correct placement and efficacy has been achieved.

Most of the safety issues related to the methods and apparatus described herein are similar to those associated with any surgical procedure, e.g., infection and/or bleeding. Some safety issues are more specific to surgery in and around the spine or spinal cord, and are therefore given special consideration below. These generally relate to spinal nerve injury. Morbidity could result from instruments inadvertently passed through the dura mater 46, and creating a cerebrospinal fluid leak and/or damaging the cauda equina 140 (below T12-L1) or spinal cord (above T12-L1) when entering the epidural space 42. Potentially traumatized structures further include nerve roots 62, adjacent vasculature, or dorsal root ganglia.

FIG. 81 are sagittal midline cryosections of the lumbar spine, provided courtesy of Wolfgang Rauchning, Md., that demonstrate the ligamentum flavum 10 protruding ("buckling") anteriorly, a potential mechanism for central or lateral recess neural or neurovascular impingement. The ligamentum flavum 10 is a potential target for abrasive tissue resection using the herein described methods and apparatus.

FIGS. 82, 83, 84, 85, 87 illustrate preferred embodiments of the protective cover or sheath for the abrasion element, in which the abrasive surface is covered 98 and the backside of the abrasive element may also be shielded 48, to prevent tissue damage in areas where tissue abrasion is not intended. The abrasive element's protective cover 6 is ideally shaped to provide optimal protection of vulnerable tissues, at the same time maintaining both a very small profile, for easy threading of the stenotic neural foramen 110; and atraumatic edges (e.g. rounded), in order to prevent cutting of or trauma to neural, vascular or other tissue during placement, use or removal of the device. For example, in certain preferred embodiments, the abrasion device may be tubular (FIG. 82), with an opening over the tissue to be abraded; or may be flat (FIGS. 83, 84, 85, 87) with atraumatic railings or tracks that facilitate passage of the abrasion element, abrasion surface cover, or other instruments. Side channels 82 (e.g., the edge of the backing for the abrasive element), through which the edges of the abrasion element may be maintained or held but are able to slide freely may be of an atraumatic shape. Said side channels may also hold the protective cover 94 for the abrasive side of the abrasion element 14. Note that neural stimulation and localization may be performed through a conductive element 86 in the back cover, the front cover (e.g., a strap tension element 170), or in the abrasive side of the abrasive element itself 14. Both free ends of the device, as well as the ends of the optional protective sheath or cover, are positioned external to the patient for manipulation by a medical practitioner.

FIG. 84 show a similar protective cover and abrasive element configuration to that described in FIG. 83, this time with neural stimulation element 92 only illustrated in the non-abrasive (e.g., non-working) side of the apparatus (e.g., protective cover). In addition, FIGS. 84*e* and 84*f* show that the abrasive element 14 has been replaced by an alternative element for drug deposition 88 (e.g., a drug depot strip for insertion into the compression strap, working backstop or barrier device; a retention strap or belt, or a compression bridge), and/or to serve as part of the compression dressing, when the elements are left under tension against the abraded surface, after the operative procedure. FIG. 84g shows a cross-section through a region of the flexible device having a neural stimulation element comprising a first electrode 92a on one side of the barrier and a second electrode 92b on the tissue modification side of the flexible body, opposite the barrier side. Alternatively, FIG. 84b shows a device including an abrasive element 14 and including at least one medication or bioactive component 201 on the tissue modification surface of the abrasive element 14.

Figure 85A:
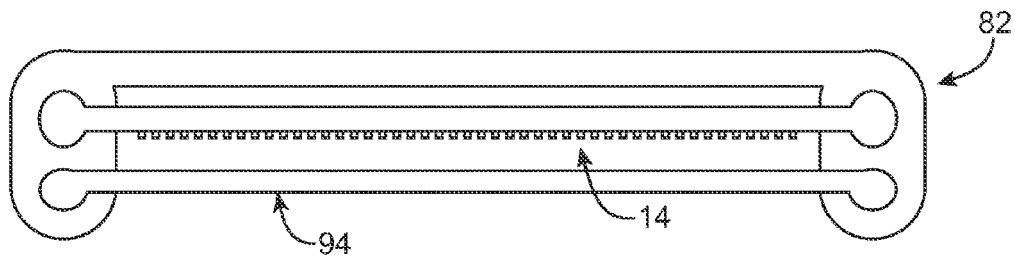
FIG. 85 are schematic cross section views of additional apparatus that may be utilized for selective surgical removal of tissue.
Figure 85B:
Figure 85C:
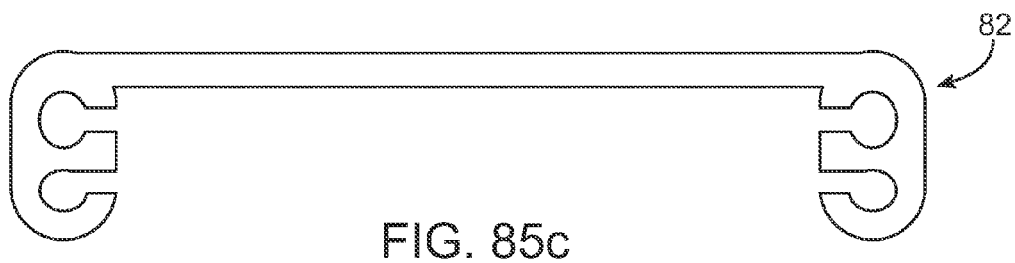

FIG. 85 illustrate an additional similar embodiment of the abrasive element 14 with protective covers 94, 96: the removable cover 94 for the abrasive (i.e., working) side of the of the abrasive element, and the protective working barrier 96 (i.e., the working backstop) for the abrasive element. This time, no neural stimulation elements are illustrated.

Figure 86:
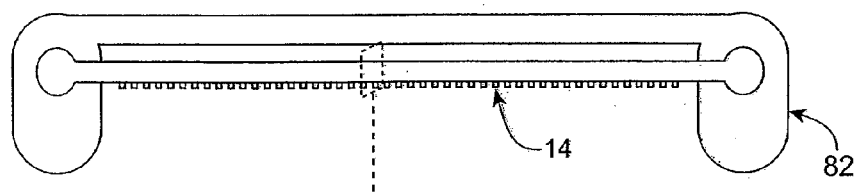
FIG. 86 is a schematic cross section views of additional apparatus that may be utilized for selective surgical removal of tissue.
Figure 87A:
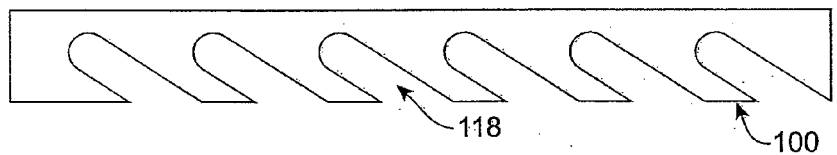
FIG. 87 are close-up schematic views of the resecting element in FIG. 86 that may be utilized for selective surgical removal of tissue.
Figure 87B:
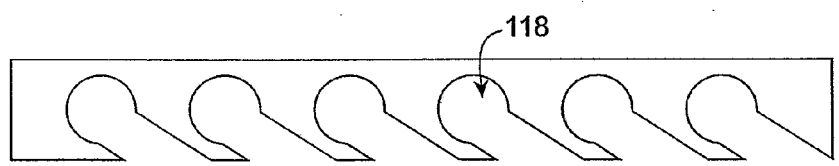
Figure 87C:
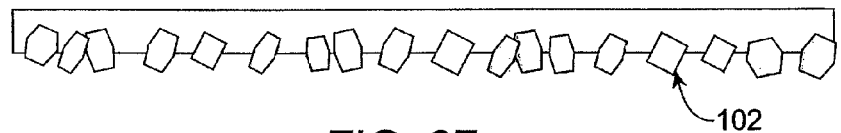
Figure 87D:
Figure 88A:
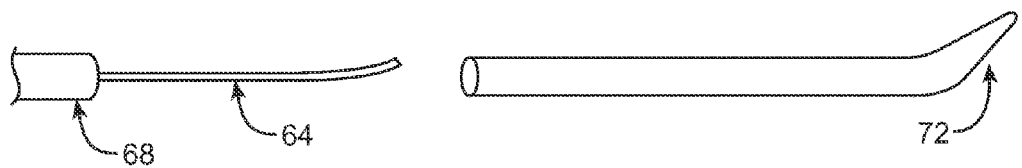
Figure 88B:
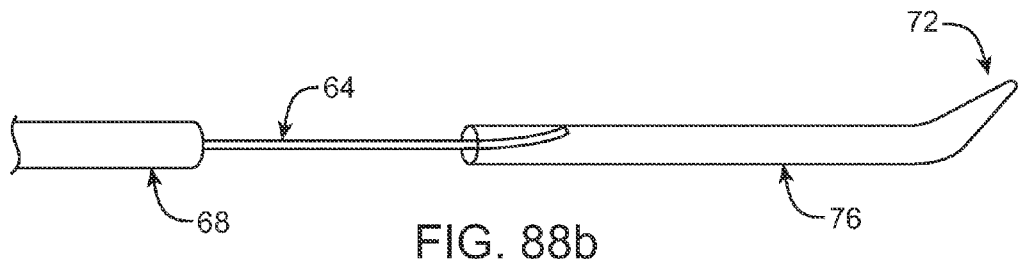
Figure 88C:
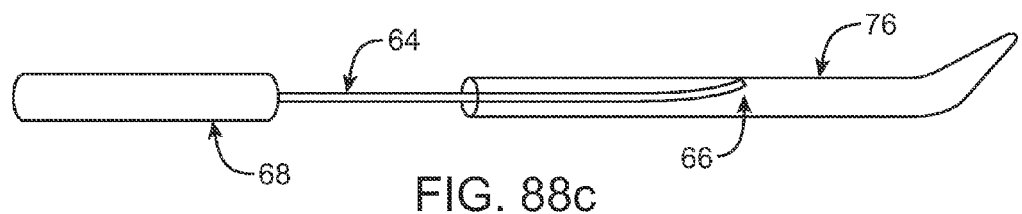
Figure 88D:
Figure 89A:
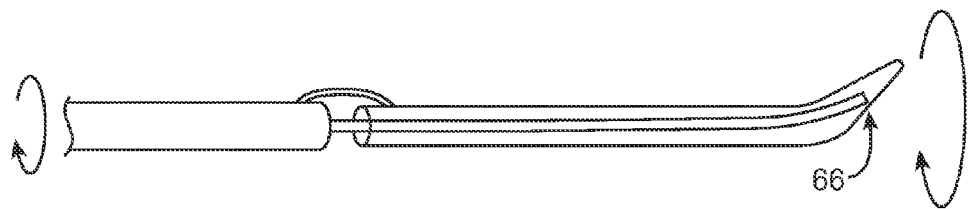
Figure 89B:
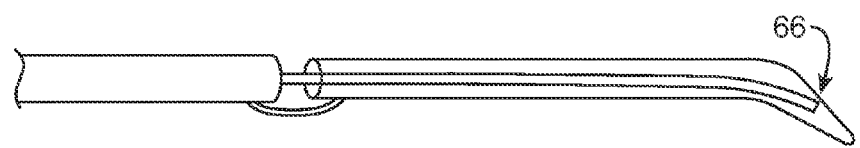
Figure 90A:
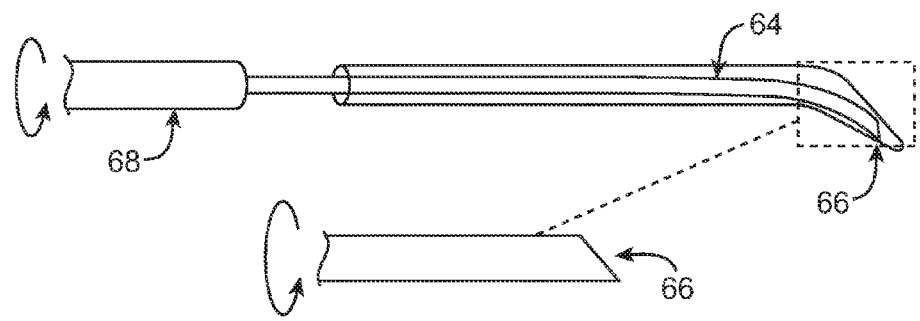
Figure 90B:
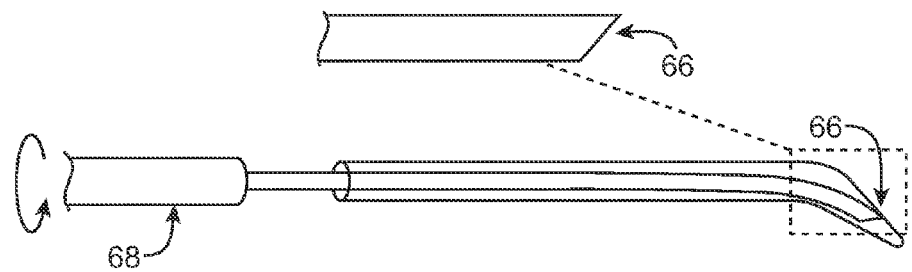
Figure 91A:
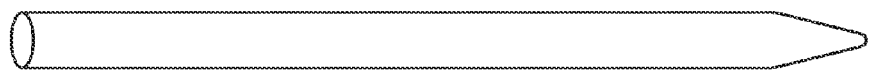
FIGS. 91a-c illustrate various embodiments of a clear tipped cannula with a clear shaft.
Figure 91B:
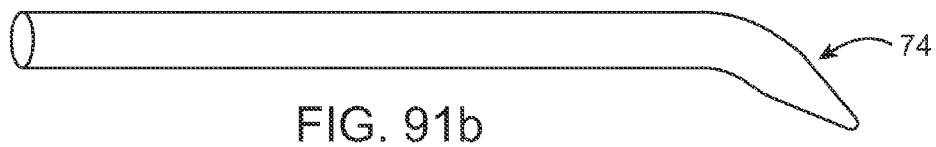
Figure 91C:
Figure 91D:
FIGS. 91d-f illustrate various embodiments of a clear tipped cannula with an opaque shaft.
Figure 91E:
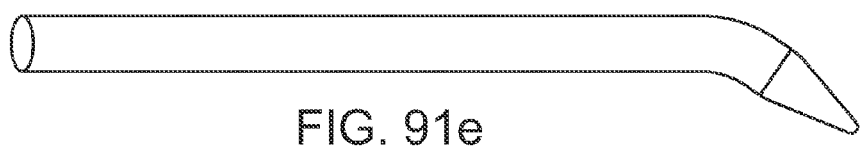
Figure 91F:
Figure 92A:
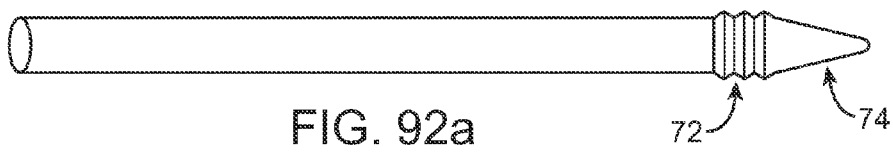
Figure 92B:
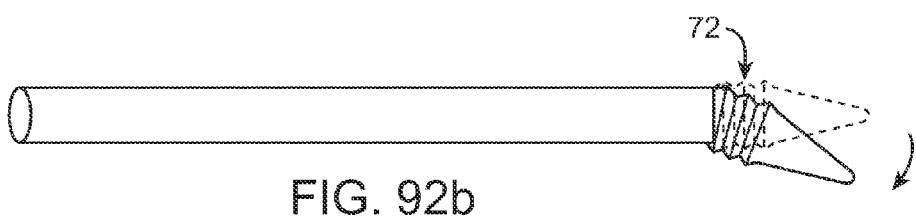
Figure 92C:
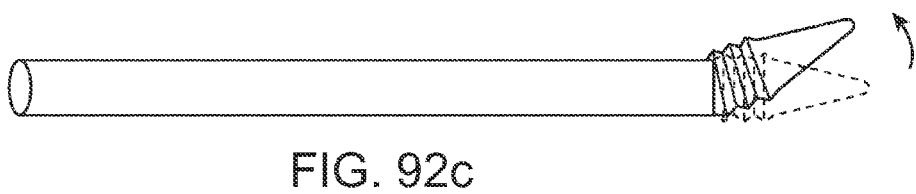
Figure 92D:
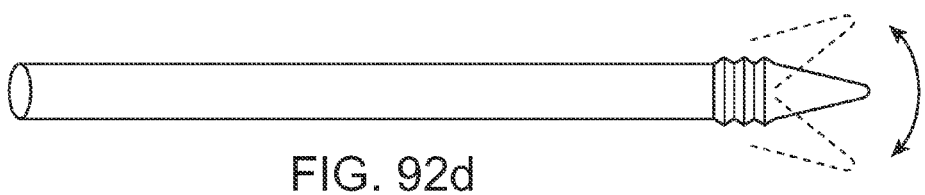
Figure 93:
Figure 94A:
Figure 94B:
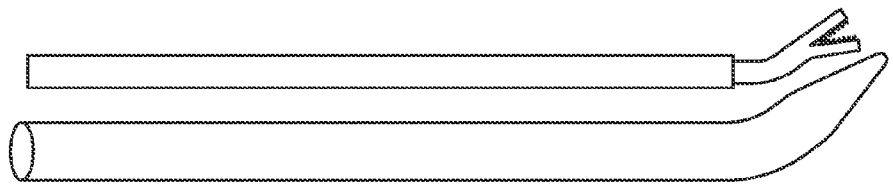
Figure 95A:
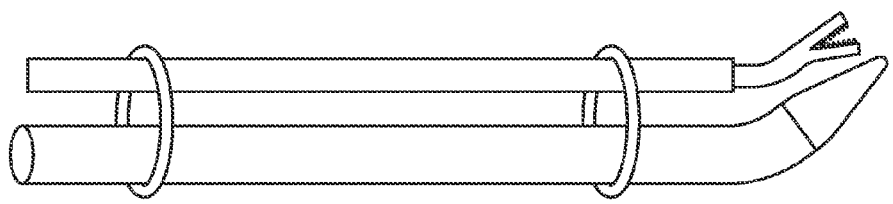
Figure 95B:
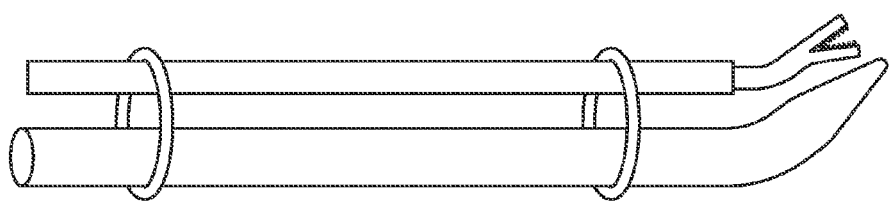
Figure 98A:
Figure 98B:
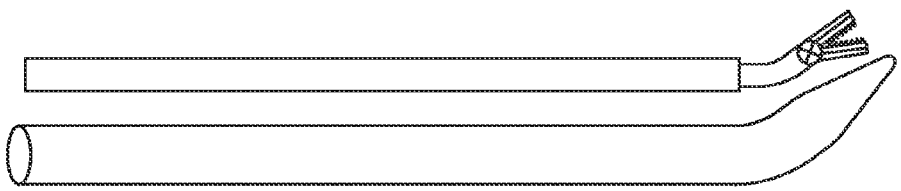
Figure 99A:
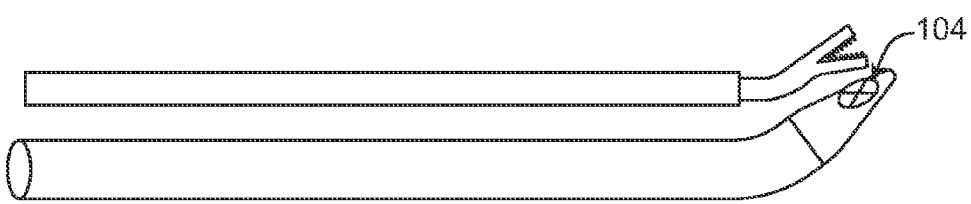
Figure 99B:
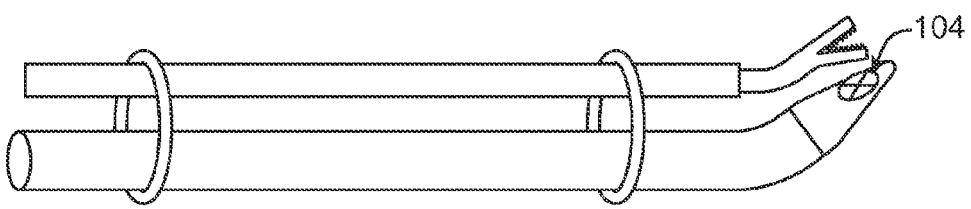

Referring now to FIGS. 86 and 87, cross sections through the abrasive apparatus are illustrated. The abrasive element 14 is seen, housed within the protective covers. As shown, the abrasion element may, for example, be structured as a thin belt or ribbon, with an abrasive 102 and/or cutting surface 100 on one of its sides. The cutting surface 100 can be an abrasive surface of the apparatus with a miniature blade design. The abrasive surface 102 can be an abrasive surface of the apparatus with a sandpaper design. The abrasive element 7 may exist in a variety of shapes, ranging from flat to curved; from narrow to wide; and from a solid to perforated. The abrasive surface of the abrasive element may, in one variation, contain deep grooves 118 or perforations 100a for the transport, collection and removal of (tissue) debris away from the operative site. Alternatively, the pattern of abrasive may be designed to control the direction and speed of movement of the surface across the tissue to be abraded (e.g. deep grooves 118, at a diagonal to the edge of the straps, may be used to facilitate lateral movement of the abrasive element). The width and shape of the abrasive elements may also be varied, in further effort to control the area of tissue to be resected. Finally, in one preferred variation, the surgeon would begin with a coarser grade of abrasive material, in order to gain more aggressive tissue removal. Sequential use of less and less aggressive surfaces would serve to smooth the abraded tissue surface, with the aim of creating an atraumatic surface for contact with neurovascular structures.

Placement of a tissue abrasion device 86 through protective sleeve(s) and 48 into position for selective tissue removal, brings the abrasive surface into contact with the tissue to be removed. A medical practitioner may remove tissue in contact with abrasive surface (FIGS. 87a, b, c, d) by applying a reciprocating or unidirectional motion to the ends of device 86 exterior to the patient. In one variation, a spool or reel to reel configuration may be designed that begins with a coarse grade of abrasive material, and progresses towards less abrasive materials as the spool or reel unwinds.

In one variation, the device includes a compression dressing as illustrated in the percutaneous embodiment described above in FIGS. 60 and 61. Following neuroforaminal and lateral recess enlargement, it may be advantageous to leave, as a surgical dressing, a belt or ribbon pulled tightly against the abraded tissue surface. It is expected that a compression dressing will enhance hemostasis, promote healing and promote subsequent tissue remodeling with the neural foramen 110 widely open. Furthermore, the surgical dressing would provide a barrier to trap tissue debris away from neural or neurovascular structures, while providing an optional technique for delivering medication, possibly as a depot, to the operative site. The dressing would also present a smooth surface towards the nerve root 62 in the immediate postoperative period.

The neuroforaminal compression dressing may, in one preferred embodiment, comprise the optional protective sheath, percutaneously held tightly in place against the abraded surface, after the abrasive apparatus has been removed from its lumen, for a period of time. Alternatively or additionally, a separate percutaneously removable compression dressing may be placed following tissue abrasion. The abrasive material may be followed by a length of compression dressing material on the same reel or spool, or a subsequent reel or spool. Alternatively, a compression dressing may be delivered through the neural foramen 110 as a separate element. The compression element may also be used to deliver medications or other bioactive components (e.g. steroid, biodegradable adhesion barriers, etc.), to the surgical site. The compression dressing material may be, in one variation, partially or completely biodegradable. An entirely biodegradable compression dressing may be placed tightly against the abraded surface, and left completely implanted following the procedure.

Whether placing the apparatus with an epidural needle 2; through the working channel of an epidural needle e.g. 50; with an epidural endoscope; or during an open surgical procedure; image guidance may be used to facilitate safe and accurate placement. If the epidural needle 2 has been replaced by, or converted to, an endoscope, direct visualization of the epidural space 42 may be accomplished. In this case, as illustrated in FIGS. 88-99, the clear tip of the fiberoptic scope will facilitate visualization through the fat present in the epidural space 42. The fiberoptic cable may be rigid or flexible. The endoscope fiberoptic cable tip may be straight or angled, with the flat surface of its distal tip 66 perpendicular (0°, for straight ahead viewing) or at an angle (e.g. 30°, 45°, or 60°). The cannula or portal (e.g., an epidural endoscope) may be closed at its tip or end 76, as in FIGS. 88-99, covering and protecting the distal end of the fiberoptic cable with a clear tip 74 which may be solid, fluid, or gas filled, potentially sized and shaped to expand the area of viewing within the fat filled epidural space 42. Additionally the endoscope or "needlescope" may contain an additional channel or space for infusion of fluid into the epidural space 42, in order to facilitate visualization, to create a space for visualization, and/or to decrease bleeding by increasing pressure, towards or above venous pressure, within the viewing area.

FIGS. 88 through 99 illustrate several embodiments of closed tip portals for epidural fiberoptic visualization. Some description of these portals may be found in the text above. Basically, the portals show several preferred variations of designs that enable visualization through the fat that exists in the epidural space 42. The clear tips of the portals may be solid and clear, or may contain air or clear liquid. The volume of the tip creates a space for improved perspective during visualization.

Referring now to FIG. 88, a hockey stick shaped portal facilitates steering of the portal by rotation of the device. Such a design may be used with a flexible, partially flexible, or rigid fiberoptic element 64. Besides steering the portal tip, the fiberoptic element may be rotated separately in order to direct visualization, when angled scope tips are used (e.g. 30°, 45°, 60°). Alternative embodiments, as illustrated in FIG. 92, may allow the flexible neck (i.e., tip) 72 of the instrument (e.g., the clear tipped epidural endoscope portal) to be steered. FIGS. 94-96, 98, and 99 illustrate means of delivering tools along with the epidural endoscopic portals. Finally, FIG. 97 show a couple of different shapes of the many possible variations that may be helpful in improving visualization and access to the central canal, lateral recesses, neural foramen 110 and posterior annulus of the spine.

Many of the safety issues related to the methods and apparatus described herein are similar to those associated with any surgical procedure, e.g., infection and/or bleeding. Some safety issues are more specific to surgery in and around the spine or spinal cord, and are therefore given special consideration below. These generally relate to spinal neural and neurovascular injury. Central Nervous System injury could result from instruments inadvertently traumatizing the dura mater 46 when entering the epidural space 42, injuring the nerve root(s) 62, the adjacent vasculature, or the dorsal root ganglion as the apparatus is advanced and utilized towards and through the neural foramen 110.

Several techniques may be used to reduce a risk of dural, neural or neurovascular injury, including potentially traumatizing structures including nerve roots 62, adjacent vasculature, or dorsal root ganglia. For example, the tissue alteration (e.g., abrasion) devices may be placed under direct visualization when utilizing an open surgical approach or technique. Likewise, image guidance may be provided during placement or to confirm correct placement. Candidate image guidance techniques include fluoroscopy, fluoroscopy alone, fluoroscopy with additional technology for triangulation and tracking of instruments (e.g. infrared, RF, etc.), MRI, CT, OCT, ultrasound, etc. Catheters or guidewires may include their own image guidance capabilities such as catheter or guidewire-based image guidance, e.g., fiberoptic visualization, catheter-based ultrasound, catheter-based MRI, optical tomography, etc. Alternatively or additionally, endoscopic visualization may be utilized (e.g. flexible fiberoptic endoscope as in Epiduroscope, or via rigid surgical endoscopes), during placement and/or post-placement confirmation of correct placement.

In addition to epidural endoscopy, image guidance may be combined with the use of straight, curved, or steerable guidewires for the proper placement of the neuroforaminal abrasive element. Placement may be achieved percutaneously or through a surgical incision. Such a device may be implanted as an adjunct to an open surgical procedure(s); as an adjunct to an endoscopic surgical procedure(s); or as a separate open, image-guided percutaneous or endoscopic surgical procedure. Percutaneous approaches will enable the surgeon to perform the procedure under local anesthetic in awake or sedated patients, if desired. As discussed, nerve stimulation and localization capabilities may be added to the device in order to enable the surgeon to more safely perform the procedure in an anesthetized, but un-paralyzed patient.

It is expected that the apparatus and methods of the present invention will facilitate a minimally invasive approach to the selective elimination (e.g., alteration, ablation, removal) of pathological spinal tissue, thereby enabling symptomatic relief in patients suffering from spinal stenosis. Spinal neural and neurovascular impingement cause tremendous pain and disability, with symptoms that include back and leg pain, weakness, and decreased sensation. Neural ischemia and injury caused by compression and inflammation may result in a wide range of symptoms or degrees of nerve damage. Symptoms range in severity from mild to severe, and from intermittent to permanent. For example, neurogenic claudication, which is exacerbated by back extension (as occurs when one stands erect and places the spine in extension), may be mild or severe. Symptoms of neurogenic claudication are usually improved by changes in posture that lead to back flexion, such as sitting. The most severe cases of spinal stenosis may lead to permanent neurological damage, including the possibility of the development of cauda equina syndrome.

Spine surgeons lack safe and effective techniques or tools to minimally invasively or percutaneously reduce neural and neurovascular impingement in the spine, while minimizing collateral tissue damage. It is expected that the apparatus and methods of the present invention may be utilized for lateral recess and neuroforaminal enlargement to provide adequate bone and soft tissue resection, while reducing unnecessary destruction of functional bone, ligament or muscle in order to gain access to the tissues to be resected or modified.

Because critical neural and neurovascular structures are in close proximity to the areas where surgical manipulation, dissection, resection, ablation and remodeling would be therapeutically valuable in the spine, safety at each step in the procedure is of critical importance in order to avoid disabling neurological damage to the patient. For this reason, safety measures, such as working barriers and nerve localization via an integrated nerve stimulator, are described.

Although preferred illustrative embodiments of the present invention are described hereinabove, it will be apparent to those skilled in the art that various changes and modifications may be made thereto without departing from the invention. It is intended in the appended claims to cover all such changes and modifications that fall within the true spirit and scope of the invention.

We claim:

1. A surgical tissue modification device for use with a nerve stimulation apparatus, the tissue modification device comprising:
   an elongate flexible body attachable;
   at the distal end of the elongate flexible body to a guidewire so that the device can be positioned or actuated by pulling on the guidewire;
   at least one tissue modification surface located on the body;
   at least one electrode attached to the body; and
   a connector for electrically coupling the electrode to the nerve stimulation apparatus,
   wherein the device is configured to attach to the guidewire so that the tissue modification surface of the flexible body can be positioned or actuated by pulling on the guidewire from a distal end of the guidewire extending out of a patient's body to urge the tissue modification surface against the target tissue.

2. The surgical tissue modification device of claim 1, further comprising at least one barrier located over a portion of the tissue modification surface.

3. The surgical tissue modification device of claim 2, where the barrier further comprises at least one window through which the tissue modification surface may contact tissue when the barrier is placed over the tissue modification surface.

4. The surgical tissue modification device of claim 2, where the barrier is slidable relative to the tissue modification surface.

5. The surgical tissue modification device of claim 2, where at least one electrode is located on the barrier.

6. The surgical tissue modification device of claim 2, where the at least one electrode comprises at least two electrodes, where the electrodes are located in at least one of the following combinations, one on each side of the flexible body, one on each side of the barrier, one on the tissue modification side of the flexible body and one on the opposite side of the barrier.

7. The surgical tissue modification device of claim 1, where the tissue modification surface is located on a first side of the flexible body and the electrode is located on the first side of the body.

8. The surgical tissue modification device of claim 1, where the tissue modification surface comprises a plurality of grooves.

9. The surgical tissue modification device of claim 1, where the tissue modification surface comprises a plurality of perforations.

10. The surgical tissue modification device of claim 1, where the flexible body comprises a shape selected from the group consisting of a flat shape, a ribbon shape, and a tubular shape.

11. The surgical tissue modification device of claim 1, further comprising at least one medication or bioactive component for delivery to the tissue located on the tissue modification surface.

12. The surgical tissue modification device of claim 11, where the medication or bioactive component is selected from the group consisting of steroids, procoagulants, bone wax, and adhesion barriers.

13. A surgical system for modifying target tissue in a patient, the system comprising:
   an elongate, at least partially flexible body attachable to a guidewire, the elongate flexible body including a tissue modification surface and an atraumatic surface; and
   a guidewire having a distal end,
   wherein the elongate body is configured to attach the elongate body to the guidewire so that the tissue modification surface of the flexible body can be positioned or actuated by pulling on the guidewire, so that when a flexible portion of the body passes along a curved surface between the target tissue and non-target tissue, a distal end of the guidewire extending out of the body can be pulled to apply a distal tensioning force to urge the tissue modification surface against the target tissue.

14. A system as in claim 13, wherein the tissue modification surface comprises a plurality of tissue cutting members fixedly attached to the elongate body.

15. A system as in claim 13, wherein the tissue modification surface comprises one or more movable blades.

16. A system as in claim 13, wherein the elongate body comprises a guidewire lumen.

17. A system as in claim 13, wherein the elongate body comprises a device for fixedly coupling the guidewire with the elongate body.

18. A system for modifying target tissue in a spine of a patient, the system comprising:
   an elongate, at least partially flexible body attachable to a guidewire;
   a deployment system for advancing the flexible body from outside the patient, through an intervertebral foramen of the patient's spine, and out of the patient, such that a flexible portion of the body passes along a curved path between the target tissue and non-target tissue, and such that tensioning force may be applied at or near opposite ends of the device to urge the flexible portion against the target tissue during a tissue modification procedure;
   a tissue modification surface disposed along the flexible portion of the elongate body;
   wherein the elongate body is attachable at the distal end of the elongate flexible body to a guidewire so that the device can be positioned or actuated by pulling on the guidewire from a distal end of the guidewire extending out of the patient's body to urge the tissue modification surface against the target tissue; and
   an atraumatic surface disposed along the flexible portion such that when the tissue modification surface faces the target tissue, the atraumatic surface faces non-target tissue.

19. A system as in claim 18, wherein the elongate body comprises:
   a shaft, including the flexible portion of the body; and
   a flexible guidewire attached to the shaft.

* * * * *